US008313760B2

(12) United States Patent
Hunter et al.

(10) Patent No.: US 8,313,760 B2
(45) Date of Patent: Nov. 20, 2012

(54) COMPOSITIONS AND METHODS FOR COATING MEDICAL IMPLANTS

(75) Inventors: William L Hunter, Vancouver (CA); David M Gravett, Mountain View, CA (US); Philip M Toleikis, Vancouver (CA); Richard T Liggins, Coquitlam (CA); Troy A. E. Loss, North Vancouver (CA)

(73) Assignee: Angiotech International AG, Zug (CH)

( * ) Notice: Subject to any disclaimer, the term of this patent is extended or adjusted under 35 U.S.C. 154(b) by 708 days.

(21) Appl. No.: 12/107,629

(22) Filed: Apr. 22, 2008

(65) Prior Publication Data
US 2009/0060973 A1    Mar. 5, 2009

Related U.S. Application Data

(63) Continuation-in-part of application No. 10/447,309, filed on May 27, 2003, now abandoned.

(60) Provisional application No. 60/383,419, filed on May 24, 2002.

(51) Int. Cl.
*A61F 2/00* (2006.01)
*A61K 31/505* (2006.01)

(52) U.S. Cl. ......... 424/423; 424/422; 424/424; 424/426

(58) Field of Classification Search ............... 424/423, 424/424; 427/2.23, 2.35, 2.28, 2.4; 623/1.1, 623/11, 12
See application file for complete search history.

(56) References Cited

U.S. PATENT DOCUMENTS

| | | | |
|---|---|---|---|
| 3,852,450 A | 12/1974 | Silvestri et al. | 424/251 |
| 3,980,650 A | 9/1976 | Nauta | 260/256.4 Q |
| 4,017,626 A | 4/1977 | Gauri | 424/251 |
| 4,033,962 A | 7/1977 | Rosen | 260/256.4 N |
| 4,215,062 A | 7/1980 | Mitscher | 260/365 |
| 4,232,022 A | 11/1980 | Ponsford | 424/251 |
| 4,296,105 A | 10/1981 | Baurain et al. | 424/180 |
| 4,500,676 A | 2/1985 | Balazs et al. | 525/54.2 |
| 4,534,899 A | 8/1985 | Sears | 260/403 |
| 4,582,865 A | 4/1986 | Balazs et al. | 524/29 |
| 4,590,270 A | 5/1986 | Kompis et al. | 544/320 |
| 4,629,623 A | 12/1986 | Balazs et al. | 424/78 |
| 4,636,524 A | 1/1987 | Balazs et al. | 514/781 |
| 4,649,198 A | 3/1987 | Irikura et al. | 544/281 |
| 4,713,371 A | 12/1987 | Aretz et al. | 514/34 |
| 4,713,448 A | 12/1987 | Balazs et al. | 536/55.1 |
| 4,714,703 A | 12/1987 | Burckhalter | 514/274 |
| 4,774,249 A | 9/1988 | Kompis et al. | 514/272 |
| 4,795,741 A | 1/1989 | Leshchiner et al. | 514/21 |
| 4,814,182 A | 3/1989 | Graham et al. | 424/484 |
| 4,882,168 A | 11/1989 | Casey et al. | 424/468 |
| 4,888,176 A | 12/1989 | Langer et al. | 424/426 |
| 4,891,225 A | 1/1990 | Langer et al. | 424/428 |
| 4,913,743 A | 4/1990 | Brode et al. | 106/162 |
| 4,925,668 A | 5/1990 | Khan et al. | 424/422 |
| 4,976,697 A | 12/1990 | Walder et al. | 604/164 |
| 4,999,210 A | 3/1991 | Solomon et al. | 427/2 |
| 5,013,306 A | 5/1991 | Solomon et al. | 604/265 |
| 5,015,238 A | 5/1991 | Solomon et al. | 604/164 |
| 5,059,186 A | 10/1991 | Yamamoto et al. | 604/280 |
| 5,064,415 A | 11/1991 | Walder et al. | 604/164 |
| 5,069,899 A | 12/1991 | Whitbourne et al. | 424/56 |
| 5,091,442 A | 2/1992 | Milner | 523/122 |
| 5,099,013 A | 3/1992 | Balazs et al. | 536/55.1 |
| 5,128,326 A | 7/1992 | Balazs et al. | 514/54 |
| 5,130,126 A | 7/1992 | Koyama et al. | 424/78.18 |
| 5,143,724 A | 9/1992 | Leshchiner et al. | 424/78.08 |
| 5,145,684 A | 9/1992 | Liversidge et al. | 424/489 |
| 5,153,174 A | 10/1992 | Band et al. | 514/12 |
| 5,165,952 A | 11/1992 | Solomon et al. | 427/2 |
| 5,207,648 A | 5/1993 | Gross | 604/164 |
| 5,221,256 A | 6/1993 | Mahurkar | 604/43 |
| 5,238,926 A | 8/1993 | Cooper et al. | 514/50 |
| 5,242,073 A | 9/1993 | Willis et al. | 220/240 |
| 5,246,698 A | 9/1993 | Leshchiner et al. | 424/78.08 |
| 5,266,563 A | 11/1993 | Balazs et al. | 514/42 |
| 5,301,664 A | 4/1994 | Sievers et al. | 128/200.23 |
| 5,322,520 A | 6/1994 | Milder | 604/265 |
| 5,330,756 A | 7/1994 | Steuart et al. | 424/405 |
| 5,346,898 A | 9/1994 | Cooper et al. | 514/255 |
| 5,366,505 A | 11/1994 | Farber | 623/11 |
| 5,378,475 A | 1/1995 | Smith et al. | 424/473 |
| 5,399,351 A | 3/1995 | Leshchiner et al. | 424/422 |
| 5,399,363 A | 3/1995 | Liversidge et al. | 424/490 |
| 5,403,858 A | 4/1995 | Bastard et al. | 514/449 |
| 5,407,683 A | 4/1995 | Shively | 424/439 |
| 5,438,072 A | 8/1995 | Bobee et al. | 514/449 |
| 5,439,686 A | 8/1995 | Desai et al. | 424/451 |
| 5,451,424 A | 9/1995 | Solomon et al. | 427/2.1 |

(Continued)

FOREIGN PATENT DOCUMENTS

| | | |
|---|---|---|
| DE | 19718430 A1 | 1/1999 |
| EP | 0117485 A2 | 9/1984 |
| EP | 0134928 A1 | 3/1985 |
| EP | 0171739 A1 | 2/1986 |
| EP | 0 774 258 A1 | 5/1997 |
| EP | 0778258 A2 | 6/1997 |
| EP | 0 882 461 A2 | 12/1998 |
| EP | 0955056 A1 | 11/1999 |
| EP | 1065202 A1 | 1/2001 |
| EP | 0 633 032 B1 | 2/2001 |

(Continued)

OTHER PUBLICATIONS

Andoh et al., "Formation and Fate of Abnormal Ribosomes of *E. coli* Cells Treated with 5-Fluorouracil," *Proc. Nat. Acad. Sci.*, 54:1181-1189, 1965.

(Continued)

*Primary Examiner* — Michael G Hartley
*Assistant Examiner* — Jagadishwar Samala
(74) *Attorney, Agent, or Firm* — SEED IP Law Group PLLC

(57) ABSTRACT

Medical implants are provided which release a fluoropyrimidine or an analog thereof, thereby inhibiting or reducing the incidence of infection associated with the implant.

8 Claims, 2 Drawing Sheets

U.S. PATENT DOCUMENTS

| | | | |
|---|---|---|---|
| 5,472,417 A | 12/1995 | Martin et al. | 604/43 |
| 5,498,248 A | 3/1996 | Milder | 604/265 |
| 5,512,055 A | 4/1996 | Domb et al. | 604/265 |
| 5,520,664 A | 5/1996 | Bricault, Jr. et al. | 604/265 |
| 5,525,348 A | 6/1996 | Whitbourne et al. | 424/423 |
| 5,534,250 A | 7/1996 | Klaveness et al. | 424/78.37 |
| 5,554,106 A | 9/1996 | Layman-Spillar et al. | 602/42 |
| 5,569,207 A | 10/1996 | Gisselberg et al. | 604/175 |
| 5,574,097 A | 11/1996 | Klaveness et al. | 525/61 |
| 5,594,158 A | 1/1997 | Wheeler | 552/201 |
| 5,609,629 A | 3/1997 | Fearnot et al. | 623/1 |
| 5,616,119 A | 4/1997 | Davis | 604/19 |
| 5,616,338 A | 4/1997 | Fox, Jr. et al. | 424/423 |
| 5,620,419 A | 4/1997 | Lui et al. | 604/116 |
| 5,624,704 A | 4/1997 | Darouiche et al. | 427/2.24 |
| 5,707,366 A | 1/1998 | Solomon et al. | 604/265 |
| 5,709,672 A | 1/1998 | Illner | 604/265 |
| 5,716,981 A | 2/1998 | Hunter et al. | 514/449 |
| 5,725,553 A | 3/1998 | Moenning | 606/213 |
| 5,725,817 A | 3/1998 | Milder | 264/104 |
| 5,741,224 A | 4/1998 | Milder et al. | 604/20 |
| 5,741,779 A | 4/1998 | White et al. | 514/12 |
| 5,752,941 A | 5/1998 | Romano et al. | 604/265 |
| 5,759,564 A | 6/1998 | Milder | 424/426 |
| 5,783,689 A | 7/1998 | Miller et al. | 536/28.52 |
| 5,797,869 A | 8/1998 | Martin et al. | 604/43 |
| 5,798,115 A | 8/1998 | Santerre et al. | 424/423 |
| 5,800,412 A | 9/1998 | Zhang et al. | 604/280 |
| 5,817,666 A | 10/1998 | Katz | 514/274 |
| 5,824,049 A | 10/1998 | Ragheb et al. | 623/1 |
| 5,837,226 A | 11/1998 | Jungherr et al. | 424/78.1 |
| 5,843,903 A | 12/1998 | Schally et al. | 514/16 |
| 5,854,382 A | 12/1998 | Loomis | 528/354 |
| 5,861,191 A | 1/1999 | Ferralli | 427/316 |
| 5,873,904 A | 2/1999 | Ragheb et al. | 623/1 |
| 5,886,026 A | 3/1999 | Hunter et al. | 514/449 |
| 5,895,419 A | 4/1999 | Tweden et al. | 623/2 |
| 5,902,283 A | 5/1999 | Darouiche et al. | 604/265 |
| 5,912,225 A | 6/1999 | Mao et al. | 514/2 |
| 5,921,954 A | 7/1999 | Mohr, Jr. et al. | 604/53 |
| 5,921,965 A | 7/1999 | Blei | 604/204 |
| 5,935,930 A | 8/1999 | White et al. | 514/12 |
| 5,942,555 A | 8/1999 | Swanson et al. | 522/35 |
| 5,994,341 A | 11/1999 | Hunter et al. | 514/210 |
| 5,997,517 A | 12/1999 | Whitbourne | 604/265 |
| 6,005,020 A | 12/1999 | Loomis | 523/105 |
| 6,007,833 A | 12/1999 | Chudzik et al. | 424/425 |
| 6,059,816 A | 5/2000 | Moenning | 606/213 |
| 6,060,000 A | 5/2000 | Milder et al. | 252/510 |
| 6,063,396 A | 5/2000 | Kelleher | 424/428 |
| 6,071,447 A | 6/2000 | Bootman et al. | 264/54 |
| 6,090,995 A | 7/2000 | Reich et al. | 623/11 |
| 6,096,070 A | 8/2000 | Ragheb et al. | 623/1 |
| 6,099,563 A | 8/2000 | Zhong | 623/1.46 |
| 6,106,473 A | 8/2000 | Violante et al. | 600/458 |
| 6,107,280 A | 8/2000 | White et al. | 514/12 |
| 6,110,483 A | 8/2000 | Whitbourne et al. | 424/423 |
| 6,117,125 A | 9/2000 | Rothbarth et al. | 604/523 |
| 6,121,027 A | 9/2000 | Clapper et al. | 435/180 |
| 6,132,765 A | 10/2000 | DiCosmo et al. | 424/450 |
| 6,149,574 A | 11/2000 | Trauthen et al. | 600/3 |
| 6,153,212 A | 11/2000 | Mao et al. | 424/426 |
| 6,156,345 A | 12/2000 | Chudzik et al. | 424/424 |
| 6,166,173 A | 12/2000 | Mao et al. | 528/398 |
| 6,179,817 B1 | 1/2001 | Zhong | 604/265 |
| 6,197,051 B1 | 3/2001 | Zhong | 623/1.46 |
| 6,197,785 B1 | 3/2001 | Jackson et al. | 514/309 |
| 6,206,849 B1 | 3/2001 | Martin et al. | 604/43 |
| 6,214,901 B1 | 4/2001 | Chudzik et al. | 523/113 |
| 6,238,687 B1 | 5/2001 | Mao et al. | 424/426 |
| 6,261,271 B1 | 7/2001 | Solomon et al. | 604/265 |
| 6,273,875 B1 | 8/2001 | Siman et al. | 604/264 |
| 6,287,484 B1 | 9/2001 | Hausslein et al. | 252/512 |
| 6,299,604 B1 | 10/2001 | Ragheb et al. | 604/265 |
| 6,309,660 B1 | 10/2001 | Hsu et al. | 424/425 |
| 6,316,522 B1 | 11/2001 | Loomis et al. | 523/105 |
| 6,322,797 B1 | 11/2001 | Mao et al. | 424/271 |
| 6,335,029 B1 | 1/2002 | Kamath et al. | 424/423 |
| 6,338,904 B1 | 1/2002 | Patnaik et al. | 428/423.1 |
| 6,340,465 B1 | 1/2002 | Hsu et al. | 424/400 |
| 6,344,035 B1 | 2/2002 | Chudzik et al. | 604/265 |
| 6,355,001 B1 | 3/2002 | Quinn et al. | 600/505 |
| 6,361,526 B1 | 3/2002 | Reisdorf et al. | 604/265 |
| 6,383,144 B1 | 5/2002 | Mooney et al. | 600/549 |
| 6,387,052 B1 | 5/2002 | Quinn et al. | 600/505 |
| 6,403,618 B1 | 6/2002 | Fernandez-Pol | 514/354 |
| 6,403,758 B1 | 6/2002 | Loomis | 528/354 |
| 6,409,723 B1 | 6/2002 | Edwards | 606/41 |
| 6,409,764 B1 | 6/2002 | White et al. | 623/16.11 |
| 6,419,673 B1 | 7/2002 | Edwards et al. | 606/41 |
| 6,423,050 B1 | 7/2002 | Twardowski | 604/500 |
| 6,425,853 B1 | 7/2002 | Edwards | 600/29 |
| 6,468,649 B1 | 10/2002 | Zhong | 428/341 |
| 6,475,434 B1 | 11/2002 | Darouiche | 422/28 |
| 6,485,430 B1 | 11/2002 | Quinn et al. | 600/505 |
| 6,485,737 B1 | 11/2002 | Mao et al. | 424/426 |
| 6,497,729 B1 | 12/2002 | Moussy et al. | 623/23.57 |
| 6,506,411 B2 | 1/2003 | Hunter et al. | 424/501 |
| 6,518,426 B1 | 2/2003 | Gangjee | 544/280 |
| 6,530,951 B1 | 3/2003 | Bates et al. | 623/1.45 |
| 6,541,481 B2 | 4/2003 | Kath et al. | 514/260.1 |
| 6,544,544 B2 | 4/2003 | Hunter et al. | 424/424 |
| 6,599,275 B1 | 7/2003 | Fischer, Jr. | 604/265 |
| 6,599,881 B1 | 7/2003 | White et al. | 514/12 |
| 6,685,672 B1 | 2/2004 | Forman | 604/101.03 |
| 6,730,064 B2 | 5/2004 | Ragheb et al. | 604/265 |
| 6,730,313 B2 | 5/2004 | Helmus et al. | 424/423 |
| 6,740,333 B2 | 5/2004 | Beckett et al. | 424/436 |
| 6,753,071 B1 | 6/2004 | Pacetti | 428/212 |
| 6,756,428 B2 | 6/2004 | Denesuk | 524/47 |
| 6,774,278 B1 | 8/2004 | Ragheb et al. | 623/11 |
| 6,786,922 B2 | 9/2004 | Schaeffer | 623/1.15 |
| 6,918,927 B2 | 7/2005 | Bates et al. | 623/1.15 |
| 6,926,919 B1 | 8/2005 | Hossainy et al. | 427/2.25 |
| 6,942,634 B2 | 9/2005 | Odland | 604/6.09 |
| 6,971,813 B2 | 12/2005 | Shekalim et al. | 401/208 |
| 6,991,804 B2 | 1/2006 | Helmus et al. | 424/423 |
| 6,997,894 B2 | 2/2006 | Caresio | 604/6.16 |
| 6,997,898 B2 | 2/2006 | Forman | 604/101.03 |
| 7,004,176 B2 | 2/2006 | Lau | 128/898 |
| 7,011,682 B2 | 3/2006 | Lashinski et al. | 623/2.37 |
| 7,087,089 B2 | 8/2006 | Patel et al. | 623/23.72 |
| 7,175,873 B1 | 2/2007 | Roorda et al. | 427/2.14 |
| 7,201,745 B2 | 4/2007 | DiMatteo et al. | 604/523 |
| 7,254,946 B1 | 8/2007 | Quinn et al. | 60/505 |
| 7,255,891 B1 | 8/2007 | Pacetti | 427/2.24 |
| 7,296,577 B2 | 11/2007 | Lashinski et al. | 128/898 |
| 7,306,580 B2 | 12/2007 | Paul et al. | 604/264 |
| 7,311,697 B2 | 12/2007 | Osborne | 604/524 |
| 7,335,228 B2 | 2/2008 | Schaeffer | 623/1.15 |
| 7,344,599 B2 | 3/2008 | Shekalim et al. | 118/264 |
| 2001/0049422 A1 | 12/2001 | Phaneuf et al. | 525/452 |
| 2002/0016297 A1 | 2/2002 | Linde, II et al. | 514/19 |
| 2002/0018795 A1 | 2/2002 | Whitbourne et al. | 424/414 |
| 2002/0049349 A1 | 4/2002 | Kohlstruk et al. | 560/25 |
| 2002/0055666 A1 | 5/2002 | Hunter et al. | 600/1 |
| 2002/0065546 A1 | 5/2002 | Machan et al. | 623/1.13 |
| 2002/0091230 A1 | 7/2002 | Mao et al. | 528/398 |
| 2002/0133072 A1 | 9/2002 | Wang et al. | 600/423 |
| 2002/0137814 A1 | 9/2002 | Dang et al. | 523/122 |
| 2002/0151617 A1 | 10/2002 | Mao et al. | 523/115 |
| 2003/0004209 A1 | 1/2003 | Hunter et al. | 514/449 |
| 2003/0036794 A1 | 2/2003 | Ragheb et al. | 623/1.15 |
| 2003/0055053 A1 | 3/2003 | Linde, II et al. | 514/227.8 |
| 2003/0108588 A1 | 6/2003 | Chen et al. | 424/423 |
| 2003/0144362 A1 | 7/2003 | Utterberg et al. | 514/724 |
| 2003/0144570 A1 | 7/2003 | Hunter et al. | 600/1 |
| 2003/0175323 A1 | 9/2003 | Utterberg et al. | 424/423 |
| 2003/0216758 A1 | 11/2003 | Signore | 606/151 |
| 2003/0229390 A1 | 12/2003 | Ashton et al. | 623/1.15 |
| 2004/0043052 A1 | 3/2004 | Hunter et al. | 424/426 |
| 2004/0063606 A1 | 4/2004 | Chu et al. | 514/1 |
| 2004/0117007 A1 | 6/2004 | Whitbourne et al. | 623/1.42 |

| | | | | | |
|---|---|---|---|---|---|
| 2005/0042240 A1 | 2/2005 | Utterberg et al. ............ 424/400 | WO | WO 02/087586 A1 | 11/2002 |
| 2005/0058673 A1 | 3/2005 | Scholz et al. ................. 424/401 | WO | 03/059408 A2 | 7/2003 |
| 2005/0080008 A1 | 4/2005 | White et al. ...................... 514/12 | WO | 2005/096990 A2 | 10/2005 |
| 2005/0089539 A1 | 4/2005 | Scholz et al. ................. 424/401 | | | |
| 2005/0147690 A1 | 7/2005 | Masters et al. ................ 424/499 | | | |
| 2005/0165342 A1 | 7/2005 | Odland ........................ 604/5.01 | | | |

OTHER PUBLICATIONS

| | | | |
|---|---|---|---|
| 2005/0220839 A1 | 10/2005 | DeWitt et al. ................ 424/423 |
| 2005/0220840 A1 | 10/2005 | DeWitt et al. ................ 424/423 |
| 2005/0220841 A1 | 10/2005 | DeWitt et al. ................ 424/423 |
| 2005/0220842 A1 | 10/2005 | DeWitt et al. ................ 424/423 |
| 2005/0220843 A1 | 10/2005 | DeWitt et al. ................ 424/423 |
| 2005/0232970 A1 | 10/2005 | Stucke et al. ................. 424/426 |
| 2005/0244453 A1 | 11/2005 | Stucke et al. ................. 424/426 |
| 2005/0244459 A1 | 11/2005 | DeWitt et al. ................ 424/426 |
| 2005/0255142 A1 | 11/2005 | Chudzik et al. .............. 424/426 |
| 2005/0256502 A1 | 11/2005 | DiMatteo et al. ............. 604/523 |
| 2005/0281857 A1 | 12/2005 | Heyer et al. .................. 424/423 |
| 2006/0024372 A1 | 2/2006 | Utterberg et al. ............ 424/488 |
| 2006/0030669 A1 | 2/2006 | Taton et al. ................... 525/242 |
| 2006/0051384 A1 | 3/2006 | Scholz et al. ................. 424/405 |
| 2006/0051385 A1 | 3/2006 | Scholz ......................... 424/405 |
| 2006/0052452 A1 | 3/2006 | Scholz ......................... 514/557 |
| 2006/0073207 A1 | 4/2006 | Masters et al. ................ 424/488 |
| 2006/0083772 A1 | 4/2006 | DeWitt et al. ................ 424/426 |
| 2006/0147491 A1 | 7/2006 | DeWitt et al. ................ 424/426 |
| 2006/0167531 A1 | 7/2006 | Gertner et al. .................. 607/86 |
| 2006/0195165 A1 | 8/2006 | Gertner et al. .................. 607/86 |
| 2006/0198868 A1 | 9/2006 | DeWitt et al. ................ 424/426 |
| 2006/0210816 A1 | 9/2006 | Finley ........................... 428/457 |
| 2006/0216324 A1 | 9/2006 | Stucke et al. ................. 424/422 |
| 2006/0259013 A1 | 11/2006 | Ranalletta et al. ............ 604/539 |
| 2006/0271000 A1 | 11/2006 | Ranalletta et al. ............ 604/263 |
| 2006/0271024 A1 | 11/2006 | Gertner et al. ..................... 606/2 |
| 2006/0276894 A1 | 12/2006 | Finley ........................ 623/11.11 |
| 2007/0059434 A1 | 3/2007 | Roorda et al. .................. 427/2.1 |
| 2007/0065481 A1 | 3/2007 | Chudzik et al. .............. 424/426 |
| 2007/0065482 A1 | 3/2007 | Chudzik et al. .............. 424/426 |
| 2007/0065483 A1 | 3/2007 | Chudzik et al. .............. 424/426 |
| 2007/0106261 A1 | 5/2007 | DiMatteo et al. ............. 604/523 |
| 2007/0249986 A1 | 10/2007 | Smego ............................. 604/8 |
| 2007/0255140 A1 | 11/2007 | Violante et al. ............... 600/458 |
| 2007/0259913 A1 | 11/2007 | Deitchman et al. ........... 514/303 |
| 2008/0045894 A1 | 2/2008 | Perchik et al. ............. 604/96.01 |
| 2008/0063627 A1 | 3/2008 | Stucke et al. ................. 424/93.7 |

FOREIGN PATENT DOCUMENTS

| | | |
|---|---|---|
| EP | 1113008 A1 | 7/2001 |
| EP | 1 155 689 A2 | 11/2001 |
| JP | 52-89680 A | 7/1977 |
| JP | 53-149985 A | 12/1978 |
| JP | 55-59173 A | 5/1980 |
| JP | 63-112530 | 5/1988 |
| WO | WO 91/07400 | 5/1991 |
| WO | 93/18751 | 9/1993 |
| WO | 94/26254 | 11/1994 |
| WO | WO 95/03036 A1 | 2/1995 |
| WO | WO 96/13286 | 5/1996 |
| WO | 96/30060 | 10/1996 |
| WO | 97/28156 | 8/1997 |
| WO | 98/12243 | 3/1998 |
| WO | 98/19713 | 5/1998 |
| WO | 98/24483 | 6/1998 |
| WO | 98/41154 | 9/1998 |
| WO | 99/07417 | 2/1999 |
| WO | 99/55396 | 11/1999 |
| WO | WO 99/55396 | 11/1999 |
| WO | 99/65538 | 12/1999 |
| WO | 00/09087 | 2/2000 |
| WO | 00/09088 | 2/2000 |
| WO | 00/09190 | 2/2000 |
| WO | 00/21584 A1 | 4/2000 |
| WO | 00/21842 | 4/2000 |
| WO | 00/33764 | 6/2000 |
| WO | 01/15526 | 3/2001 |
| WO | 01/17575 | 3/2001 |
| WO | WO 02/09768 A2 | 2/2002 |
| WO | WO 02/069949 A2 | 9/2002 |

Badawey et al., "Potential anti-microbials. I. Synthesis and structure-activity studies of some new thiazolo[4,5-*d*]pyrimidine derivatives," *Eur J Med Chem.*, 28:91-96, 1993.

Bean et al., "Inhibitory Effects and Metabolism of 5-Fluoropyrimidine Derivatives in Pneumococcus," *Journal of Bacteriology*, 106(2):412-420, May 1971.

Block et al., "Experimental Therapy of Cladosporiosis and Sporotrichosis with 5-Fluorocytosine," *Antimicrobial Agents and Chemotherapy*, 3(1):95-98, Jan. 1973.

Cohen et al., "The Mode of Action of 5-Fluorouracil and its Derivatives," *Proc. Nat. Acad. Sci.*, 44:1004-1012, 1958.

El-Sherbeny et al., "Synthesis of Some New Thiazolo[4,5-d]Pyrimidine Derivatives and Evaluation of Their Antifungal, Antiviral and Cytotoxic Activities," *Medicinal Chemistry Research*, 6:28-39, 1996.

Ghosh et al., "2,4-Bis(arylamino)-5-methylpyrimidines as Antimicrobial Agents," *J Med. Chem.*, 10:974-975, Sep. 1967.

Holmes et al., "Viability of microorganisms in fluorouracil and cisplatin small-volume injections," *American Journal of Hospital Pharmacy*, 45:1089-91, May 1988.

Holt et al., "The antimycotic activity of 5-fluorocytosine," *J. Clin. Path.*, 26: 167-74, 1973.

Kesavan et al., "5-Fluorouracil Altered Morphology and Inhibited Growth of *Candida albicans*," *Journal of Clinical Microbiology*, 43(12):6215-6216, Dec. 2005.

Linguist et al., "5-Fluorocytosine in the Treatment of Experimental Candidiasis in Immunosuppressed Mice," *Antimicrobial Agents and Chemotherapy*, 4(1):58-61, Jul. 1973.

Louie et al., "Efficacies of High-Dose Fluconazole plus Amphotericin B and High-Dose Fluconazole plus 5-Fluorocytosine versus Amphotericin B, Fluconazole, and 5-Fluorocytosine Monotherapies in Treatment of Experimental Endocarditis, Endophthalmitis, and Pyelonephritis Due to *Candida albicans*," *Antimicrobial Agents and Chemotherapy*, 43(12):2831-2840, Dec. 1999.

Martin et al., "In vitro Susceptibility of 245 Yeast Isolates to Amphotericin B, 5-Fluorocytosine, Ketoconazole, Fluconazole and Itraconazole," *Chemotherapy*, 38:335-339, 1992.

McCaffery J., "Studies in the Toxicity and Clinical Application of 5-Fluorouracil," *The Medical Journal of Australia*, (2):582-585, Oct. 10, 1964.

Nsanzumuhire et al., "Chromomycosis Due to *Cladosporium trichoides* Treated with 5-Fluorocytosine," *Am J. Clinical Pathology*, 61:257-263, Feb. 1974.

Perez-Blanco et al., "Ajoene and 5-fluorouracil in the topical treatment of *Cladophialophora carrionii* chromoblastomycosis in humans: a comparative open study," *Medical Mycology*, 41:517-520, 2003.

Pittillo et al., "Chemotherapeutic Activity of 5-Fluorocytosine Against a Lethal *Candida albicans* Infection in Mice," *Applied Microbiology*, 17(5):773-774, May 1969.

Polak, A., "Mode of Action of 5-Fluorocytosine and 5-Fluorouracil in Dematiaceous Fungi," *Sabouraudia*, 21:15-25, 1983.

Rauckman et al., "2,4-Diamino-5-benzylpyrimidines and Analogues as Antibacterial Agents, 10. 2,4-Diamino-5-(6-quinolylmethyl)- and —[(tetrahydro-6-quinolypmethyl]pyrimidine Derivatives. Further Specificity Studies." *J. Med. Chemotherapy*, 32(8):1927-1935, 1989.

Rival et al., "Antifungal activity in vitro of some imidazo[1,2-*a*]pyrimidine derivatives," *Eur J Med. Chem.* 26(1):13-18, 1991.

Shadomy et al., "In Vitro Activity of 5-Fluorocytosine Against *Candida* and *Torulopsis* Species," *Antimicrobial Agents and Chemotherapy*, 3(1):9-14, Jan. 1973.

Stavorovsky et al., "*Candida* Sepsis Successfully Treated by Parental Administration of 5-Fluorocytosine," *International Surgery*, 61(8):426-429, Aug. 976.

Tomasz et al., "The Mechanism of Bacterial Fragility Produced by 5-Flourouracil: The Accumulation of Cell Wall Precursors," *Proc. Nat. Acad. Sci.*, vol. 46:324-327, 1960.

Wagner et al., "Effects of Purines and Pyrimidines on the Fungistatic Activity of 5-Fluorocytosine in *Aspergillus* Species," *Antimicrobial Agents and Chemotherapy*, 11(2):229-233, Feb. 1977.

Waldorf et al., "Mechanisms of Action of 5-Fluorocytosine," *Antimicrobial Agents and Chemotherapy*, 23(1):79-85, Jan. 983.

Wang et al., "Expression of Human Mitochondrial Thymidine Kinase in *Escherichia coli*: Correlation between the Enzymatic Activity of Pyrimidine Nucleoside Analogues and Their Inhibitory Effect on Bacterial Growth," *Biochemical Pharmacology*, 59:1583-1588, 2000.

Basaki et al., "UFT and Its Metabolites Inhibit Cancer-Induced Angiogenesis via a VEGF—Related Pathway," *Oncology*, 14(10): 68-71, 2000.

Wendling et al., "5-Fluorouracil Blocks Transforming Growth Factor-β-Induced $\alpha_2$ Type I Collagen Gene (*COLIA2*) Expression in Human Fibroblasts via c-Jun $NH_2$-Termin Kinase/Activator Protein-1 Activation," *Molecular Pharmacology*, 64(3):707-713, 2003.

Hentzer, Morten et al., "Inhibition of quorum sensing in *Pseudomonas aeruginosa* biofilm bacteria by a halogenated furanone compound," *Microbiology* 148:87-102, 2002.

Hussain, M. et al., "Radiochemical assay to measure the biofilm produced by coagulase-negative staphylococci on solid surfaces and its use to quantitate the effects of various antibacterial compounds on the formation of the biofilm" *J. Med. Microbiol.* 37:62-69, 1992.

Ren, Dacheng et al., "Brief report. Inhibition of biofilm formation and swarming of *Escherichia coli* by (5Z)-4-bromo-5-(bromomethylene)-3-butyl-2(*5H*)-furanone," *Environmental Microbiology* 3(11):731-736, 2001.

Alkan-Onyuksel, H. et al., "A Mixed Micellar Formulation Suitable for the Parenteral Administration of Taxol," *Pharmaceutical Research* 11(2): 206-212, Feb. 1994.

Allison, David G., et al., "Biofilms: problems of control," *SGM Symposium* 59: 309-327, 2000.

Anai, H. et al., "Sensitivity test for 5-Fluorouracil and Its Analogues, 1-(2-Tetrahydrofuryl)-5-Fluorouracil, Uracil/1-(2-Tetrahydrofuryl)-5-Fluorouracil (4:1) and 1-Hexylcarbamoyl-5-Fluorouracil, Using the Subrenal Capsule Assay," *Oncology* 45: 144-147, 1988.

Arcamone, F. et al., "Doxorubicin Disaccharide Analogue: Apoptosis-Related Improvement of Efficasy in Vivo," *Journal of the National Cancer Institute* 89(16): 1217-1223, Aug. 20, 1997.

Arshady, R., "Preparation of Biodegradable Microspheres and Microcapsules: 2. Polylactides and related polyesters," *Journal of Controlled Release* 17: 1-22, 1991.

Bartoli et al., "In vitro and in vivo antitumoral activity of free, and encapsulated taxol," *J. Microencapsulation* 7(2): 191-197, 1990.

Bassetti, Stefano, et al., "Prolonge Antimicrobial Activity of a Catheter Containing Chlorhexidine-Silver Sulfadiazine Extends Protection against Catheter Infections in Vivo," *Antimicrobial Agents and Chemotherapy* 45(5):1535-1538, May 2001.

Bawa et al., "An Explanation for the Controlled Release of Macromolecules from Polymers," *Journal of Controlled Release* 1:259-267, 1985.

Bazile, D. et al., "Stealth Me.PEG-PLA Nanoparticles Avoid Uptake by the Mononuclear Phagocytes System," *Journal of Pharmaceutical Sciences* 84(4):493-498, Apr. 1995.

Bérubé and Lepage, "Unexpected Transesterification of N-(trifluoroacetyl) Doxorubicin with Acetylsalicylic Acid: Formation of 4'-O-Acetyl-N-(Trifluoroacetyl) Doxorubicin," *Synthetic Communications* 28(6): 1109-1116, 1998.

Bodet, C. A. et al., "Antibacterial Activities of Antineoplastic Agents," *Antimicrobial Agents and Chemotherapy*, 28(3): 437-439, Sep. 1985.

Bollag and Harmann, "Tumor Inhibitory Effects of a New Fluorouracil Derivative: 5'-Deoxy-5-Fluorouridine," *European Journal of Cancer 16*: 427-432, 1280.

Brown et al., "In Vivo and in Vitro Release of Macromolecules from Polymeric Drug Delivery Systems," *Journal of Pharmaceutical Sciences* 72(10): 1181-1185, 1983.

Brun-Buisson, Christian, et al., "Prevention of intravascular catheter-related infection with newer chlorhexidine-silver sulfadiazine-coated catheters: a randomized controlled trial," *Intensive Care Med.* 30:837-843, 2004.

Burke, Kathryn, "Combating phlebitis: a peripheral cannula grading scale," *Nursing Times* 96(29):38-39, Jul. 2000.

Cascone et al., "Collagen and hyaluronic acid based polymeric blends as drug delivery systems for the release of physiological concentrations of growth hormone," *Journal of Materials Science: Materials in Medicine* 5: 770-774, 1994.

Cassinelli, G. et al., "13-Deoxycarminomycin, a New Biosynthetic Anthracycline," *Journal of Natural Products* 48(3): 435-439, May-Jun. 1985.

Cohen, Seymour S., et al., "Studies on Unbalanced Growth in *Escherichia coli*," *Biochemistry* 40:885-893, 1954.

Cohen, Seymour S., et al., "The Mode of Action of 5-Fluorouracil and its Derivatives," *Biochemistry* 44:1004-1012, 1958.

Costerton, J.W., et al, "Bacterial Biofilms: A Common Cause of Persistent Infections," *Science* 284:1318-1322, May 21, 1999.

Cragg, Andrew H., et al., "Effect Antiineoplastic Agents on Smooth Muscle Cell Proliferation in Vitro: Implications for Prevention of Restenosis after Transluminal Angioplasty," *Journal of Vascular and Interventional Radiology* 3(2):273-277, May 1992.

Cserháti and Holló, "Interaction of taxol and other anticancer drugs with hydroxypropyl-β-cyclodextrin," *International Journal of Pharmaceutics* 108: 69-75, 1994.

Darouiche, Rabih O., et al., "A Comparison of Two Antimicrobial-Impregnated Central Venous Catheters," *The New England Journal of Medicine* 340(1):1-8, Jan. 7, 1999.

Dias, A.A., "Materials: The Evolving Functionalities of Coatings," *Medical Device Link*, downloaded on Feb. 15, 2008, available at http://www.devicelink.com.

Dickinson, Gordon M., et al., "Minireviews: Infections Associated with Indwelling Devices: Concepts of Pathogenesis; Infections Associated with Intravascular Devices," *Antimicrobial Agents and Chemotherapy* 33(5):597-601, May 1989.

Dimick, Justin B., et al., "Increased Resource Use Associated with Catheter-Related Bloodstream Infection in the Surgical Intensive Care Unit," *Arch Surg.* 136:229-234, Feb. 2001.

Donlan, Rodney M., "Biofilms and Device-Associated Infections," *Emerging Infectious Diseases* 7(2):277-281, Mar.-Apr. 2001.

Dunn, E.J. et al., "Synthesis of *N*-(aminoalkyl)chitosan for Microcapsules," *Journal of Applied Polymer Science* 50(2): 353-365, Oct. 10, 1993.

Falchi, M. et al., "Antibacterial and Cytotoxic Effect of Ceftazidime-Mitoxantrone Association," *Anticancer Researcher* 9(2): 291-292, 1989.

Farr, Barry M., "Preventing Vascular Catheter-Related Infections: Current Controversies," *Healthcare Epidemiology CID* 33:1733-1738, Nov. 15, 2001.

Galliani, S. et al., "Chemiluminescence Response of Human Neutrophils to *S. epidermidis* Adherent to i.v. Catheters: Influence of Strain Polymer, Proteins and Chemotherapy," *Abstracts of the 94th General Meeting of the American Society for Microbiology*, p. 70, Abstract No. B-231, 1994.

Galliani, S. et al., "Influence of strain, biomaterial, proteins, and oncostatic chemotherapy on *Staphylococcus epidermidis* adhesion to intravascular catheters in vitro," *The Journal of Laboratory and Clinical Medicine* 127(1): 71-80, Jan. 1996.

Gieringer, J.H. et al., "Effect of 5-Fluorouracil, Mitoxantrone, Methotrexate, and Vincristine on the Antibacterial Activity of Ceftriaxone, Ceftazidime, Cefotiam, Piperacillin, and Netilmicin," *Chemotherapy* 32(5): 418-424, 1986.

Goldschmidt et al., "Effect of chemotherapeutic agents upon microorganisms isolated from cancer patients," Antimicrobial Agents and Chemotherapy 1(4): 348-353, AprilF0.

Gómez, J.A. et al., "Synthesis of Novel-5-Fluorouracil Derivatives with 1,4-Oxaheteroepane Moieties," *Tetrahedron* 54(43):13295-13312, 1998.

Goodell, J.A. et al., "Preparation and release characteristics of tobramycin-impregnated polymethylmethacrylate," *American Journal of Hospital Pharmacy* 43(6): 1454-1461, Jun. 1986.

Goodman and Gilman Editors. "The Pharmacological Basis of Therapeutics," Eighth Edition, New York, Pergamon Press, 1227-1230, 1990.

Gref, R. et al., "Biodegradably Long-Circulating Polymeric Nanospheres," *Science* 263:1600-1603, Mar. 18, 1994.

Hagen et al., "PLA-PEG Micelles—A Novel Drug Delivery System," *Proceed. Intern. Symp. Control. Rel. Bioact. Mater.* 22, Controlled Release Society, 1995, pp. 194-195.

Hamilton-Miller, "Antimicrobial activity of 21 anti-neoplastic agents," *The British Journal of Cancer* 49:367-369, 1984.

Heard, Stephen O., et al., Influence of Triple-Lumen Central Venous Catheters Coated with Chlorhexidine and Silver Sulfadiazine on the Incidence of Catheter-Related Bacteremia, *Arch Intern Med* 158:81-87, Jan. 12, 1998.

Hellmann, Mathias, et al., "Fibronectin, Fibrinogen, and Laminin Act as Mediators of Adherence of Clinical Staphylococcal Isolates to Foreign Material," *The Material of Infectious Diseases* 158(4):693-701, Oct. 1988.

Herrmann, Mathias, et al., "Interaction of von Willebrand Factor with *Staphylococcus aureus*," *The Journal of Infectious Diseases* 176:984-991, 1997.

Holland et al., "Polymers for Biodegradably Medical Devices. 1. The Potential of Polyesters as Controlled Macromolecular Release Systems," *Journal of Controlled Release* 4: 155-180, 1986.

Hoshi, A. et al., "Antitumor Activity of Metabolites of 1-Hexylcarbamoyl-5-fluorouracil and Related Compounds Against L 1210 Leukemia In Vivo and L5178Y Lymphoma Cells In Vitro," *Journal of Pharmacobio-Dynamics* 3(9): 478-481, Sep. 1980.

Hronowski and Szarek, "Synthesis of cyclopentane analo s of 5-fluorouracil nucleosides," *Canadian Journal of Chemistry* 70(4): 1162-1169, Apr. 1992.

Hugonnet, Stéphane, et al., "Nosocomial Bloodstream Infection and Clinical Sepsis," *Emerging Infectious Diseases* 10(1):76-81, Jan. 2004.

Hunt, Dale E., et al., "Killing of Cells in Bacterial Colonies," *Applied Microbiology* 15(2):334-339, Mar. 1967.

Hunter et al., "Anti-Angiogenic Compositions and Methods of Use," U.S. Appl. No. 10/389,261, filed Mar. 13, 2003.

Hunter et al., "Anti-Angiogenic Compositions and Methods of Use," U.S. Appl. No. 10/390,534, filed Mar. 14, 2003.

Ingrams, Duncan R., et al., "Does slow-release 5-fluorouracil and triamcinolone reduce subglottic stenosis?" *Archives of Otolaryngology Head & Neck Surgery* 118(2): 174-177, Feb. 1998.

Jaeger, K., et al., "Reduction of catheter-related infections in neutropenic patients: a prospective controlled randomized trial using a chlorhexidine and silver sulfadiazine-impregnated central venous catheter," *Ann Hematol* 84:258-262, 2005.

Jampel et al., "Glaucoma Filtration Surgery in Nonhuman Primates Using Taxol and Etoposide in Polyanhydride Carriers," *Investigative Ophthalmology & Visual Science* 34(11): 3076-3083, 1993.

Kim, B.S. et al., "Structure Elucidation and Antifungal Activity of an Anthracycline, Antibiotic, Daunomycin, Isolated from *Actinomadura roseola*," *Journal of Agricultural and Food Chemistry* 48(5): 1875-1881, 2000.

Kozai, S. et al., "A new method for the synthesis of $N^3$-alkylated analogs of 5-fluorouracil," *J. Chem. Soc., Perkin Transactions* 1(19): 3145-3146, Oct. 7, 1998.

Kwon et al., "Biodistribution of Micelle-Forming Polymer-Drug Conjugates," *Pharmaceutical Research* 10(7): 970-974, 1993.

Kwon et al., "Physical Entrapment of Adriamycin in AB Block Copolymer Micelles," *Pharmaceutical Research* 12(2): 192-195, 1995.

Langer and Folkman, "Controlled Release of Macromolecules from Polymers," in *Biomedical Polymers. Polymeric Materials and Pharmaceuticals for Biomedical Use*, Goldberg and Nakajime (eds), Academic Press, New York, 1980, pp. 113-137.

Levowitz, B.S. et al., "Biologic Compatibility and Applications of Hydron," *Transactions. American Society for Artificial Internal Organs* 14:82-88, 1968.

Li, Y-X. et al., "Cytotoxic Interactions of 5-Fluoroouracil and Nucleoside Analogues in Vitro," *Anticancer Research* 17(1A): 21-28, Jan.-Feb. 1997.

Machan et al., "Stent Grafts with Bioactive Coatings," U.S. Appl. No. 09/476,490, filed Dec. 30, 1999.

Maddox, Ray R., et al., "Double-blind study to investigate methods to prevent cephalothin-induced phlebitis," *Am J Hosp Pharm* 34:29-34, Jan. 1977.

Maehara, Y. et al., "UFT is More Antineoplastic against Gastric Carcinoma than 5-Fluorouracil, 1-(2-Tetrahydrofuryl)-5-fluorouracil and 1-Hexylcarbamoyl-5-Fluorouracil," *Chemotherapy* 34(6): 484-489, Nov.-Dec. 1988.

Maki, Dennis G., et al., "A Semiquantitative Culture Method for Identifying Intravenous-Catheter-Related Infection," *The New England Journal of Medicine* 296(23):1305-1309, Jun. 9, 1977.

Maki, Dennis G., et al., "An Attachable Silver-Impregnated Cuff for Prevention of Infection with Central Venous Catheters: A Prospective Randomized Multicenter Trial," *The American Journal of Medicine* 85:307-314, Sep. 1988.

Maki, Dennis G., et al., "Prevention of Central Venous Catheter-Related Bloodstream Infection by Use of an Antiseptic-Impregnated Catheter," *Annals of Internal Medicine* 127(4):257-266, Aug. 15, 1997.

Maki, D.G., et al., "Clinical Trial of a Novel Antiseptic Central Venous Catheter," *American Society for Microbiology* 57(8):176, Oct. 1, 1991 (abstract).

Marshall, John L., et al., "An Alternate Method to Overcoming Central Venous Catheter Blockage in Patients Receiving High-Dose Fluorouracil and Leucovorin," *J Clin Oncol.* 11(7):1433-1434, Jul. 1993.

Matsuura, A. et al., "General Pharmacological Properties of Doxifluridine, A New Fluorouracil Derivative," *Oyo Yakuri* 29(5): 803-831, 1985.

Mermel, Leonard A., et al., "Guidelines for the Management of Intravascular Catheter-Related Infections," *Management Guidelines for Catheter Infections* 32:1249-1272, May 1, 2001.

Miwa, M. et al., "Comparative Studies on the Antitumor and Immunosuppressive Effects of the New Fluorouracil Derivative N4-Trimethoxybenzoyl-5'-deoxy-5-fluorocytidine and Its Paretn Drug 5'-Deoxy-5-fluorouridine," *Chemical & Pharmaceutical Bulletin* 38(4): 998-1003, Apr. 1990.

Miyazaki, S. et al., "Drug release from oral mucosal adhesive tablets of chitosan and sodium alginate," *International Journal of Pharmaceutics* 118(2): 257-263, May 1995.

Monteagudo, E. et al., "Conformational analysis of 4-demethoxy-7-$O$-[2,6-dideoxy-4-$O$-(2,3,6-trideoxy-3-amino-$\alpha$-L-*lyxo*-hexapyranosyl)-$\alpha$-L-*lyxo*-hexopyranosyl]adriamicinone, the first doxorubicin disaccharide analogue to be reported," *Carbohydrate Research* 300:11-16, 1997.

Morales, Manuel, et al., "Biofilm: the microbial "bunker" for intravascular catheter-related infection," *Support Care Cancer* 12:701-707, 2004.

Nagy, A. et al., "Synthesis and biological evaluation of cytotoxic analogs of somatostatin containing doxorubicin or its intensely potent derivative, 2-pyrrolinodoxorubicin," *Proc. Natl. Acad. Sci. USA* 95: 1794-1799, Feb. 1998.

Okada, T., "Anti-Tumor Activities of 1-Acetyl-3-o-Toluyl-5-Fu," *Hiroshima Journal of Medical Sciences* 28(1-4): 49-66, 1979.

*Physician's Desk Reference (PDR)*, Thomson PDR, 52nd edition, Nov. 1997, pp. 2463-2464.

*Physician's Desk Reference (PDR) Electronic Library*, Carac Cream, 0.5% (Dermik), 59th Edition, 2005.

Pitt, C., "The controlled parenteral delivery of polypeptides and proteins," *International Journal of Pharmaceutics* 59: 173-196, 1990.

Prajda, N. et al., "Comparison of Tumor Growth Inhibitory and Toxic Effects of a New Fluorouracil—Nitrosourea Derivative (B-3839)," in vivo 2: 151-154, 1988.

Pratesi, G. et al., "Improved Efficacy and Enlarged Spectrum of Activity of a Novel Anthracycline Disaccharide Analogue of Doxorubicin against Human Tumor Xenografts," *Clinical Cancer Research* 4: 2833-2839, Nov. 1998.

Quaglia, M.G. et al., "Analysis of a New Doxorubicin Derivative (FCE 23762) and Related Compounds by High Performance Capillary Electrophoresis," *Journal of Liquid Chromatography* 17(18): 3911-3923, 1994.

Raad, Issam, et al., "Ultrastructural Analysis of Indwelling Vascular Catheters: A Quantitative Relationship between Luminal Colonization and Duration of Placement," *The Journal of Infectious Diseases 168*:400-407, Aug. 1993.

Raad, Issam, et al., "The Broad-Spectrum Activity and Efficacy of Catheters Coated with Minocycline and Rifampin," *The Journal of Infectious Diseases 173*:418-424, Feb. 1996.

Raad, Issam, et al., "Differential Time to Positivity: A Useful Method for Diagnosing Catheter-Related Bloodstream Infections," *Annals of Internal Medicine 140*(1):18-26, Jan. 6, 2004.

Rapoport, N.Y. et al., "Micellar delivery of doxorubicin and its paramagnetic analog, ruboxyl, to HL-60 cells: effect of micelle structure and ultrasound on the intracellular drug uptake," *Journal of Controlled Release 58*: 153-162, 1999.

Rello, Jordi, et al., "Evaluation of Outcome of Intravenous Catheter-related Infections in Critically Ill Patients," *Am J Respir Crit Care Med 162*:1027-1030, 2000.

Rhine et al., "Polymers for Sustained Macromolecule Release: Procedures to Fabricate Reproducible Delivery Systems and Control Release Kinetics," *Journal of Pharmaceutical Sciences 69*(3): 265-270, 1980.

Rijnders, Bart J.A., et al., "Catheter-Tip Colonization as a Surrogate End Point in Clinical Studies on Catheter-Related Bloodstream Infection: How Strong is the Evidence?" *Clinical Infectious Diseases 35*:1053-1058, Nov. 1, 2002.

Sharma and Straubinger, "Novel taxol formulations: preparation and characterization of taxol-containing liposomes," *Pharm. Res. 11*(6): 889-896, 1994.

Sharma, A. et al., "Antitumor Effect of Taxol-containing Liposomes in a Taxol-resistant Murine Tumor Model," *Cancer Research 53*: 5877-5881, Dec. 15, 1993.

Sheep, Robert E., et al., "Fatal Cardiac Tamponade: Occurrence With Other Complications After Left Internal Jugular Vein Catheterization," *JAMA 248*(13):1632-1635, Oct. 1, 1982.

Sherertz, Robert J., et al., "Three-Year Experience with Sonicated Vascular Catheter Cultures in a Clinical Microbiology Laboratory," *Journal of Clinical Microbiology 28*(1):76-82, Jan. 1990.

Sherertz, Robert J., et al., "Efficacy of Antibiotic-Coated Catheters in Preventing Subcutaneous *Staphylococcus aureus* Infection in Rabbits," *The Journal of Infectious Diseases 167*:98-106, Jan. 1993.

Shiraishi, S. et al., "Controlled-release preparation of indomethacin using calcium alginate gel," *Biol. Pharm. Bull. 16*(11): 1164-1168, Nov. 1993.

Sigma-Aldrich, Inc., Product Information, 5-Fluorouracil.

Suzuki, S. et al., "A Proposed Mechanism for the Selective Inhibition of Human Cytopmegalovirus Replication by 1-(2'-Deoxy-2'-fluoro-β-D-arabinofuranosyl)-5-fluorouracil," *Molecular Pharmacology 31*(3): 301-306, Mar. 1987.

Tarr, B.D. et al., "A New Parenteral Emulision for the Administration of Taxol," *Pharmaceutical Research 4*(2): 162-165, Apr. 1987.

Tennenberg, Steven, et al., "A Prospective Randomized Trial of an Antibiotic-and Antiseptic-Coated Central Venous Catheter in the Prevention of Catheter-Related Infections," *Arch Surg 132*:1348-1351, Dec. 1997.

Thacharodi and Rao, "Collogen-chitosan composite membranes for controlled release of propranolol hydrochloride," *Intern. Journal of Pharmaceuticals 120*(1): 115-118, Jun. 1995.

Van der Wilt, C.L. et al., "In vitro antitumour activity of *cis*- and *trans*-5-fluoro-5,6-dihydro-6-alkoxy-uracils; effects on thymidylate synthesis," *British Journal of Cancer 68*: 702-707, 1993.

Veenstra, David L., et al., "Cost-Effectiveness of Antiseptic-Impregnated Central Venous Catheters for the Prevention of Catheter-Related Bloodstream Infection," *JAMA 282*(6):554-560, Aug. 11, 1999.

Veenstra, David L., et al., "Efficacy of Antiseptic-Impregnated Central Venous Catheters in Preventing Catheter-Related Bloodstream Infection," *JAMA 281*(3):261-267, Jan. 20, 1999.

von Eiff, Christof, et al., "Infections Associated with Medical Devices: Pathogenesis, Management and Prophylaxis," *Drugs 65*(2):179-214, 2005.

Walter et al., "Interstitial Taxol Delivered from a Biodegradable Polymer Implant against Experimental Malignant Glioma," *Cancer Research 54*: 2207-2212, 1994.

Yokoyama et al., "Improved synthesis of adriamycin-conjugated poly(ethylene oxide)-poly(aspartic acid) block copolymer and formation of unimodal micellar structure with controlled amount of physically entrapped adriamycin," *Journal of Controlled Release 32*: 269-277, 1994.

Zhang, J-R. et al., "Detection of Metabolites of a Fluorouracil Derivative A-OT-Fu," *Chinese Journal of Pharmaceuticals 20*(11): 513-515, 1989.

Zou, Y. et al., "Quantitative Analysis of the Lipophilic Doxorubicin Analogue Annamycin in Plasma and Tissue Samples by Reversed-Phase Chromatography," *Journal of Pharmaceutical Sciences 82*(11): 1151-1154, Nov. 1993.

Patent Abstracts of Japan, JP 52-089680, Jul. 27, 1977.

Patent Abstracts of Japan, JP 53-149985, Dec. 27, 1978.

Patent Abstracts of Japan, JP-55-059173, May 2, 1980.

Morales, Manuel, et al., "Biofilms the microbial "bunker" for intravascular catheter-related infection," *Support Care Cancer 12*:701-707, 2004.

Castelli, M., et al., "Bactericidal and Cytotoxic Effect of Combination of Norfloxacin and 5-Fluorouracil," *Anticancer Research 9*:49-52, 1989.

Effect of palmitic acid on the release profile of 5-fluorouracil from a polyurethane sample

COMPOSITIONS AND METHODS FOR COATING MEDICAL IMPLANTS

CROSS-REFERENCE TO RELATED APPLICATION

This application is a continuation-in-part of U.S. patent application Ser. No. 10/447,309, filed May 27, 2003, now pending, which application claims the benefit under 35 U.S.C. §119(e) of U.S. Provisional Patent Application No. 60/383,419, filed May 24, 2002, where these applications are incorporated herein by reference in their entireties.

BACKGROUND OF THE INVENTION

1. Field of the Invention

The present invention relates generally to pharmaceutical compositions, methods, and devices, and more specifically, to compositions and methods which reduce the likelihood of an infection associated with a medical implant.

2. Description of the Related Art

Infections associated with medical implants represent a major healthcare problem. For example, 5% of patients admitted to an acute care facility develop a hospital acquired infection. Hospital acquired infections (nosocomial infections) are the 11$^{th}$ leading cause of death in the US and cost over $2 billion annually. Nosocomial infections directly cause 19,000 deaths per year in the US and contribute to over 58,000 others.

The four most common causes of nosocomial infections are: urinary tract infection (28%); surgical site infection (19%); respiratory tract infection (17%); and bloodstream infection (16% and rising). A significant percentage of these infections are related to bacterial colonization of implanted medical implants such as Foley catheters (urinary tract infections); surgical drains, meshes, sutures, artificial joints, vascular grafts (wound infections); endotracheal and tracheostomy tubes (respiratory tract infection); and vascular infusion catheters (bloodstream infections). Although any infectious agent can infect medical implant, Staphylococci (*S. aureus, S. epidermidis, S. pyogenes*), Enterococci (*E. coli*), Gram Negative Aerobic Bacilli, and *Pseudomonas aeruginosa* are common causes. Once a medical implant becomes colonized by bacteria, it must frequently be replaced resulting in increased morbidity for the patient and increased cost to the healthcare system. Often the infected device serves as a source for a disseminated infection which can lead to significant morbidity or even death.

In an attempt to combat this important clinical problem, devices have been coated with antimicrobial drugs. Representative examples include U.S. Pat. No. 5,520,664 ("Catheter Having a Long-Lasting Antimicrobial Surface Treatment"), U.S. Pat. No. 5,709,672 ("Silastic and Polymer-Based Catheters with Improved Antimicrobial/Antifungal Properties"), U.S. Pat. No. 6,361,526 ("Antimicrobial Tympanostomy Tubes"), U.S. Pat. No. 6,261,271 ("Anti-infective and antithrombogenic medical articles and method for their preparation"), U.S. Pat. No. 5,902,283 ("Antimicrobial impregnated catheters and other medical implants") U.S. Pat. No. 5,624,704 ("Antimicrobial impregnated catheters and other medical implants and method for impregnating catheters and other medical implants with an antimicrobial agent") and U.S. Pat. No. 5,709,672 ("Silastic and Polymer-Based Catheters with Improved Antimicrobial/Antifungal Properties").

One difficulty with these devices, however, is that they can become colonized by bacteria resistant to the antibiotic coating. This can result in at least two distinct clinical problems. First, the device serves as a source of infection in the body with the resulting development of a local or disseminated infection. Secondly, if an infection develops, it cannot be treated with the antibiotic(s) used in the device coating. The development of antibiotic-resistant strains of microbes remains a significant healthcare problem, not just for the infected patient, but also for the healthcare institution in which it develops.

Thus, there is a need in the art for medical implants which have a reduced likelihood of an associated infection. The present invention discloses such devices (as well as compositions and methods for making such devices) which reduce the likelihood of infections in medical implants, and further, provides other, related advantages.

BRIEF SUMMARY OF THE INVENTION

Figure 1:
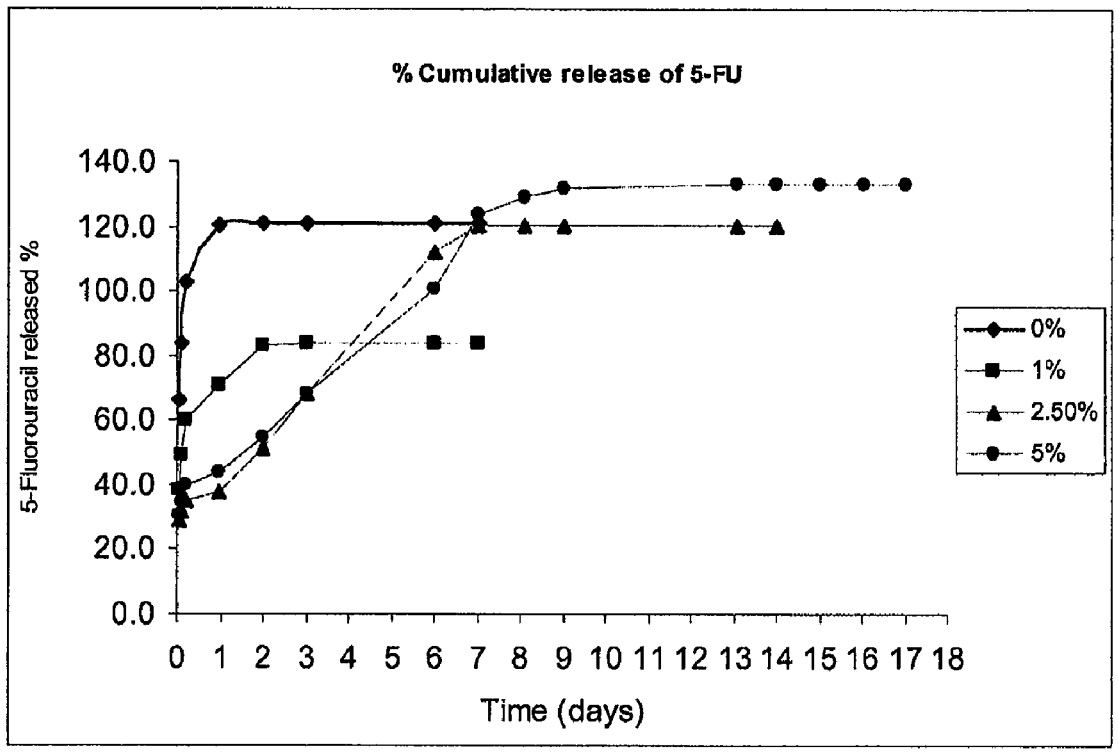
FIG. 1 shows the effect of palmitic acid on the release profile of 5-fluorouracil from a polyurethane sample.

Briefly stated, the present invention provides compositions and methods for preventing, reducing or inhibiting the likelihood of infections associated with medical implants. More specifically, within one aspect of the invention medical implants or devices are provided which release a chemotherapeutic agent, wherein the chemotherapeutic agent reduces, inhibits, or prevents the growth or transmission of foreign organisms (e.g., bacteria, fungi, or viruses) which are on or are associated with the medical device or implant. For example, within one aspect of the invention medical implant or devices are provided which release a fluoropyrimidine or an analog thereof. Within various embodiments, the implant is coated in whole or in part with a composition comprising a fluoropyrimidine or an analog thereof.

Other aspects of the present invention provide methods for making medical implants, comprising adapting a medical implant (e.g., coating the implant) with a fluoropyrimidine or an analog thereof. Within certain embodiments, the fluoropyrimidine or an analog thereof is coated on and/or released from the medical implant at a dosage and/or concentration which is less than the typical dosage and/or concentration of the fluoropyrimidine or analog thereof when used in the treatment of cancer.

A wide variety of medical implants can be generated using the methods provided herein, including, for example, catheters (e.g., vascular and dialysis catheters), heart valves, cardiac pacemakers, implantable cardioverter defibrillators, grafts (e.g., vascular grafts), ear, nose, or throat implants, urological implants, endotracheal or tracheostomy tubes, CNS shunts, orthopedic implants, and ocular implants. Within certain embodiments, the catheter (e.g., vascular and dialysis catheters), heart valve, cardiac pacemaker, implantable cardioverter defibrillator, graft (e.g., vascular grafts), ear, nose, or throat implant, urological implant, endotracheal or tracheostomy tube, CNS shunt, orthopedic implant, or ocular implant releases a fluoropyrimide (e.g., 5-FU) or an analog thereof at a dosage and/or concentration which is less than a typical dosage and/or concentration which is used for the treatment of cancer.

Within further aspects of the invention, there is provided a catheter which releases a fluoropyrimidine or an analog thereof. In one embodiment, the catheter releases 5-FU. In other embodiments, the catheter further comprises a polymer wherein the agent is released from a polymer on the catheter. In certain embodiments, the catheter has a polymer that is a polyurethane, cellulose or a cellulose-derived polymer (e.g., nitrocellulose), or a combination of polyurethane and cellulose or a cellulose-derived polymer. In related embodiments, the catheter is a vascular catheter (e.g., a central venous catheter, a peripheral intravenous catheter, an arterial line or transducer, or a port-catheter) or a dialysis catheter (e.g., a hemodialysis catheter or peritoneal dialysis catheter). In still other embodiments, the catheter releases a fluoropyrimidine or its analog that is present on the catheter at a concentration which is less than the typical dosage and/or concentration that is used in the treatment of cancer.

Within further aspects of the invention, there is provided a tube which releases a fluoropyrimidine or an analog thereof. In one embodiment, the tube releases 5-FU. In other embodiments, the tube further comprises a polymer wherein the agent is released from a polymer on the tube. In certain embodiments, the tube has a polymer that is a polyurethane, cellulose or a cellulose-derived polymer (e.g., nitrocellulose), or a combination of polyurethane and cellulose or a cellulose-derived polymer. In related embodiments, the tube is a drainage tube or nasgastric tube. In still other embodiments, the tube releases a fluoropyrimidine or an analog thereof that is present on the catheter at a concentration which is less than the typical dosage and/or concentration that is used in the treatment of cancer.

Within other aspects of the invention, a composition is provided that comprises one or more polymers and a fluoropyrimidine or an analog thereof, wherein the composition is in the form of a coating on a medical implant, and wherein the coated medical implant releases the fluoropyrimidine or analog thereof in an amount effective in reducing or inhibiting bacterial infection in an in vitro radial diffusion assay. In certain embodiments, the composition further comprises one or more polymers, such as a polyurethane, cellulose or a cellulose-derived polymer, a combination of a polyurethane and cellulose or a cellulose-derived polymer. In certain embodiments, the fluoropyrimidine is 5-fluorouracil.

Also provided methods for reducing or inhibiting infection associated with a medical implant, comprising the step of introducing a medical implant into a patient which has been coated with a fluoropyrimidine or an analog thereof. In certain embodiments, the fluoropyrimidine is 5-fluorouracil. Within further embodiments, the medical implant further comprises a polymer, such as a polyurethane, cellulose or a cellulose-derived polymer, or a combination of a polyurethane and cellulose or a cellulose-derived polymer.

These and other aspects of the present invention will become evident upon reference to the following detailed description and attached drawings. In addition, various references are set forth herein which describe in more detail certain procedures or compositions (e.g., compounds or agents and methods for making such compounds or agents, etc.), and are therefore incorporated by reference in their entirety. When PCT applications are referred to it is also understood that the underlying or cited U.S. applications are also incorporated by reference herein in their entirety.

DETAILED DESCRIPTION OF THE INVENTION

Prior to setting forth the invention, it may be helpful to an understanding thereof to set forth definitions of certain terms that will be used hereinafter.

"Medical implant" refers to devices or objects that are implanted or inserted into a body. Representative examples include vascular catheters, dialysis catheters, drainage tubes, nasogastric tubes, prosthetic heart valves, cardiac pacemakers, implantable cardioverter defibrillators, vascular grafts, ear, nose, or throat implants, urological implants, endotracheal or tracheostomy tubes, dialysis catheters, CNS shunts, orthopedic implants, and ocular implants.

As used herein, the term "about" or "consists essentially of" refers to ±15% of any indicated structure, value, or range. Any numerical ranges recited herein are to be understood to include any integer within the range and, where applicable (e.g., concentrations), fractions thereof, such as one tenth and one hundredth of an integer (unless otherwise indicated).

Briefly, as noted above, the present invention discloses medical implants (as well as compositions and methods for making medical implants) which reduce the likelihood of infections in medical implants. More specifically, as noted above, infection is a common complication of the implantation of foreign bodies such as medical devices. Foreign materials provide an ideal site for micro-organisms to attach and colonize. It is also hypothesized that there is an impairment of host defenses to infection in the microenvironment surrounding a foreign material. These factors make medical implants particularly susceptible to infection and make eradication of such an infection difficult, if not impossible, in most cases.

Medical implant failure as a result of infection, with or without the need to replace the implant, results in significant morbidity, mortality and cost to the healthcare system. Since there is a wide array of infectious agents capable of causing medical implant infections, there exists a significant unmet need for therapies capable of inhibiting the growth of a diverse spectrum of bacteria and fungi on implantable devices. The present invention meets this need by providing drugs that can be released from an implantable device, and which have potent antimicrobial activity at extremely low doses. Further, these agents have the added advantage that should resistance develop to the chemotherapeutic agent, the drug utilized in the coating would not be one which would be used to combat the subsequent infection (i.e., if bacterial resistance developed it would be to an agent that is not used as an antibiotic).

Discussed in more detail below are (I) Agents; (II) Compositions and Formulations; (III) Devices, and (IV) Clinical Applications.

I. Agents

Briefly, a wide variety of agents (also referred to herein as 'therapeutic agents' or 'drugs') can be utilized within the context of the present invention, either with or without a carrier (e.g., a polymer; see section II below). Discussed in more detail below are fluoropyrimidines (e.g., 5-FU) and their analogs.

Fluoropyrimidines and Analogs thereof

In one aspect, the therapeutic agent is a fluoropyrimidine, such as 5-fluorouracil, or an analog or derivative thereof, including Carmofur, Doxifluridine, Emitefur, Tegafur, and Floxuridine. Exemplary compounds have the structures:

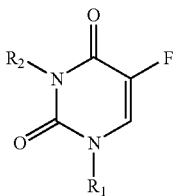

| | $R_1$ | $R_2$ |
|---|---|---|
| 5-Fluorouracil | H | H |
| Carmofur | C(O)NH(CH$_2$)$_5$CH$_3$ | H |
| Doxifluridine | A$_1$ | H |
| Floxuridine | A$_2$ | H |
| Emitefur | CH$_2$OCH$_2$CH$_3$ | B |
| Tegafur | C | H |

A$_1$ 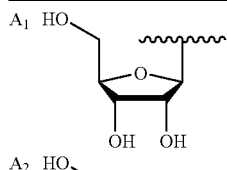

A$_2$ 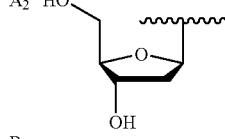

B 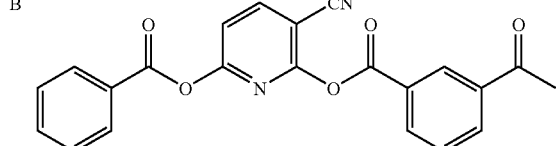

C 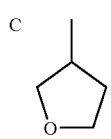

"Fluoropyrimidine," as used herein, refers to a pyrimidine analog that contains at least one F substituent at a carbon of its pyrimidine ring struction. A "primidine analog" refers to a compound with a pyrimidine ring structure (1,3-diazine) substituted with one or more atoms or chemical groups or oxidized at one or more carbons in the pyrimidine ring structure.

Other suitable fluoropyrimidines and analogs thereof include 5-FudR (5-fluoro-deoxyuridine), or an analog or derivative thereof, including 5-iododeoxyuridine (5-IudR), 5-bromodeoxyuridine (5-BudR), Fluorouridine triphosphate (5-FUTP), and Fluorodeoxyuridine monophosphate (5-dFUMP). Exemplary compounds have the structures:

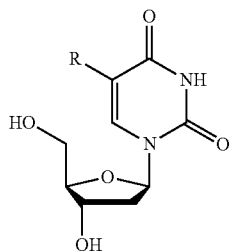

5-Fluoro-2'-deoxyuridine: R=F
5-Bromo-2'-deoxyuridine: R=Br
5-Iodo-2'-deoxyuridine: R=I Other representative examples of fluoropyrimidines or their analogs include N3-alkylated analogues of 5-fluorouracil (Kozai et al., *J. Chem. Soc., Perkin Trans.* 1(19):3145-3146, 1998), 5-fluorouracil derivatives with 1,4-oxaheteroepane moieties (Gomez et al., *Tetrahedron* 54(43):13295-13312, 1998), 5-fluorouracil and nucleoside analogues (Li, *Anticancer Res.* 17(1A):21-27, 1997), cis- and trans-5-fluoro-5,6-dihydro-6-alkoxyuracil (Van der Wilt et al., *Br. J. Cancer* 68(4):702-7, 1993), cyclopentane 5-fluorouracil analogues (Hronowski & Szarek, *Can. J. Chem.* 70(4):1162-9, 1992), A-OT-fluorouracil (Zhang et al., Zongguo Yiyao Gongye Zazhi 20(11):513-15, 1989), N4-trimethoxybenzoyl-5'-deoxy-5-fluorocytidine and 5'-deoxy-5-fluorouridine (Miwa et al., *Chem. Pharm. Bull.* 38(4):998-1003, 1990), 1-hexylcarbamoyl-5-fluorouracil (Hoshi et al., *J. Pharmacobio-Dun.* 3(9):478-81, 1980; Maehara et al., *Chemotherapy (Basel)* 34(6):484-9, 1988), B-3839 (Prajda et al., *In Vivo* 2(2):151-4, 1988), uracil-1-(2-tetrahydrofuryl)-5-fluorouracil (Anai et al., *Oncology* 45(3):144-7, 1988), 1-(2'-deoxy-2'-fluoro-β-D-arabinofuranosyl)-5-fluorouracil (Suzuko et al., *Mol. Pharmacol.* 31(3):301-6, 1987), doxifluridine (Matuura et al., *Oyo Yakuri* 29(5):803-31, 1985), 5'-deoxy-5-fluorouridine (Bollag & Hartmann, *Eur. J. Cancer* 16(4):427-32, 1980), 1-acetyl-3-O-toluoyl-5-fluorouracil (Okada, *Hiroshima J. Med. Sci.* 28(1):49-66, 1979), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680).

These compounds are believed to function as therapeutic agents by serving as antimetabolites of pyrimidine.

In certain embodiment, the fluoropyrimidine is 5-fluorouracil, a compound approved for the treatment of carcinoma and actinic or solar keratoses of the face. It is currently approved for use as an intravenous injection, a topical solution, and a topical cream. 5-FU is metabolized intracellularly to its active form, fluorodeoxyuridine monophosphate (FdUMP). The active form inhibits fungal and bacterial DNA synthesis by inhibiting the normal production of thymidine. The mode of action of 5-FU is to create a thymine deficiency that influences reproduction of bacterial cells and ultimately leads to bacterial cell death.

The effects are most marked on those bacteria that replicate more rapidly and take up 5-FU at a more rapid rate. 5-FU is cell cycle phase-specific, affecting cells in S-phase.

As indicated in the examples below, 5-FU was shown to have antimicrobial activity against bacterial strains commonly found associated with catheter infections using the minimum inhibitory concentration (MIC) test.

In certain embodiments, a fluoropyrimidine or its analog has an MIC of less than or equal to any one of $10^{-4}$ M, $10^{-5}$ M, $10^{-6}$ M, or, $10^{-7}$ M against at least one of the following common infecting organisms associated with medical implants, such as catheters: Staphylococci (*S. aureus*, *S. epidermidis*, and *S. pyogenes*), Enterococci (*E. coli*), gram negative aerobic Bacilli and *Pseudomonas aeruginosa* as measured by, for example, the microtiter broth assay described herein. Furthermore, the fluoropyrimidine or its analog is suitable for use when coated on or otherwise associated with a medical implant at a daily dosage less than that 10%, 5%, 1%, 0.5%, or 0.1% of a daily dosage typically used in chemotherapeutic applications (Goodman and Gilman's The Pharmacological Basis of Therapeutics. Editors J. G. Hardman, L. L. Limbird. Consulting editor A. Goodman Gilman Tenth Edition. McGraw-Hill Medical publishing division. 10th edition, 2001, 2148 pp.).

In certain embodiments, the fluoropyrimidine or its analog is sparingly soluble in water. In certain other embodiments, the fluoropyrimidine or its analog is soluble, slightly soluble, or very slightly soluble in water. Water solubility is expressed in terms of the volume of solvent (e.g., water) required to dissolve 1 gram of a drug (e.g., a fluoropyrimidine or its analog) at a specified temperature (e.g., at 25° C.) and is classified according to the following table from Remington's Pharmaceutical Sciences, Mack Publishing Co., Easton, Pa., 21$^{st}$ edition, 2006.

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

Secondary Agents

In certain embodiments, the medical implants provided herein may comprise more than one fluoropyrimidine or its analog. For example, it may contain 5-fluorouracil and another fluoroprimidine or an analog thereof. In certain embodiments, the anti-infective medical implant may comprise, in addition to a fluoropyrimidine or its analog (e.g., 5-fluorouracil), one or more other chemotherapeutic agents that have anti-infective activities when used at concentrations lower than those for chemotherapy. In certain embodiments, the anti-infective medical implant may comprise, in addition to a fluoropyrimidine or its analog, one or more anti-infective agents (e.g., antibiotics) that are not chemotherapeutic agents. In certain embodiments, the anti-infective medical implant may comprise, in addition to a fluoropyrimidine or its analog, one or more active agents other than anti-infective agents (e.g., anti-thromobotic agents and anti-platelet agents) to help minimize additional complications (e.g., venous thrombosis) associated with medical implants.

Chemotherapeutics as Secondary Anti-Infective Agents

Chemotherapeutic agents other than fluoropyrimidines or their analogs may be used as anti-infective agents in combination with fluoropyrimidines or their analogs to provide anti-infective medical implants. Exemplary classes of chemotherapeutics useful in combination with fluoropyrimidines or their analogs are anthracyclins, folic acid antagonists, podophyllotoxins, camptothecins, hydroxyureas, and platinum complexes.

In certain embodiments, the secondary anti-infective agent is an anthracyclin. Exemplary anthracylins include, but are not limited to, doxorubicin, daunorubicin, idarubicin, epirubicin, pirarubicin, zorubicin, carubicin, anthramycin, mitoxantrone, menogaril, nogalamycin, aclacinomycin A, olivomycin A, chromomycin A$_3$, and plicamycin.

In certain embodiments, the second anti-infective agent is a folic acid antagonist. Exemplary folic acid antagonists include, but are not limited to, methotrexate or derivatives or analogs thereof, such as edatrexate, trimetrexate, raltitrexed, piritrexim, denopterin, tomudex, and pteropterin.

In certain embodiments, the second anti-infective agent is a podophyllotoxin. Exemplary podophyllotoxin include, but are not limited to, etoposide or teniposide.

In certain embodiments, the second anti-infective agent is a camptothecin or an analog or derivative thereof. Exemplary camptothecin compounds include, but are not limited to, topotecan, irinotecan (CPT-11), 9-aminocamptothecin, 21-lactam-20(S)-camptothecin, 10,11-methylenedioxycamptothecin, SN-38, 9-nitrocamptothecin, 10-hydroxycamptothecin.

In certain embodiments, the second anti-infective agent is a hydroxyurea. Hydroxyureas have the following general structure:

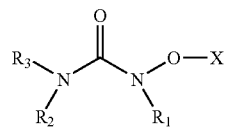

Suitable hydroxyureas are disclosed in, for example, U.S. Pat. No. 6,080,874, wherein R$_1$ is:

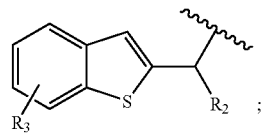

and R$_2$ is an alkyl group having 1-4 carbons and R$_3$ is one of H, acyl, methyl, ethyl, and mixtures thereof, such as a methylether.

Other suitable hydroxyureas are disclosed in, e.g., U.S. Pat. No. 5,665,768, wherein R$_1$ is a cycloalkenyl group, for example N-[3-[5-(4-fluorophenylthio)-furyl]-2-cyclopenten-1-yl]N-hydroxyurea; R$_2$ is H or an alkyl group having 1 to 4 carbons and R$_3$ is H; X is H or a cation.

Other suitable hydroxyureas are disclosed in, e.g., U.S. Pat. No. 4,299,778, wherein R$_1$ is a phenyl group substituted with one or more fluorine atoms; R$_2$ is a cyclopropyl group; and R$_3$ and X is H.

Other suitable hydroxyureas are disclosed in, e.g., U.S. Pat. No. 5,066,658, wherein R$_2$ and R$_3$ together with the adjacent nitrogen form:

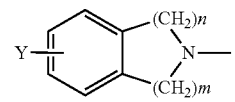

wherein m is 1 or 2, n is 0-2 and Y is an alkyl group.

In certain embodiments, the hydroxyurea has the structure:

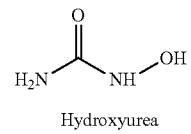

Hydroxyurea

In certain embodiments, the second anti-infective agent is a platinum compound. Exemplary platinum compounds include, but are not limited to, cisplatin, carboplatin, oxaliplatin, and miboplatin.

Other Secondary Anti-Infective Agents

In addition to the above-described chemotherapeutics as secondary anti-infective agents, other anti-infective agents may also be used in combination with a fluoropyrimidine or its analog to provide anti-infective medical implants. Such anti-infective agents may be antibacterial or antifungal agents. Exemplary antibacterial agents include antibiotics (i.e., agents that destroy microorganisms internally), agents effective against gram positive bacteria, and agents effective against gram negative bacteria, disinfectants (i.e., agents that destroy microorganism found on nonliving objects), and antiseptics (i.e., agents that kill or inhibit the growth of microorganisms on the external surfaces of the body). Antiseptics include germicides (i.e., agents capable of destroying microbes) and bacteriostatics (i.e., agents capable of preventing or inhibiting bacterial growth).

Anti-infective agents that may be used in combination with a fluoropyrimidine or its analog include, but are not limited to, silver compounds (e.g., silver chloride, silver nitrate, silver oxide), silver ions, silver particles, iodine, povidone/iodine, chlorhexidine, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin, azaserine, candicidin(s), chlorphenesin, dermostatin(s), filipin, fungichromin, mepartricin, nystatin, oligomycin(s), ciproflaxacin, norfloxacin, ofloxacin, pefloxacin, enoxacin, rosoxacin, amifloxacin, fleroxacin, temafloaxcin, lomefloxacin, perimycin A or tubercidin, and the like.

The fluoropyrimidine or its analog may be further combined with one or more of the antibiotics known to combat growth of gram negative bacteria. Antibiotics that are useful against gram negative bacteria include amoxicillin, ampicillin, azithromycin, aztreonam, cefepime, cefixime, ceftriaxone, cephalosporin C, chloramphenicol, ciprofloxacin, clindamycin, doxycycline, erythromycin, imipenem, meropenem, rifampin, spectinomycin, streptomycin, tetracycline, tobramycin, and trimethoprim.

In certain embodiments, the fluoropyrimdine or its analog may be combined with one or more disinfecting agents, including but are not limited to, $AgNO_3$ (silver nitrate), BAKCl (benzalkonium chloride), BenthonCl (benzethonium chloride), BenzChlPheno (benzyl-p-chlorophenol), Bronopol (2-bromo-2-nitro-1,3-propanediol), CetPyrCl (cetylpyridinium chloride), Chlorhexidine (1,1'-hexamethylenebis[-(p-chlorophenyl)biguanide]), Proxel (1,2-Benzisothiazolin-3-one), Triclosan (5-Chloro-2-(2,4-dichlorophenoxy)phenol), and Vantocil (poly(hexamethylene biguanide) hydrochloride).

In certain embodiments, the fluoropyrimidine or its analog may be combined with one or more antibiotic agents, including but are not limited to, bacitracin, Cephalasporin C, Miconizole Nitrate, Neomycin Sulfate, Norfloxacin, Phosphomycin, Polymyxin B Sufate, and Rifampin.

In certain embodiments, the fluoropyrimidine or its analog may be combined with a combination of two disinfecting agents, a combination of two antibiotic agents, or a combination of a disinfecting agent and an antibiotic agent. Such a combination includes but is not limited to, the combination of $AgNO_3$ and Triclosan, Bronopol and BAKCI, Bronopol and HBAK (heparin benzalkonium complex), Bronopol and Triclosan, Bronopol and Vantocil, and Triclosan and Phosphomycin.

In certain embodiments, the fluoropyrimidine or its analog may be combined with an antiseptic agent. Useful antiseptic agents include but are not limited to alcohols, such as ethanol, 1-propanol, and isopropanol; aldehydes, such as glutaraldehyde, formaldehyde, formaldehyde-releasing agents, o-phthalaldehyde; anilides, such as Triclocarban (TCC; 3,4,4'-triclorocarbanilide); biguanides, such as chlorhexidine, poly(hexamethylene biguanide)hydrochloride; bronopol, such as 2-bromo-2-nitro-1,3-propanediol, diamidines, such as propamidine (4,4-diaminodiphenoxypropane), dibromopropamidine, (2,2-dobromo-4,4-diamidinodiphenoxypropane); halogen-releasing agents, such as Sodium hypochlorite, chlorine dioxide, sodium dichloroisocyanurate; silver compounds, such as silver nitrate, silver sulfadiazine; peroxygens, such as hydrogen peroxide, peracetic acid; phenols, such as phenol, o-phenylphenol, benzyl-p-chlorophenol, chlorocresol; bisphenols, such as triclosan, hexachlorophene, and quaternary compounds, such as benzalkonium chloride, benzethonium chloride, cetylpyridinium chloride, cetyltrimethylammonium bromide, cetylpyridinium chloride.

In certain embodiments, the fluoropyrimidine or its analog may be combined with an antifungal agent. Useful antifungal agents include but are not limited to Amphoteracin B, Micafungin, Caspofungin (Cancidas, MK-0991), Miconazole, V-echinocandin, Nystatin, Fluconazole (Diflucan), Posaconazole, Flucytosine (Ancobon), Ravuconazole, Griseofulvin, Terbinafine, Hamycin, Voriconazole (Vfend), Itraconazole (Sporanox), Ketoconazole. Further examples of anti-infective agents that may be used in combination with a fluoropyrimidine or its analog include quaternary amines and other biocides.

Other Secondary Agents

The anti-infective medical implants may comprise active agents other than anti-infective agents. Depending on the intended use of the medical implants, additional active agents may be desirable. For example, thrombosis and thrombophlebitis are common complications associated with implantation of vascular implants such as vascular catheters. Therefore, vascular implants may include, in addition to a fluoropyrimidine or its analog (with or without a secondary anti-infective agent), an antithrombotic agent (i.e., agents used to treat or prevent thrombosis). Exemplary classes of antithrombotics include antithrombogenics, antiaggregants, thrombolytics, anticoagulants, antiplatelet agents, and other antithrombotics. These agents may be administered alone or in combination.

In exemplary embodiments, the antithrombotic is a thrombolytic, i.e., an agent which dissolves blood clots. Thrombolytics include, for example, enzymes such as brinase; plasminogen activators; e.g., t-PA (alteplase, activase), reteplase (retavase), tenecteplase (TNKase), anistreplase (eminase), plamin, streptokinase (kabikinase, streptase), single chain urokinase, urokinase (abbokinase), and saruplase; and serine endopeptidases, e.g., ancrod, drotrecogin alfa/protein C, and fibrinolysin.

In other exemplary embodiments, the antithrombotic is an anticoagulant, i.e., an agent which prevents coagulation. Anticoagulants include, for example, Vitamin K antagonists, heparin, derivatives, heparin related compounds and direct thrombin inhibitors.

Examples of Vitamin K antagonists include acenocoumarol, clorindione, coumatetralyl, dicumarol (dicoumarol), diphenadione, ethyl biscoumacetate, phenprocoumon, phenindione, tioclomarol and warfarin (coumadin).

Heparin, derivative substances and related compounds of heparin, may be referenced to as the heparin group. Examples of the heparin group agents include antithrombin III, danaparoid, heparin, sulodexide, and low molecular weight heparin (LMWHs), e.g., bemiparin, dalteparin, enoxaparin, nadroparin, parnaparin, reviparin, and tinzaparin. A related agent is fondaparinux, a synthetic sugar composed of the five sugars (pentasaccharide) in heparin that bind to antithrombin.

Other heparin related compounds include heparin reacted with quaternary ammonium compounds, e.g., benzalkonium chloride, tridodecylmethylammonium chloride, cetylpyridinium chloride, benzyldimethylstearylammonium chloride, benzylcetyldimethylammonium chloride. See, for example, U.S. Pat. Nos. 5,525,348 and 5,069,899, issued to Whitbourne, et al., which are hereby incorporated by reference in their entirety.

Examples of direct thrombin inhibitors include argatroban, bivalirudin, dabigatran, desirudin, hirudin, recombinant hirudin, lepirudin, melagatran and ximelagatran (EXANTA®).

In other exemplary embodiments, the antithrombotic is an antiplatelet agent, i.e., an agent which decreases platelet aggregation and inhibit thrombus formation. Examples of antiplatelet agents include cyclooxygenase inhibitors, acetylsalicylic acid (aspirin), adenosine diphosphate (ADP) receptor inhibitors, clopidogrel (Plavix), ticlopidine (Ticlid), phosphodiesterase inhibitors, cilostazol (Pletal), adenosine reuptake inhibitors, prostacyclins such as epoprostenol, and analogues, and dipyridamole (Persantine), dextrans, sulfinpyrazone (Anturane), and glycoprotein IIb/IIIa inhibitors including, monoclonal antibodies and murine-human chimeric antibodies such as abciximab (ReoPro), synthetic peptides such as eptifibatide (Integrilin), and synthetic non-peptides such as tirofiban (Aggrastat). Other examples include aloxiprin, ditazole, carbasalate calcium, cloricromen, indobufen, picotamide, prasugrel, triflusal and prostaglandin analogues, e.g., beraprost, prostacyclin, iloprost, and treprostinil.

Examples of other antithrombotics include defibrotide, dermatan sulfate, rivaroxaban, aminocaproic acid, cilastagel, vapiprost, angiopeptin, thromboxane inhibitors anti-thrombin and synthetic antithrombins.

In certain embodiments, anti-inflammatory agents may be included in anti-infective medical implants provided herein. Exemplary anti-inflammatory agents include dexamethasone, cortisone, fludrocortisone, prednisone, prednisolone, 6α-methylprednisolone, triamcinolone, betamethasone, and aspirin.

In certain embodiments, immunomodulatory agents may be included in anti-infective medical implants provided herein. Exemplary immunomodulatory agents include rapamycin, everolimus, ABT-578, azathioprine azithromycin, analogues of rapamycin, including tacrolimus and derivatives thereof (e.g., EP 0184162B1 and those described in U.S. Pat. No. 6,258,823) and everolimus and derivatives thereof (e.g., U.S. Pat. No. 5,665,772).

In certain embodiments, ant-fibrotic agents may be included in anti-infective medical implants provided herein. Exemplary anti-fibrotic agents include paclitaxel, docetaxol, rapamycin, everorlimus, tacrolimus, epothilone A or B, discodermolide, deuterium oxide ($D_2O$), hexylene glycol, tubercidin, LY290181, aluminum fluoride, ethylene glycol bis-(succinimidylsuccinate), glycine ethyl ester, campothecin, or combinations thereof. Additional examples of anti-fibrotic agents may be found in U.S. Patent Application Publication No. 20050208095 and PCT Application Publication No. WO 2006/135479. The sections related to anti-fibrotic agents in these publications are incorporated herein by reference.

II. Compositions and Formulations

As noted above, therapeutic agents described herein may be formulated in a variety of manners, and thus may additionally comprise a carrier. In this regard, a wide variety of carriers may be selected of either polymeric or non-polymeric origin. The polymers and non-polymer based carriers and formulations which are discussed in more detail below are provided merely by way of example, not by way of limitation.

Within one embodiment of the invention a wide variety of polymers can be utilized to contain and/or deliver one or more of the agents discussed above, including for example both biodegradable and non-biodegradable compositions. Representative examples of biodegradable compositions include albumin, collagen, gelatin, chitosan, hyaluronic acid, starch, cellulose and derivatives thereof (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), alginates, casein, dextrans, polysaccharides, fibrinogen, poly(L-lactide), poly(D,L-lactide), poly(L-lactide-co-glycolide), poly(D,L-lactide-co-glycolide), poly(glycolide), poly(trimethylene carbonate), poly(hydroxyvalerate), poly (hydroxybutyrate), poly(caprolactone), poly(alkylcarbonate) and poly(orthoesters), polyesters, poly(hydroxyvaleric acid), polydioxanone, poly(malic acid), poly(tartronic acid), polyanhydrides, polyphosphazenes, poly(amino acids), copolymers of such polymers and blends of such polymers (see generally, Illum, L., Davids, S. S. (eds.) "Polymers in Controlled Drug Delivery" Wright, Bristol, 1987; Arshady, *J. Controlled Release* 17:1-22, 1991; Pitt, *Int. J. Phar.* 59:173-196, 1990; Holland et al., *J. Controlled Release* 4:155-0180, 1986). Representative examples of nondegradable polymers include poly(ethylene-co-vinyl acetate) ("EVA") copolymers, silicone rubber, acrylic polymers (e.g., polyacrylic acid, polymethylacrylic acid, poly(hydroxyethylmethacrylate), polymethylmethacrylate, polyalkylcyanoacrylate), polyethylene, polyproplene, polyamides (e.g., nylon 6,6), polyurethane (e.g., poly(ester urethanes), poly(ether urethanes), poly(ester-urea), poly(carbonate urethanes)), polyethers (e.g., poly(ethylene oxide), poly(propylene oxide), Pluronics and poly(tetramethylene glycol)) and vinyl polymers [e.g., polyvinylpyrrolidone, poly(vinyl alcohol), poly (vinyl acetate phthalate)]. Polymers may also be developed which are either anionic (e.g., alginate, carrageenin, carboxymethyl cellulose and poly(acrylic acid), or cationic (e.g., chitosan, poly-L-lysine, polyethylenimine, and poly (allyl amine)) (see generally, Dunn et al., *J. Applied Polymer Sci.* 50:353-365, 1993; Cascone et al., *J. Materials Sci.: Materials in Medicine* 5:770-774, 1994; Shiraishi et al., *Biol. Pharm. Bull.* 16(11):1164-1168, 1993; Thacharodi and Rao, *Int'l J. Pharm.* 120:115-118, 1995; Miyazaki et al., *Int'l J. Pharm.* 118:257-263, 1995). Particularly preferred polymeric carriers include poly(ethylene-co-vinyl acetate), polyurethane, acid, poly(caprolactone), poly(valerolactone), polyanhydrides, copolymers of poly(caprolactone) or poly(lactic acid) with a polyethylene glycol (e.g., MePEG), and blends thereof.

Other representative polymers include carboxylic polymers, polyacetates, polyacrylamides, polycarbonates, polyethers, polyesters, polyethylenes, polyvinylbutyrals, polysilanes, polyureas, polyurethanes, polyoxides, polystyrenes, polysulfides, polysulfones, polysulfonides, polyvinylhalides, pyrrolidones, rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxy, melamine, other amino resins, phenolic polymers, and copolymers thereof, water-insoluble cellulose ester polymers (including cellulose acetate propionate, cellulose acetate, cellulose acetate butyrate, cellulose nitrate, cellulose acetate phthalate, and mixtures thereof), polyvinylpyrrolidone, polyethylene glycols, polyethylene oxide, polyvinyl alcohol, polyethers, polysaccharides, hydrophilic polyurethane, polyhydroxyacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, hydroxyethyl cellulose, cellulose nitrate, cellulose acetate, cellulose acetate butyrate, cellulose acetate propionate, polyurethane, polyacrylate, natural and synthetic elastomers, rubber, acetal, nylon, polyester, styrene polybutadiene, acrylic resin, polyvinylidene chloride, polycarbonate, homopolymers and copolymers of vinyl compounds, polyvinylchloride, polyvinylchloride acetate.

Representative examples of patents relating to polymers and their preparation include PCT Publication Nos. WO72827, 98/12243, 98/19713, 98/41154, 99/07417, 00/33764, 00/21842, 00/09190, 00/09088, 00/09087, 2001/17575 and 2001/15526 (as well as their corresponding U.S. applications), and U.S. Pat. Nos. 4,500,676, 4,582,865, 4,629,623, 4,636,524, 4,713,448, 4,795,741, 4,913,743, 5,069,899, 5,099,013, 5,128,326, 5,143,724, 5,153,174, 5,246,698, 5,266,563, 5,399,351, 5,525,348, 5,800,412, 5,837,226, 5,942,555, 5,997,517, 6,007,833, 6,071,447, 6,090,995, 6,099,563, 6,106,473, 6,110,483, 6,121,027, 6,156,345, 6,179,817, 6,197,051, 6,214,901, 6,335,029, 6,344,035, which, as noted above, are all incorporated by reference in their entirety.

Polymers can be fashioned in a variety of forms, with desired release characteristics and/or with specific desired properties. For example, polymers can be fashioned to release a therapeutic agent upon exposure to a specific triggering event such as pH (see, e.g., Heller et al., "Chemically Self-Regulated Drug Delivery Systems," in *Polymers in Medicine III*, Elsevier Science Publishers B.V., Amsterdam, 1988, pp. 175-188; Kang et al., *J. Applied Polymer Sci.* 48:343-354, 1993; Dong et al., *J. Controlled Release* 19:171-178, 1992; Dong and Hoffman, *J. Controlled Release* 15:141-152, 1991; Kim et al., *J. Controlled Release* 28:143-152, 1994; Cornejo-Bravo et al., *J. Controlled Release* 33:223-229, 1995; Wu and Lee, *Pharm. Res.* 10(10):1544-1547, 1993; Serres et al., *Pharm. Res.* 13(2):196-201, 1996; Peppas, "Fundamentals of pH- and Temperature-Sensitive Delivery Systems," in Gurny et al. (eds.), *Pulsatile Drug Delivery*, Wissenschaftliche Verlagsgesellschaft mbH, Stuttgart, 1993, pp. 41-55; Doelker, "Cellulose Derivatives," 1993, in Peppas and Langer (eds.), *Biopolymers I*, Springer-Verlag, Berlin). Representative examples of pH-sensitive polymers include poly(acrylic acid)-based polymers and derivatives (including, for example, homopolymers such as poly(aminocarboxylic acid), poly(acrylic acid), poly(methyl acrylic acid), copolymers of such homopolymers, and copolymers of poly(acrylic acid) and acrylmonomers such as those discussed above). Other pH sensitive polymers include polysaccharides such as carboxymethyl cellulose, hydroxypropylmethylcellulose phthalate, hydroxypropyl-methylcellulose acetate succinate, cellulose acetate trimellilate, chitosan and alginates. Yet other pH sensitive polymers include any mixture of a pH sensitive polymer and a water soluble polymer.

Likewise, polymers can be fashioned which are temperature sensitive (see, e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact. Mater.* 22:167-168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater.* 22:111-112, Controlled Release Society, Inc., 1995; Johnston et al., *Pharm. Res.* 9(3):425-433, 1992; Tung, *Int'l J. Pharm.* 107:85-90, 1994; Harsh and Gehrke, *J. Controlled Release* 17:175-186, 1991; Bae et al., *Pharm. Res.* 8(4):531-537, 1991; Dinarvand and D'Emanuele, *J. Controlled Release* 36:221-227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., *Pharm. Res.* 9(3):283-290, 1992; Bae et al., *Pharm. Res.* 8(5):624-628, 1991; Kono et al., *J. Controlled Release* 30:69-75, 1994; Yoshida et al., *J. Controlled Release* 32:97-102, 1994; Okano et al., *J. Controlled Release* 36:125-133, 1995; Chun and Kim, *J. Controlled Release* 38:39-47, 1996; D'Emanuele and Dinarvand, *Int'l J. Pharm.* 118:237-242, 1995; Katono et al., *J. Controlled Release* 16:215-228, 1991; Hoffman, "Thermally Reversible Hydrogels Containing Biologically Active Species," in Migliaresi et al. (eds.), *Polymers in Medicine III*, Elsevier Science Publishers B.V., Amsterdam, 1988, pp. 161-167; Hoffman, "Applications of Thermally Reversible Polymers and Hydrogels in Therapeutics and Diagnostics," in *Third International Symposium on Recent Advances in Drug Delivery Systems*, Salt Lake City, Utah, Feb. 24-27, 1987, pp. 297-305; Gutowska et al., *J. Controlled Release* 22:95-104, 1992; Palasis and Gehrke, *J. Controlled Release* 18:1-12, 1992; Paavola et al., *Pharm. Res.* 12(12):1997-2002, 1995).

Representative examples of thermogelling polymers include homopolymers such as poly(N-methyl-N-n-propylacrylamide), poly(N-n-propylacrylamide), poly(N-methyl-N-isopropylacrylamide), poly(N-n-propylmethacrylamide), poly(N-isopropylacrylamide), poly(N, n-diethylacrylamide), poly(N-isopropylmethacrylamide), poly(N-cyclopropylacrylamide), poly(N-ethylmethyacrylamide), poly(N-methyl-N-ethylacrylamide), poly(N-cyclopropylmethacrylamide) and poly(N-ethylacrylamide). Moreover thermogelling polymers may be made by preparing copolymers between (among) monomers of the above, or by combining such homopolymers with other water soluble polymers such as acrylmonomers (e.g., acrylic acid and derivatives thereof such as methylacrylic acid, acrylate and derivatives thereof such as butyl methacrylate, acrylamide, and N-n-butyl acrylamide).

Other representative examples of thermogelling cellulose ether derivatives such as hydroxypropyl cellulose, methyl cellulose, hydroxypropylmethyl cellulose, ethylhydroxyethyl cellulose, and Pluronics, such as F-127.

A wide variety of forms may be fashioned by the polymers of the present invention, including for example, rod-shaped devices, pellets, slabs, particulates, micelles, films, molds, sutures, threads, gels, creams, ointments, sprays or capsules (see, e.g., Goodell et al., *Am. J. Hosp. Pharm.* 43:1454-1461, 1986; Langer et al., "Controlled release of macromolecules from polymers", in *Biomedical Polymers, Polymeric Materials and Pharmaceuticals for Biomedical Use*, Goldberg, E. P., Nakagim, A. (eds.) Academic Press, pp. 113-137, 1980; Rhine et al., *J. Pharm. Sci.* 69:265-270, 1980; Brown et al., *J. Pharm. Sci.* 72:1181-1185, 1983; and Bawa et al., *J. Controlled Release* 1:259-267, 1985). Agents may be incorporated by dissolution in the polymer, occlusion in the matrices of the polymer, bound by covalent linkages, or encapsulated in microcapsules. Within certain preferred embodiments of the invention, therapeutic compositions are provided in noncapsular formulations, such as coatings microspheres (ranging from nanometers to micrometers in size), pastes, threads or sutures of various size, films and sprays.

Other compounds which can be utilized to carry and/or deliver the agents provided herein include vitamin-based compositions (e.g., based on vitamins A, D, E and/or K, see, e.g., PCT publication Nos. WO 98/30205 and WO 00/71163) and liposomes (see, U.S. Pat. Nos. 5,534,499, 5,683,715, 5,776,485, 5,882,679, 6,143,321, 6,146,659, 6,200,598, and PCT Publication Nos. WO 98/34597, WO 99/65466, WO 00/01366, WO 00/53231, WO 99/35162, WO 00/117508, WO 00/125223, WO 00/149,268, WO 00/1565438, and WO 00/158455).

Preferably, therapeutic compositions of the present invention are fashioned in a manner appropriate to the intended use. Within certain aspects of the present invention, the therapeutic composition should be biocompatible, and release one or more agents over a period of several days to months, such as for at least 2, 3, 4, 5, 6 or 7 days; 2, 3 or 4 weeks; or 2, 3, 4, 5, 6, 7, 8, 9, 10, 11, or 12 months. Further, therapeutic compositions of the present invention should preferably be stable for several months and capable of being produced, and maintained under sterile conditions.

Within certain aspects of the present invention, therapeutic compositions may be fashioned in any size ranging from 50 nm to 500 µm, depending upon the particular use. Alternatively, such compositions may also be readily applied as a "spray" which solidifies into a film or coating. Such sprays may be prepared from microspheres of a wide array of sizes, including for example, from 0.1 µm to 9 µm, from 10 µm to 30 µm and from 30 µm to 100 µm.

Therapeutic compositions of the present invention may also be prepared in a variety of "paste" or gel forms. For example, within one embodiment of the invention, therapeutic compositions are provided which are liquid at one temperature (e.g., temperature greater than 37° C.) and solid or semi-solid at another temperature (e.g., ambient body temperature, or any temperature lower than 37° C.). Also included are polymers, such as Pluronic F-127, which are liquid at a low temperature (e.g., 4° C.) and a gel at body temperature. Such "thermopastes" may be readily made given the disclosure provided herein.

Within yet other aspects of the invention, the therapeutic compositions of the present invention may be formed as a film. Preferably, such films are generally less than 5, 4, 3, 2 or 1 mm thick, more preferably less than 0.75 mm or 0.5 mm thick, and most preferably less than 500 µm. Such films are preferably flexible with a good tensile strength (e.g., greater than 50, preferably greater than 100, and more preferably greater than 150 or 200 N/cm$^2$), good adhesive properties (i.e., readily adheres to moist or wet surfaces), and have controlled permeability.

Within certain embodiments of the invention, the therapeutic compositions can also comprise additional ingredients such as surfactants (e.g., Pluronics such as F-127, L-122, L-92, L-81, and L-61).

Within further aspects of the present invention, polymers are provided which are adapted to contain and release a hydrophobic compound, the carrier containing the hydrophobic compound in combination with a carbohydrate, protein or polypeptide. Within certain embodiments, the polymeric carrier contains or comprises regions, pockets or granules of one or more hydrophobic compounds. For example, within one embodiment of the invention, hydrophobic compounds may be incorporated within a matrix which contains the hydrophobic compound, followed by incorporation of the matrix within the polymeric carrier. A variety of matrices can be utilized in this regard, including for example, carbohydrates and polysaccharides, such as starch, cellulose, dextran, methylcellulose, and hyaluronic acid, proteins or polypeptides such as albumin, collagen and gelatin. Within alternative embodiments, hydrophobic compounds may be contained within a hydrophobic core, and this core contained within a hydrophilic shell.

Other carriers that may likewise be utilized to contain and deliver the agents described herein include: hydroxypropyl β-cyclodextrin (Cserhati and Hollo, *Int. J. Pharm.* 108:69-75, 1994), liposomes (see, e.g., Sharma et al., *Cancer Res.* 53:5877-5881, 1993; Sharma and Straubinger, *Pharm. Res.* 11(60):889-896, 1994; WO 93/18751; U.S. Pat. No. 5,242, 073), liposome/gel (WO 94/26254), nanocapsules (Bartoli et al., *J. Microencapsulation* 7(2):191-197, 1990), micelles (Alkan-Onyuksel et al., *Pharm. Res.* 11(2):206-212, 1994), implants (Jampel et al., *Invest. Ophthalm. Vis. Science* 34(11): 3076-3083, 1993; Walter et al., *Cancer Res.* 54:22017-2212, 1994), nanoparticles (Violante and Lanzafame PAACR), nanoparticles—modified (U.S. Pat. No. 5,145,684), nanoparticles (surface modified) (U.S. Pat. No. 5,399,363), taxol emulsion/solution (U.S. Pat. No. 5,407, 683), micelle (surfactant) (U.S. Pat. No. 5,403,858), synthetic phospholipid compounds (U.S. Pat. No. 4,534,899), gas borne dispersion (U.S. Pat. No. 5,301,664), foam, spray, gel, lotion, cream, ointment, dispersed vesicles, particles or droplets solid- or liquid-aerosols, microemulsions (U.S. Pat. No.

5,330,756), polymeric shell (nano- and micro-capsule) (U.S. Pat. No. 5,439,686), taxoid-based compositions in a surface-active agent (U.S. Pat. No. 5,438,072), liquid emulsions (Tarr et al., *Pharm Res.* 4:62-165, 1987), nanospheres (Hagan et al., *Proc. Intern. Symp. Control Rel. Bioact. Mater.* 22, 1995; Kwon et al., *Pharm Res.* 12(2):192-195; Kwon et al., *Pharm Res.* 10(7):970-974; Yokoyama et al., *J. Contr. Rel.* 32:269-277, 1994; Gref et al., *Science* 263:1600-1603, 1994; Bazile et al., *J. Pharm. Sci.* 84:493-498, 1994) and implants (U.S. Pat. No. 4,882,168).

The agents provided herein can also be formulated as a sterile composition (e.g., by treating the composition with ethylene oxide or by irradiation), packaged with preservatives or other suitable excipients suitable for administration to humans. Similarly, the devices provided herein (e.g., coated catheter) may be sterilized and prepared suitable for implantation into humans.

In another aspect, the present invention provides an anti-infective composition for applying to or incorporated into (e.g., coating) a medical implant such as a catheter or a tube that comprises a polyurethane, a cellulose or cellulose-derived polymer, and a fluoropyrimidine or its analog, wherein the fluoropyrimidine or its analog is present in the composition (e.g., in the form of a coating) at a concentration effective in reducing or inhibiting infection associated with the medical implant.

The composition (e.g., a coating composition) provided herein allows for an effective amount of a fluoropyrimidine or its analog, such as 5-FU, to be applied to or incorporated onto (e.g., coated on) a medical implant (e.g., a catheter or a tube). In addition, the polymers in the composition enable release of the fluoropyrimidine or its analog from the composition (e.g., in form of a coating) on the implant at effective concentrations over a sustained period of time. Furthermore, the composition (e.g., a coating composition) provided herein may be applied to or incorporated onto, such as form a coating on, a medical implant (e.g., a catether or a tube) with one or more of the following desirable features: (1) strong adhesion to the implant when it is in use (e.g., after insertion in patients); (2) good flexibility and elasticity to remain intact following sterilization and implantation of the implant in the patient; (3) excellent uniformity; (4) not significantly bioerodable, which allows for sustained release of the fluoropyrimidine or its analog over a period of days, weeks, or months and minimizes patient's response to breakdown products of the coating; and (5) easy control of drug elution rate by using various ratios of the polyurethane to the cellulose or cellulose-derived polymer in the composition, which in turn allows for better control of the concentration and duration of anti-infective activity of the fluoropyrimidine or its analog.

In certain embodiments, the compositions (e.g., coating compositions) provided herein were developed and optimized for total drug loading, drug elution kinetics and antimicrobial efficacy. They were modified to balance coating thickness, physical properties (e.g., flexibility), coating quality (e.g., adhesion and coating uniformity), and drug release kinetics. Parameters of the coating composition affecting these attributes include the ratios of the coating polymers to each other, the ratio of drug to total polymer, percent solids in the coating, choice and relative amounts of solvents, and the viscosity of the coating solution. In general, changes to the drug/polymer ratio can affect the rate and amount of drug eluted from the medical implant. Increasing the drug to polymer ratio in the coating composition typically increases the rate of drug elution. However, if drug loading is too high, release of the drug from the coating can create voids and destroy the coating integrity. In certain embodiments, the total solids (and viscosity and coating thickness) were increased to achieve a higher dose of drug (e.g., 5-FU) while keeping the drug to polymer ratio below a certain level (e.g., about 40%, 30%, 25%, 20%, 15% or 10%).

"Polyurethane" refers to a linear polymer that has a molecular backbone containing carbamate groups ($-NHCO_2$). These groups are produced through a chemical reaction between a diisocyanate (a compound that comprises two $-NCO$ groups) or polyisocyanate (a compound that comprises more than two $-NCO$ groups) and a diol (a compound with two $-OH$ groups) or polyol (a compound that comprises more than two $-OH$ groups).

Diisocyanates and polyisocyanates that may be used to form polyurethanes useful in the present application can be aromatic, such as diphenylmethane diisocyaanate (MDI) or toluene diisocyanate (TDI), or aliphatic, such as hexamethylene diisocyanate (HDI) or isophorone diisocyanate (IPDI). Polyurethanes made of aromatic diisocyanates or aromatic polyisocyanates are referred to as "aromatic polyurethanes." Similarly, polyurethanes made of aliphatic diisocynates or aliphatic polyisocyanates are referred to as "aliphatic polyurethanes."

Additional exemplary diisocyanates and polyisocyanates that may be used to make polyurethanes useful in the present application include, but are not limited to, polymeric isocyanate (PMDI), 1,5-naphthalene diisocyanate, biotolylene diisocyanate, 2,4-tolylene diisocyanate and position isomers thereof, 4,4'-diphenylmethane diisocyanate and position isomer thereof, polymethylenepolyphenyl isocyanate, 1,5-naphylene diisocyanate, olymeric diphenylmethane diisocyanate, which is a blend of molecules with two-, three-, and four or more isocyanate groups. Further examples of polyisocyanates may be found in Encyclopedia of Polymer Science and Technology, Mark et al., 1969, incorporated herein by reference.

Polyols that may be used to make polyurethanes in the coating compositions provided herein may be polyester polyols. They are formed by polyesterification of a di-acid, such as adipic acid, with glycols, such as ethylene glycol or dipropylenen glycol. Polyurethane formed with polyester polyols are referred to as "poly(ester urethanes)."

Polyether polyols may also be used to make polyurethanes in the coating compositions provided herein. Polyether polyols are formed by free radical additions of propylene oxide or ethylene oxide onto a hydroxyl or amine containing initiator. Exemplary polyether polyols that may be used to form polyurethanes include polyethylene glycol, polypropylene glycol, and polytetramethylene glycol. Polyurethanes formed with polyether polyols are referred to as "poly(ether urethanes)."

Polyols that may be used to make polyurethanes in the coating compositions provided herein may also be a polycarbonate terminated with hydroxyl groups. The resulting polyurethanes are referred to as "poly(carbonate urethanes)." Exemplary poly(carbonate urethanes) that may be included in the coating compositions provided herein include CHRONOFLEX® AL (aliphatic), CHRONOFLEX® AR (aromatic), CHRONOFLEX® C (aromatic), and BIONATE® (aromatic) 80A, 90A, 55D, and 75D.

Polyurethanes present in the compositions (e.g., coating compositions) provide flexibility and adhesion to the medical implant (e.g., a catheter or a tube). In addition, polyurethanes may be more or less hydrophilic depending on the number of hydrophilic groups contained in the polymer structures. The polyurethanes included in the coating compositions provided herein are water-insoluble, flexible, and compatible with cellulose or cellulose-derived polymers and fluoropyrimidines or their analogs also present in the coating compositions.

As indicated above, the compositions (e.g., coating compositions) provided herein also comprise cellulose or cellulose-derived polymers. "Cellulose" refers to a carbohydrate, $(C_6H_{10}O_5)_n$, that is composed of glucose units. "Cellulose-derived polymers" refers to chemically altered forms of cellulose, such as cellulose esters, that are water insoluble. Various types of cellulose esters, such as cellulose acetate, cellulose acetate propionate, cellulose acetate butyrate, cellulose acetate phthalate, cellulose xanthate, and cellulose nitrate (also referred to as "nitrocellulose") may be used in the coating compositions provided herein.

Certain cellulose esters (e.g., cellulose nitrates) are particularly compatible with fluoropyrimidines (e.g., 5-FU) or their analogs. Cellulose esters can impart non-tackiness and cohesiveness to the coatings, and as hydrophobic, water-insoluble polymers, cellulose esters can be highly water resistant. Furthermore, the structure contributes to high degree of stabilization provided to active agents entrapped in cellulose esters. The structure of nitrocellulose is given below:

In certain embodiments, the cellulose ester may be a nitrocellulose. The amount of nitrogen content in cellulose nitrates can vary. Cellulose nitrate (nitrogen content=11.8-12.2%) preferably is used in this invention, although grades of the polymer having lower nitrate concentrations (e.g., 11.3-11.8% or 10.8-11.3%) could be used. Cellulose nitrates are available in viscosities ranging from high viscosity (e.g., 600-1000"; 60-80"; 15-20"; 5-6"), medium viscosity (e.g., ½"; ⅜"; ¼"; 30-35 cps), to low viscosity (e.g., 18-25 cps or 10-15 cps). Lower viscosity grades, such as 3.5, 0.5 or 0.25 seconds, can be used in order to provide favorable rheological properties when combined with the coating solids used in these compositions. Alternatively, higher or lower viscosity grades could be used. At the solids concentrations preferred for use in the practice of the invention, higher viscosity grades can produce coating solutions of such high viscosity, which may cause coating of medical implants to become technically challenging. Physical properties such as tensile strength, elongation, flexibility, and softening point are related to viscosity. Viscosity, in turn, depends on the molecular weight of the polymer and can decrease with the lower molecular weight species, especially below the 0.25 second grades.

Representative examples of nitrocellulose polymers include grades A, AM and E nitrocellulose from Dow Wolff Cellulosics, NCC-H130, NCC-H60, NCC-H3040, NCC-H1520, NCC-H0506, NCC-HM005, NCC-H0025, NCC-M0025, and NCC-H0062L nitrocellulose from Darwin Chemical, the ester-soluble types, such as H4, H7, H9, H12, H15, H22.5, H24, H27, H28, H30, and H33 and alcohol soluble types, such as AH15, AH22, AH25, AH27, and AH 28 from Hagedorn, L, H, and M types of nitrocellulose from Shandong Zhiqiang Group Co., and various types of nitrocellulose from Sherman Chemicals Ltd. Nitrocellulose polymers are also available from many other manufacturers and providers.

Additional examples of cellulose esters that may be combined with a fluoropyrimidine or its analog include cellulose acetate, cellulose acetate propionate, cellulose acetate butyrate, cellulose acetate phthalate, and cellulose xanthate.

As described above, the composition (e.g., a coating composition) comprises, in addition to cellulose or a cellulose-derived polymer, a polyurethane. The presence of both a polyurethane and a cellulose or cellulose-derived polymer facilitates the loading or elution control of a fluoropyrimidine and its analog in the composition. Cellulose or cellulose-derived polymers in the compositions provided herein are typically hydrophobic, whereas as discussed above, polyurethane in the compositions may be more or less hydrophilic depending on its structure. The ratio of hydrophilic to hydrophobic components in the coating compositions is an important parameter that affects the final properties and release characteristics of the composition (e.g., in form of a coating) on medical implants.

For instance, to deliver a sparingly water soluble fluoropyrimidine or its analog, such as 5-FU, a higher percentage of hydrophobic cellulose or cellulose-derived polymer (i.e., a lower ratio of polyurethane to cellulose or cellulose-derived polymer) may be needed comparing with delivering a water insoluble drug. The higher percentage of hydrophobic cellulose or cellulose-derived polymer prevents the sparingly water soluble fluoropyrimidine or its analog (i.e., 5-FU) from being released from the composition (e.g., in form of a coating) too quickly if the medical implant with such coating is intended to maintain its anti-infective activity for a sustained period of time. Thus, the weight ratio of polyurethane to cellulose or cellulose-derived polymer may be optimized by taking into consideration various factors such as the hydrophobicity of the polyurethane, the hydrophilicity of the fluoropyrimidine or its analog, the amount of the fluoropyrimidine and its analog present in the coating composition (e.g., the ratio of the fluoropyrimidine or its analog to total polymers), and the period during which a medical implant that comprises the composition intended to have its anti-infective activity.

In certain embodiments, the weight ratio of the polyurethane (e.g., a poly(carbonate urethane)) to the cellulose or cellulose-derived polymer (e.g., nitrocellulose) in the composition (e.g., a coating composition) ranges from about 1:10 to about 2:1, such as from 1:9 to 1:1, 1:8 to 1:1, 1:7 to 1:1, 1:6 to 1:1, 1:5 to 1:1, 1:4 to 1:1, 1:3 to 1:1, 1:2 to 1:1, 1:9 to 1:2, 1:8 to 1:2, 1:7 to 1:2, 1:6 to 1:2, 1:5 to 1:2, 1:4 to 1:2, 1:3 to 1:2, 1:9 to 1:3, 1:8 to 1:3, 1:7 to 1:3, 1:6 to 1:3, 1:5 to 1:3, 1:4 to 1:3, 1:9 to 1:4, 1:8 to 1:4, 1:7 to 1:4, 1:6 to 1:4, 1:5 to 1:4, 1:9 to 1:5, 1:8 to 1:5, 1:7 to 1:5, 1:6 to 1:5, 1:9 to 1:6, 1:8 to 1:6, 1:7 to 1:6, 1:9 to 1:7, 1:8 to 1:7, or 1:9 to 1:8. In certain embodiments, the weight ratio of the polyurethane (e.g., a poly(carbonate urethane)) to the cellulose or cellulose-derived polymer (e.g., nitrocellulose) in the composition (e.g., a coating composition) is about 2:1, 1:1, 1:2, 1:3, 1:4, 1:5, 1:6, 1:7, 1:8, 1:9, or 1:10.

In certain embodiments, the compositions (e.g., coating compositions) may include other polymers to impart certain desirable physical properties, such as to modify hydrophobicity, control elution, and improve flexibility. Exemplary additional polymers include, but are not limited to, hydroxyethyl methacrylate, acrylic HEMA (polyhydroxyethyl methacrylate/methylmethacrylate) copolymers, polyvinyl pyrrolidone, polyethylene glycols, and polyethylene oxides.

The composition (e.g., a coating composition) provided herein comprises fluoropyrimidines or their analogs at a concentration effective in reducing or inhibiting infection associated with the medical implant that comprises the composition. Any fluoropyrimidine or its analog with an anti-infective activity may be used in the coating composition, including those (e.g., 5-FU) described above.

A "concentration effective in reducing or inhibiting infection" refers to a concentration of a fluoropyrimidine or its analog in a coating composition at which when the composition is applied or incorporated (e.g., coated) onto a medical implant, the fluoropyrimidine or its analog is present on or released at an amount sufficient to statistically significantly reduce or inhibit infection associated with the medical implant when inserted into a patient compared with infection associated with the same medical implant but without the fluoropyrimidine or its analog in its coating. Effective concentrations can be maintained from the time of insertion of the medical implant (e.g., a catheter) to up to a month or more. In certain embodiments, the present medical implants can offer a concentration effective in reducing or inhibiting infection for at least 30 days, thus significantly extending or even eliminating the change interval for the medical implant.

"Infection associated with a medical implant" or "medical implant-related infection" (CRI) refers to infection directly or indirectly caused by the insertion of a medical implant into a patient. It includes local infection on the medical implant and systemic infection resulted from the infection on the medical implant. Reduction in colonization by bacteria also may reduce biofilm formation on the implanted medical implant (e.g., a catheter), making it less likely to serve as a reservoir for additional infection.

The amount of a fluoropyrimidine or its analog to be included in the composition (e.g., a coating composition) provided herein may depend on various factors such as the anti-infective activity of the analog, the polymer components in the composition (e.g., a particular polyurethane and cellulose or a particular cellulose-derived polymer), the weight ratio of the polyurethane to the cellulose or cellulose-derived polymer, and the intended use of a medical implant that comprises (e.g., coated with) the composition. The amount should be sufficient for the fluoropyrimidine or its analog to be released from the medical implant at concentrations effective in reducing or inhibiting medical implant-related infections for the intended period of time, such as for at least 1, 2, 3, 4, 5, 6, 7, 8, 9, 10 days or at least 2, 3, 4, 5, 6, 7, 8, 9, or 10 weeks.

In certain embodiments, the weight ratio of the fluoropyrimidine or its analog (e.g., 5-FU) to the sum of the polyurethane (e.g., poly(carbonate urethane)) and the cellulose or cellulose-derived polymer (e.g., nitrocellulose) in the composition (e.g., a coating composition) ranges from 2% to 40%, such as 3% to 30%, 4% to 20%, 5% to 25%, 10% to 20%, 15% to 19%, or 10% to 19%, or about 10%, 15%, or 20%. In certain embodiments, the weight ratio of the fluoropyrimidine (e.g., 5-FU) or its analog to the sum of the polyurethane and the cellulose or cellulose-derived polymer in the coating is below 20%.

In certain embodiments, the composition (e.g., a coating composition) comprises poly(carbonate urethane), nitrocellulose, and 5-FU in which the weight ratio of the poly(carbonate urethane) to the nitrocellulose ranges from 1:2 to 1:4 (e.g., about 1:3), and the weight ratio of 5-FU to the sum of poly(carbonate urethane) and nitrocellulose is below 20% (e.g., about 15%).

In certain embodiments, the composition (e.g., a coating composition) further comprises one or more of the following components: a solvent for the cellulose or cellulose-derived polymer, a solvent for the polyurethane, and a swelling agent. Exemplary solvents for cellulose or cellulose-derived polymers are known in the art, including ketones such as methyl ethyl ketone (MEK). Exemplary solvents for polyurethanes are also known in the art, including amides, such as dimethylacetamide (DMAC), N-methylpyrrolidone (NMP), dimethylsulfoxide (DMSO), tetrahydrofuran (THF), toluene, cyclohexanone, and 2-methyl pentanone (MIEK). Small amounts of a cosolvent, such as isopropyl alcohol, ethanol, n-butyl alcohol also may be used to improve solubility of the fluoropyrimidine or its analog in the coating solution.

A "swelling agent" is an agent having the ability to swell the substrate of a medical implant, thereby enabling some of the composition (e.g., a coating composition) to penetrate superficially into the substrate surface and improve adhesion. The choice of swelling agent depends on the composition of the substrate and should generally be chosen to avoid dissolution of the medical implant substrate. Such agents are well known in the art and include, for example, ethers such as tetrahydrofuran (THF), DMAC, NMP, toluene, and alcohols. Swelling of polyurethane substrates may be achieved using any of these solvents.

In certain embodiments, the composition (e.g., a coating composition) comprises poly(carbonate urethane), nitrocellulose, 5-FU, and a solvent or mixture of solvents (e.g., DMAC, MEK, and THF). The solvent or solvent mixture is capable of dissolving both the fluoropyrimidine or its analog and the polymeric components of the formulation and yields a coating that has adequate adhesion to the substrate. In certain embodiments, a mixture of solvents comprises, or is composed of, about 2% to about 25% DMAC, about 15% to about 58% MEK, and about 40% to about 60% THF. The above percentages of DMAC, MEK and THF in the mixture of solvents are weight percentages of each component in the solvent mixture.

In certain exemplary compositions of such embodiments, the weight ratio of the poly(carbonate urethane) to the nitrocellulose ranges from 1:2 to 1:4 (e.g., about 1:3), and the weight ratio of 5-FU to the sum of poly(carbonate urethane) and nitrocellulose ranges from 5% to 25% (e.g., about 15% to about 20%). In the same or different exemplary compositions of the above-noted embodiments, the total weight percentage of the poly(carbonate urethane), the nitrocellulose, and 5-FU in the coating compositions may be from 2% to 20%, such as from 4% to 10%, about 5%, about 6%, about 7%, or about 8%.

In certain embodiments, the composition (e.g., a coating composition) provided herein may further comprise one or more additional anti-infective agents or other active agents. The anti-infective agents include additional fluoropyrimidines or their analogs, other chemotherapeutics with anti-infective activities, antibiotics, and anti-fungal agents. Other active agents include antithrombotic agents such as antiplatelet agents, anti-inflammatory agents, immunomodulatory agents and anti-fibrotic agents. Examples of additional anti-infective agents and other active agents are described above.

In certain embodiments, the compositions (e.g., coating compositions) provided herein may further comprise various agents that can impart certain desirable attributes, such as plasticizers (e.g., glycerol and triethyl citrate) to increase the flexibility, colorants such as dyes, hyaluronic acid or PVP to improve lubricity, heparin to enhance biocompatibility or hemocompatability of the coating.

III. Medical Implants

A. Representative Medical Implants

A wide variety of implants or devices can be coated with or otherwise constructed to contain and/or release the therapeutic agents provided herein. Representative examples include cardiovascular devices (e.g., implantable central venous catheters, peripheral intravenous catheters, arterial lines and transducers, port-catheters, venous ports, tunneled venous catheters, chronic infusion lines or ports, including hepatic artery infusion catheters, pacemakers and pacesmaker leads (see, e.g., U.S. Pat. Nos. 4,662,382, 4,782,836, 4,856,521, 4,860,751, 5,101,824, 5,261,419, 5,284,491, 6,055,454, 6,370,434, and 6,370,434), implantable defibrillators (see, e.g., U.S. Pat. Nos. 3,614,954, 3,614,955, 4,375,817, 5,314,430, 5,405,363, 5,607,385, 5,697,953, 5,776,165, 6,067,471, 6,169,923, and 6,152,955)); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); dialysis catheters (e.g., hemodialysis catheters and peritoneal dialysis catheters);

gastrointestinal devices (e.g., chronic indwelling catheters, feeding tubes, portosystemic shunts, shunts for ascites, peritoneal implants for drug delivery, peritoneal dialysis catheters, and suspensions or solid implants to prevent surgical adhesions); genitourinary devices (e.g., uterine implants, including intrauterine devices (IUDs) and devices to prevent endometrial hyperplasia, fallopian tubal implants, including reversible sterilization devices, fallopian tubal stents, artificial sphincters and periurethral implants for incontinence, ureteric stents, chronic indwelling catheters, bladder augmentations, or wraps or splints for vasovasostomy, central venous catheters (see, e.g., U.S. Pat. Nos. 3,995,623, 4,072,146 4,096,860, 4,099,528, 4,134,402, 4,180,068, 4,385,631, 4,406,656, 4,568,329, 4,960,409, 5,176,661, 5,916,208), urinary catheters (see, e.g. U.S. Pat. Nos. 2,819,718, 4,227,533, 4,284,459, 4,335,723, 4,701,162, 4,571,241, 4,710,169, and 5,300,022)); prosthetic heart valves (see, e.g., U.S. Pat. Nos. 3,656,185, 4,106,129, 4,892,540, 5,528,023, 5,772,694, 6,096,075, 6,176,877, 6,358,278, and 6,371,983), vascular grafts (see, e.g. 3,096,560, 3,805,301, 3,945,052, 4,140,126, 4,323,525, 4,355,426, 4,475,972, 4,530,113, 4,550,447, 4,562,596, 4,601,718, 4,647,416, 4,878,908, 5,024,671, 5,104,399, 5,116,360, 5,151,105, 5,197,977, 5,282,824, 5,405,379, 5,609,624, 5,693,088, and 5,910,168), opthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., breast implants or chin implants), catheter cuffs and orthopedic implants (e.g., cemented orthopedic prostheses), drainage tubes, and nasogastric tubes. Further exemplary medical implants that may be coated with or otherwise comprise a composition that comprises a fluoropyrimidine or its analog according to the present invention include those discussed in the Clinical Applications section below.

In certain embodiments, the medical implants are catheters, including but not limited to: acorn-tipped catheters, angiography catheters, balloon catheters, balloon-tip catheters, bicoudate catheters, Bozeman-Fritsch catheters, Braasch catheters, Broviac catheters, brush catheters, cardiac catheters, central venous catheters, conical catheters, catheters coude, catheters a demeure, de Pezzer catheters, double-channel catheters, elbowed catheters, Eustachian catheters, female catheters, Fogarty embolectomy catheters, Foley catheters, Gouley catheters, Hickman catheters, indwelling catheters, intracardiac catheters, Malecot catheters, Nelaton catheters, olive-tipped catheters, pacing catheters, Pezzer catheters, Phillips catheters, pigtail catheters, prostatic catheters, pulmonary artery catheters, Robinson catheters, self-retaining catheters, spiral tip catheters, Swan-Ganz catheters, two-way catheters, vertebrated catheters, whistle-tip catheters, and winged catheters. The above types of catheters are well known in the art and defined in Stedman's Medical Dictionary, 27$^{th}$ Edition, Lippincott Williams & Wilkins, 2000.

Additional representative examples of catheters that may be coated with or otherwise comprise a composition that comprises a pyrimidine analog according to the present invention on the catheters include implantable venous catheters, tunneled venous catheters, coronary catheters useful for angiography, angioplasty, or ultrasound procedures in the heart or in peripheral veins and arteries, chronic infusion lines, hepatic artery infusion catheters, central venous catheters (see, e.g., U.S. Pat. Nos. 3,995,623, 4,072,146 4,096, 860, 4,099,528, 4,134,402, 4,180,068, 4,385,631, 4,406,656, 4,568,329, 4,960,409, 5,176,661, 5,916,208), peripheral intravenous catheters, peripherally inserted central venous catheters (PIC lines), flow-directed balloon-tipped pulmonary artery catheters, arterial lines, total parenteral nutrition catheters, devices for continuous subarachnoid infusions, chronic dwelling catheters (e.g., chronic dwelling gastrointestinal catheters and chronic dwelling genitourinary catheters), peritoneal dialysis catheters, hemodialysis catheters, and urinary catheters (see, e.g. U.S. Pat. Nos. 2,819, 718, 4,227,533, 4,284,459, 4,335,723, 4,701,162, 4,571,241, 4,710,169, and 5,300,022).

Additional exemplary catheters that may be coated with or otherwise comprise a composition that comprises a pyrimidine analog according to the present invention on the catheters include SKATER® drainage catheters for percutaneous fluid collection drainage procedures, such as SKATER® biliary catheters, SKATER® nephrostomy catheter, SKATER® single step catheters; GOLDEN-RULE™ scaling catheters for delivering radiopaque media to selected sites in the vascular system and anatomical measurements in conjunction with routine diagnostic procedures, and HSG catheters for use in the injection of contrast material in the examination of the uterus and fallopian tubes. These exemplary catheters are available from Angiotech.

The catheters may have one lumen or multiple lumens, depending on the application. In certain embodiments, the catheters may be double catheters (e.g., hemodialysis catheters) or triple-lumen catheters (e.g., central venous catheters). In other embodiments, the catheters may have 4 or 5 lumens.

In certain embodiments, the catheter does not include an expandable portion such as a balloon. In other embodiments, the catheter is not a transient delivery vehicle that is intended to be removed shortly after to delivery of a drug or balloon or the like (e.g., within an hour or less after insertion).

In certain embodiments, the catheter further comprises a cuff that locates at the junction where the catheter exits the skin. In certain embodiments, the catheter further comprises a catheter hub. In certain embodiments, the catheter may be positioned in the body via a trocar. In certain embodiments, the catheter is to be placed under the skin and referred to as a "tunneled catheter."

In certain embodiments, an anti-infective hemodialysis catheter is provided. In an embodiment, the anti-infective hemodialysis catheter is a two lumen catheter. It may or may not further comprise a cuff, and may or may not be delivered using a trocar.

In certain embodiments, the medical implant is a chronic indwelling medical implant intended to be inserted and stay inside a patient for an extended period of time, such as at least for 1, 2, 3, 4, 5, or 6 days, 1, 2, 3, or 4 weeks, or 1, 2, 3, 4, 5, 6, 7, 8, 9, 10, 11, or 12 months.

A "coating," as used herein, refers to a composition that (1) adheres to the surface of at least a portion of a medical implant, and (2) comprises at least one component different from the material(s) that form the medical implant.

In certain embodiments, the coating is a layer on a medical implant that is of substantially uniform thickness. A layer is "of substantially uniform thickness" if the thickness at any position of the layer is between 70% and 130% of the average thickness of the layer. In certain embodiments, the thickness at any position of the layer is between 80% and 120%, such as between 90% and 100%

In certain other embodiments, the coating adheres to multiple non-continuous areas of the surface of a medical implant. Such a coating is referred to as "spot coating."

In certain other embodiments, the medical implant contains a plurality of reservoirs, and the composition that comprises at least one component different from the material(s) that form the medical implant adheres to the surface of the plurality of reservoirs. Such a coating is referred to as "well coating" or "pit coating." The reservoirs may be formed from divets or voids in the medical implant surface or from micropores or channels in the medical implant body.

Any of the compositions (e.g., coating compositions) described herein may be used in combination with any of the medical implants described herein to provide the anti-infective medical implants according to the present invention.

In certain embodiments, the polyurethane in the composition (e.g., in form of a coating) on the medical implant is a poly(carbonate urethane), poly(ester urethane), or poly(ether urethane).

In certain embodiments, the cellulose-derived polymer is nitrocellulose, cellulose acetate butyrate, or cellulose acetate propionate.

The anti-infective medical implant provided herein comprises a fluoropyrimidine or its analog (e.g., 5-FU) in an amount effective in reducing or inhibiting infection associated with the medical implant.

An "amount effective in reducing or inhibiting infection" refers to an amount of an anti-infective agent when used in combination with a medical implant (e.g., as a coating of the medical implant) that is sufficient in statistically significantly reducing infection associated with the medical implant when inserted into a patient with the same implant but without the anti-infective agent. Such an amount may be determined using methods known in the relevant art.

In certain embodiments, the fluoropyrimidine or its analog is released from the composition (e.g., in form of a coating) on the anti-infective medical implant at an amount effective in reducing or inhibiting infection associated with the medical implant for an extended period of time, such as at least for 1, 2, 3, 4, 5, or 6 days, 1, 2, 3, or 4 weeks, or 1, 2, 3, 4, 5, 6, 7, 8, 9, 10, 11, or 12 months. In certain embodiments, the release of the fluoropyrimidine or its analog starts upon the implantation of the anti-infective medical implant into a patient. In certain other embodiments, there is a delay before the fluoropyrimidine or its analog starts to release from the anti-infective medical implant.

In certain embodiments, the fluoropyrimidine or its analog is released from the composition (e.g., in form of a coating) during the entire residence time of the implant within the patient. For example, for a central venous catheter that may remain implanted for up to about 30 days and for a hemodialysis catheter that may remain implanted for 6 to 12 months, the fluoropyrimidine or its analog releases from the catheter beginning after implantation up until removal of the catheter from the patient. In other embodiments, the fluoropyrimidine or its analog is not released (e.g., does not dissociate) from the medical implant but is present on the surface of the medical implant in an amount effective in reducing or inhibiting infection for an extended period of time, such as at least for 1, 2, 3, 4, 5, or 6 days, 1, 2, 3, or 4 weeks, or 1, 2, 3, 4, 5, or 6 months.

In certain embodiments, the average thickness of the coating ranges form 0.5 μm to 10 μm. In certain embodiments, the average thickness of the coating is about 3-6 μm. In certain embodiments, the average thickness of the coating is about 5 μm.

In certain embodiments, the weight ratio (i.e., w/w) of the polyurethane to the cellulose or cellulose-derived polymer in the composition (e.g., in form of a coating) ranges from 1:2 to 1:4. In certain embodiments, the weight ratio of the polyurethane to the cellulose or cellulose-derived polymer in the composition is about 1:3.

In certain embodiments, the weight ratio of the fluoropyrimidine or its analog (e.g., 5-FU) to the sum of the polyurethane (e.g., poly(carbonate urethane)) and the cellulose or cellulose-derived polymer (e.g., nitrocellulose) in the composition (e.g., in form of a coating) may range from 2% to 40%, such as 5% to 25%, 10% to 20%, or 15% to 19%. In certain embodiments, the weight ratio of the fluoropyrimidine or its analog to the sum of the polyurethane and the cellulose or cellulose-derived polymer in the composition is about 15% or about 20%. In certain embodiments, the weight ratio of the fluoropyrimidine or its analog to the sum of the polyurethane and the cellulose or cellulose-derived polymer in the composition is below 20%.

The amount of fluoropyrimidine or its analog is chosen to achieve the desired level of infection control with negligible systemic exposure and/or negligible damages to surrounding host tissues. In other words, the amount of fluoropyrimidine or its analog must be high enough to prevent bacterial infection, such as bacterial growth, in, on or around the medical implant, but low enough not to damage cells in the vicinity or in contact with the medical implant, or cause systemic adverse effects on the host. For example, in certain embodiments, when a medical implant (e.g., a vascular catheter) that comprises a fluoropyrimidine or its analog is implanted into a blood vessel, the plasma concentration of the fluoropyrimidine or its analog is less than 500 ng/ml, 100 ng/ml, 50 ng/ml, 10 ng/ml, 5 ng/ml, or 1 ng/ml. In certain embodiments, when a vascular implant that comprises a fluoropyrimidine or its analog is implanted into a blood vessel, fluoropyrimidine or its analog does not across the blood vessel wall and infiltrate to the surrounding tissue at a detectable concentration (e.g., 1 ng/ml or higher).

In certain embodiments, the total dose of 5-fluorouracil applied to the medical implant, such as a central venous catheter, should not exceed 250 mg (range of 1.0 μg to 250 mg). In a particularly preferred embodiment, the total amount of drug applied to the medical implant should be in the range of 10 μg to 25 mg. The dose per unit area of the implant (i.e. the amount of drug as a function of the surface area of the portion of the implant to which drug is applied and/or incorporated) should fall within the range of 0.1 μg-1 mg per mm$^2$ of surface area. In a particularly preferred embodiment, 5-fluorouracil should be applied to the implant surface at a dose of 1.0 μg/mm$^2$-50 μg/mm$^2$. As different polymer and non-polymer coatings will release 5-fluorouracil at differing rates, the above dosing parameters should be utilized in combination with the release rate of the drug from the implant surface such that a minimum concentration of $10^{-4}$-$10^{-7}$ M of 5-fluorouracil is maintained on the implant surface. It is necessary to insure that drug concentrations on the device surface exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the surface of the implant such that anti-infective activity is maintained for a period ranging from several hours to several months. In a particularly preferred embodiment the drug is released in effective concentrations for a period ranging from 1-30 days. It should be readily evident given the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g. a compound twice as potent as 5-fluorouracil is administered at half the above parameters, a compound half as potent as 5-fluorouracil is administered at twice the above parameters, etc.).

In certain embodiments, the fluoropyrimidine (e.g., 5-FU) or its analog is present at 0.1 µg to 1 mg per cm$^2$, such as at 0.1 µg to 1 µg per cm$^2$, 1 µg to 10 µg per cm$^2$, at 10 µg to 100 µg per cm$^2$ (e.g., at about 20, 30, 40, 50, 60, 70, 80, or 90 µg per cm$^2$), at 100 µg to 1 mg per cm$^2$, 0.1 µg to 10 µg per cm$^2$, 10 µg to 1 mg per cm$^2$, 1 µg to 100 µg per cm$^2$ of the surface area of the anti-infective medical implant to which a composition that comprises the fluoropyrimidine or its analog is applied or incorporated (e.g., the surface area of the anti-infective medical implant coated with the composition). In certain embodiments, inhibition of infection (e.g., bacterial colonization) of certain types of medical implants (e.g., vascular access catheters) may be achieved by incorporation of a fluoropyrimidine or its analog (e.g., 5-FU) in the amount of about 40-100 µg per cm$^2$ of coated surface area of the anti-infective medical implant (e.g., vascular access catheters).

In certain embodiments, the fluoropyrimidine (e.g., 5-FU) or its analog is present, in terms of weight per linear cm of medical implant (e.g., a catheter or a tube), at 0.1 µg to 1 mg per linear cm of catheter or tube length to which a composition that comprises the fluoropyrimidine or its analog, a polyurethane, and cellulose or a cellulose-derived polymer is applied or incorporated (e.g., the surface area of the anti-infective coated with the composition), such as at 0.1 µg to 1 µg per cm, 1 µg to 10 µg per cm, 10 µg to 100 µg per cm (e.g., at about 20, 30, 40, 50, 60, 70, 80, or 90 µg per cm), 100 µg to 1 mg per cm, 0.1 µg to 10 µg per cm, 10 µg to 1 mg per cm, 1 µg to 100 µg per cm, of catheter or tube length of the anti-infective catheter or tube to which the fluoropyrimidine or its analog-containing polymeric composition is applied or incorporated. In certain embodiments, inhibition of infection (e.g., bacterial colonization) of certain types of medical implants (e.g., vascular access catheters or tubes) may be achieved by incorporation of a fluoropyrimidine or its analog (e.g., 5-FU) in an amount of about 10 µg to 25 µg, about 25 µg to about 75 µg, about 75 µg to about 100 µg, about 10 µg to about 40 µg, about 40 µg to about 60 µg, about 60 µg to about 100 µg, about 10 µg to 45 µg, about 45 µg to about 55 µg, or about 55 µg to about 100 µg, per linear cm of catheter or tube length to which the fluoropyrimidine or its analog-containing polymeric composition is applied or incorporated.

In certain embodiments, the anti-infective medical implant comprises 1 µg to 250 mg, such as 1 µg to 10 µg, 10 µg to 100 µg, 100 µg to 1 mg, 1 mg to 10 mg, 10 mg to 100 mg, 100 mg to 250 mg, 1 µg to 100 µg, 100 µg to 10 mg, or 10 mg to 250 mg of a fluoropyrimidine (e.g., 5-FU) or its analog. In certain embodiments, the anti-infective medical implant (e.g., a catheter or a tube) comprises about 0.2, 0.4, 0.6, 0.8, 1, 2, 3, 4, 5, 6, 7, 8, 9, or 10 mg of a fluoropyrimidine or its analog (e.g., 5-FU). In certain embodiments, anti-infective medical implants (e.g., a vascular access catheter such as a CVC) are provided that comprise a total dose of about 0.1 mg to about 0.5 mg, about 0.5 mg to about 1.5 mg, about 1.5 mg to about 10 mg, about 0.1 mg to about 0.75 mg, or about 0.75 mg to about 1.5 mg, about 0.1 mg to about 10 mg, about 0.2 mg to 4 mg of a fluoropyrimidine (e.g., 5-FU) or its analog.

Any fluoropyrimidine or its analog described above may be used (e.g., for coating on a medical implant) to provide the anti-infective medical implant according to the present invention. In certain embodiments, the fluoropyrimidine or its analog is 5-fluorouracil.

In certain embodiments, the composition (e.g., in form of a coating) may further comprise one or more secondary anti-infective agents, one or more other active agents (e.g., antithrombotic agents), or combinations thereof. Any of the secondary anti-infective agents or other active agents described above may be used in combination of a fluoropyrimidine or its analog in a coating on a medical implant according to the present invention.

In certain embodiments, a medical implant (e.g., a catheter or a tube) may have a composition that comprises a fluoropyrimidine or its analog on a portion of its surface (e.g., in form of a coating), and have a composition that comprises another active agent (e.g. an antithromobotic agent) on a different portion of its surface (e.g., in form of a coating).

In certain embodiments, the anti-infective medical implant of the present invention is a medical implant that is composed at least partially of polyurethane. A "medical implant that is composed at least partially of polyurethane," as used herein, refers to a medical implant at least a section of which is made of a composition that comprises polyurethane, and (b) in which polyurethane is not present only in a composition that further comprises a fluoropyrimidine or its analog (e.g., in the form of a coating) on the medical implant. In other words, such a medical implant has at least a section formed form a polyurethane material or a blend or copolymer of polyurethane and another polymer. In certain embodiments, polyurethane contributes to at least 60%, 70%, 80%, 90%, 95%, 98% or 99% of the weight of at least a section of the medical implant. In certain embodiments, polyurethane contributes to at least 60%, 70%, 80%, 90%, 95%, 98% or 99% of the total weight of the medical implant.

In certain embodiments, the medical implant is composed of polyurethane that is different from the polyurethane in the coating of the medical implant. In certain embodiments, the medical implant is composed of polyurethane that is the same as the polyurethane in the coating of the medical implant.

Polyurethanes useful in the production of medical implants (e.g., catheters and tubes) are well known in the art. They may be aliphatic or aromatic. In certain embodiments, polyurethanes that form catheter shafts or tubes are thermoplastic. For example, in certain embodiments, a catheter or tube can be composed of an aliphatic, thermoplastic polyurethane including poly(ester urethane) such as TECOFLEX, TECOTHANE, TECOLAST, AND TECHOPHILIC available from Lubrizol Advanced Materials, Inc., aliphatic, thermoplastic polyurethane elastomer such as PELLETHANE available from Dow, or thermoplastic poly(carbonate urethane) such as CARBOTHANE available from Lubrizol. Additional exemplary polyurethanes useful in producing catheters or tubes may be MICRO-RENATHANE® and RENAPULSE™ from Braintree Scientific. Typically, polyurethanes that form catheter shaft may range in hardness measured in terms of durometer ranging from 72A to 84D.

In certain embodiments, a medical implant, such as a catheter or tube composed at least partially of polyurethane may include up to about 20% barium sulfate, bismuth salts, and/or tungsten to make them radiopaque.

In certain embodiments where the medical implant is composed of at least partially of a polyurethane, the fluoropyrimidine or its analog is also incorporated (e.g., penetrated) into the polyurethane of which the medical implant is composed. The incorporation may occur during the process of applying or incorporating a composition that comprises a fluoropyrimidine or its analog onto a medical implant or a portion thereof, such as during the process of coating a medical implant or a portion thereof with the composition. For example, when a catheter or a tube is coated with a composition that comprises a swelling agent, the swelling agent induces swelling of the polyurethane from which the catheter or tube is made, which in turn may cause the fluoropyrimidine or its analog also present in the composition to penetrate or embed into the polyurethane from which the medical implant is made. In certain embodiments, such penetration or embedment of the fluoropyrimidine or its analog in the polyurethane that forms the implant allows sustained release of the fluoropyrimidine or its analog for a relatively long period of time (e.g., for at least 6, 7, 8, 9, 10, 11, or 12 months). In certain embodiments, such penetration of the fluoropyrimidine or its analog in the polyurethane that forms the medical implant allows the fluoropyrimidine analog if applied to the exterior surface of the medical implant (e.g., a catheter or a tube) to be eluted inside the lumen of the implant.

In certain embodiments, the anti-infective device of the present invention comprises a medical implant that has a surface that is made from a polyurethane or a blend or copolymer of polyurethane and another polymer, whereas the underlying substrate is made from material that does not comprise polyurethane. Such a medical implant is referred to as "polyurethane-clad medical implant."

In certain embodiments, the medical implant may be made of polymers other than polyurethane. Exemplary polymers include silicone such as RENASIL™ from Briantree Scientific.

In certain embodiments, an anti-infective medical implant is provided that comprises a medical implant (e.g., a catheter or a tube), and a composition (e.g., in the form of coating) on the implant, wherein (1) the coating comprises poly(carbonate urethane), nitrocellulose, and 5-fluorouracil, (2) the weight ratio of poly(carbonate urethane) to nitrocellulose in the coating ranges from 1:2 to 1:4 (e.g., about 1:3), and (3) 5-fluorouracil is present at 10 μg to 100 μg per linear cm (e.g., at about 50, 60, or 70 μg per linear cm) of the implant surface area to which the composition is applied or incorporated (e.g., coated implant surface area). In certain embodiments, the implant is only coated on its non-luminal surface or a portion thereof. In certain embodiments, the coating on the non-luminal surface or a portion thereof is about 3-7 μm (e.g., about 5 μm) thick. In certain embodiments, the total amount of 5-FU in the implant is from about 0.2 mg to about 2 mg, such as from 0.5 mg to about 1.5 mg, or about 1 mg. In certain embodiments, the weight ratio of 5-FU to the sum of poly (carbonate urethane) and nitrocellulose is below 20%.

In certain embodiments, inhibition of infection (e.g., bacterial colonization) of certain types of medical implants (e.g., vascular access catheters) may be achieved by incorporation of a fluoropyrimidine (e.g., 5-FU) in an amount of about 25 μg to about 75 μg per linear cm of the implant length to which a fluoropyrimidine or its analog-containing polymeric composition is applied or incorporated (e.g., coated implant length). The anti-infective surface of the implant (e.g., CVC's) may contain fluoropyrimidine (e.g., 5-FU) in an amount of about 40 μg to about 60 μg per linear cm or about 45 μg/linear cm to about 55 μg/linear cm.

5-FU is given intravenously (IV) for cancer therapy due to its inefficient absorption by ingestion. The doses used vary but a typical regimen is a dose of 500 mg/m$^2$ administered daily for 5 days, which is repeated in monthly cycles (Calabresi and Chabner, Chemotheapy of neoplastic disease. In: Gilman et al. (Eds), The Pharmacologic Basis of Therapeutics, 8$^{th}$ Ed. New York: Pergamon Press, p. 1227-30, 1990). Another regimen delivers as much as 5 grams over a 12-day period (Physician's Desk Reference (PDR), Fluorouracil for Injection, 1998). When the dose is given IV, plasma concentrations reach 0.1-1.0 mM (13-130 μg/ml) with a rapid infusion and levels of about 10 μM with a continuous infusion.

Published literature is available reporting the genotoxicity and carcinogenicity potential of 5-FU; the $LD_{50}$ in mammalian species is between 94-880 mg/kg (PDR 1998). In contrast, in certain embodiments, central venous catheters are provided herein that contain only about 1 mg of 5-FU, which is released gradually over several weeks. The total 5-FU content of such catheters is approximately 800-fold less than a maximum daily intravenous dosage or 5000-fold less than a typical 12-day treatment (PDR 1998). Non-clinical blood analysis has shown no systemically detectable levels of 5-FU (assay sensitivity of 1 ng/ml) at any time point after implantation of the (up to 21 days) in goats as shown in the example section.

B. Methods of Making Medical Implants Having Therapeutic Agents

Implants and other surgical or medical devices may be covered, coated, contacted, combined, loaded, filled, associated with, or otherwise adapted to release therapeutic agents compositions of the present invention in a variety of manners, including for example: (a) by directly affixing to the implant or device a therapeutic agent or composition (e.g., by either spraying the implant or device with a polymer/drug film, or by dipping the implant or device into a polymer/drug solution, or by other covalent or noncovalent means); (b) by coating the implant or device with a substance, such as a hydrogel, which will in turn absorb the therapeutic composition (or therapeutic factor above); (c) by interweaving therapeutic composition coated thread (or the polymer itself formed into a thread) into the implant or device; (d) by inserting the implant or device into a sleeve or mesh which is comprised of or coated with a therapeutic composition; (e) constructing the implant or device itself with a therapeutic agent or composition; or (f) by otherwise adapting the implant or device to release the therapeutic agent. Within preferred embodiments of the invention, the composition should firmly adhere to the implant or device during storage and at the time of insertion. The therapeutic agent or composition should also preferably not degrade during storage, prior to insertion, or when warmed to body temperature after insertion inside the body (if this is required). In addition, it should preferably coat or cover the desired areas of the implant or device smoothly and evenly, with a uniform distribution of therapeutic agent. Within preferred embodiments of the invention, the therapeutic agent or composition should provide a uniform, predictable, prolonged release of the therapeutic factor into the tissue surrounding the implant or device once it has been deployed. For vascular implants, in addition to the above properties, the composition should not render the implant thrombogenic (causing blood clots to form), or cause significant turbulence in blood flow (more than the implant itself would be expected to cause if it was uncoated).

Within certain embodiments of the invention, a therapeutic agent can be deposited directly onto all or a portion of the device (see, e.g., U.S. Pat. Nos. 6,096,070 and 6,299,604), or admixed with a delivery system or carrier (e.g., a polymer, liposome, or vitamin as discussed above) which is applied to all or a portion of the device (see the patents, patent applications, and references listed above under "Compositions and Formulations").

Within certain aspects of the invention, therapeutic agents can be attached to a medical implant using non-covalent attachments. For example, for compounds that are relatively sparingly water soluble or water insoluble, the compound can be dissolved in an organic solvent a specified concentration. The solvent chosen for this application would not result in dissolution or swelling of the polymeric device surface. The medical implant can then be dipped into the solution, withdrawn and then dried (air dry and/or vacuum dry). Alternatively, this drug solution can be sprayed onto the surface of the implant. This can be accomplished using current spray coating technology. The release duration for this method of coating would be relatively short and would be a function of the solubility of the drug in the body fluid in which it was placed.

In another aspect, a therapeutic agent can be dissolved in a solvent that has the ability to swell or partially dissolve the surface of a polymeric implant. Depending on the solvent/implant polymer combination, the implant could be dipped into the drug solution for a period of time such that the drug can diffuse into the surface layer of the polymeric device. Alternatively the drug solution can be sprayed onto all or a part of the surface of the implant. The release profile of the drug depends upon the solubility of the drug in the surface polymeric layer. Using this approach, one would ensure that the solvent does not result in a significant distortion or dimensional change of the medical implant.

If the implant is composed of materials that do not allow incorporation of a therapeutic agent into the surface layer using the above solvent method, one can treat the surface of the device with a plasma polymerization method such that a thin polymeric layer is deposited onto the device surface. Examples of such methods include parylene coating of devices, and the use of various monomers such hydrocyclosiloxane monomers, acrylic acid, acrylate monomers, methacrylic acid or methacrylate monomers. One can then use the dip coating or spray coating methods described above to incorporate the therapeutic agent into the coated surface of the implant.

For therapeutic agents (e.g., fluoropyrimidine or its analogs or secondary agents as described above) that have some degree of water solubility, the retention of these compounds on a device are relatively short-term. For therapeutic agents that contain ionic groups, it is possible to ionically complex these agents to oppositely charged compounds that have a hydrophobic component. For example, therapeutic agents containing amine groups can be complexed with compounds such as sodium dodecyl sulfate (SDS). Compounds containing carboxylic groups can be complexed with tridodecymethyammonium chloride (TDMAC). Mitoxantrone, for example, has two secondary amine groups and comes as a chloride salt. This compound can be added to sodium dodecyl sulfate in order to form a complex. This complex can be dissolved in an organic solvent which can then be dip coated or spray coated. Doxorubicin has an amine group and could thus also be complexed with SDS. This complex could then be applied to the device by dip coating or spray coating methods. Methotrexate, for example contains 2 carboxylic acid groups and could thus be complexed with TDMAC and then coated onto the medical implant.

For therapeutic agents that have the ability to form ionic complexes or hydrogen bonds, the release of these agents from the device can be modified by the use of organic compounds that have the ability to form ionic or hydrogen bonds with the therapeutic agent. As described above, a complex between the ionically charged therapeutic agent and an oppositely charged hydrophobic compound can be prepared prior to application of this complex to the medical implant. In another embodiment, a compound that has the ability to form ionic or hydrogen bond interactions with the therapeutic agent can be incorporated into the implant during the manufacture process, or during the coating process. Alternatively, this compound can be incorporated into a coating polymer that is applied to the implant or during the process of loading the therapeutic agent into or onto the implant. These agents can include fatty acids (e.g., palmitic acid, stearic acid, lauric acid), aliphatic acids, aromatic acids (e.g., benzoic acid, salicylic acid), cylcoaliphatic acids, aliphatic (stearyl alcohol, lauryl alcohol, cetyl alcohol) and aromatic alcohols alco multifunctional alcohols (e.g., citric acid, tartaric acid, pentaerithratol), lipids (e.g., phosphatidyl choline, phosphatidylethanolamine), carbohydrates, sugars, spermine, spermidine, aliphatic and aromatic amines, natural and synthetic amino acids, peptides or proteins. For example, a fatty acid such as palmitic acid can be used to modulate the release of 5-Fluoruracil from the implant.

For therapeutic agents that have the ability to form ionic complexes or hydrogen bonds, the release of these agents from the implant can be modified by the use of polymers that have the ability to form ionic or hydrogen bonds with the therapeutic agent. For example, therapeutic agents containing amine groups can form ionic complexes with sulfonic or carboxylic pendant groups or end-groups of a polymer. Examples of polymers that can be used for this application include, but are not limited to polymers and copolymers that are prepared using acrylic acid, methacrylic acid, sodium styrene sulfonate, styrene sulfonic acid, maleic acid or 2-acrylamido-2-methyl propane sulfonic acid. Polymers that have been modified by sulfonation post-polymerization can also be used in this application. The medical implant, for example, can be coated with, or prepared with, a polymer that comprises nafion, a sulfonated fluoropolymer. This medical device can then be dipped into a solution that comprises the amine-containing therapeutic agent. The amine-containing therapeutic agent can also be applied by a spray coating process. Methotrexate and doxorubicin are examples of therapeutic agents that can be used in this application.

It is known that the presence of bacteria on the implant surface can result in a localized decrease in pH. For polymers that comprise ionic exchange groups, for example, carboxylic groups, these polymers can have a localized increase in release of the therapeutic agent in response to the localized decrease in pH as a result of the presence of the bacteria. For therapeutic agents that contain carboxylic acid groups, polymers with pendant end-groups comprising primary, secondary, tertiary or quaternary amines can be used to modulate the release of the therapeutic agent.

Therapeutic agents with available functional groups can be covalently attached to the medical implant surface using several chemical methods. If the polymeric material used to manufacture the implant has available surface functional groups then these can be used for covalent attachment of the agent. For example, if the implant surface contains carboxylic acid groups, these groups can be converted to activated carboxylic acid groups (e.g., acid chlorides, succinimidyl derivatives, 4-nitrophenyl ester derivatives, etc). These activated carboxylic acid groups can then be reacted with amine functional groups that are present on the therapeutic agent (e.g., methotrexate, mitoxantrone).

For surfaces that do not contain appropriate functional groups, these groups can be introduced to the polymer surface via a plasma treatment regime. For example, carboxylic acid groups can be introduced via a plasma treatment process (e.g., the use of $O_2$ and/or $CO_2$ as a component in the feed gas mixture). The carboxylic acid groups can also be introduced using acrylic acid or methacrylic acid in the gas stream. These carboxylic acid groups can then be converted to activated carboxylic acid groups (e.g., acid chlorides, succinimidyl derivatives, 4-nitrophenyl ester derivatives, etc.) that can subsequently be reacted with amine functional groups that are present on the therapeutic agent.

In addition to direct covalent bonding to the implant surface, the therapeutic agents with available functional groups can be covalently attached to the medical implant via a linker. These linkers can be degradable or non-degradable. Linkers that are hydrolytically or enzymatically cleaved are preferred. These linkers can comprise azo, ester, amide, thioester, anhydride, or phosphoester bonds.

To further modulate the release of the therapeutic agent from the medical implant, portions of or the entire medical implant may be further coated with a polymer. The polymer coating can comprise the polymers described above. The polymer coating can be applied by a dip coating process, a spray coating process or a plasma deposition process. This coating can, if desired, be further crosslinked using thermal, chemical, or radiation (e.g., visible light, ultraviolet light, e-beam, gamma radiation, x-ray radiation) techniques in order to further modulate the release of the therapeutic agent from the medical implant.

This polymer coating can further contain agents that can increase the flexibility (e.g., plasticizer—glycerol, triethyl citrate), lubricity (e.g., hyaluronic acid), biocompatibility or hemocompatability (e.g., heparin) of the coating.

In certain embodiments, 30% to 70% of the fluoropyrimidine or its analog is released during the first 10 days after the anti-infective medical implant is implanted into a patient, and the remainder is released gradually over 20 or more days.

In certain embodiments, 20% to 70% (e.g., about 40% to about 60%) of the fluoropyrimidine or its analog (e.g., 5-FU) is released from the anti-infective composition at day 7 after implanted into a patient, 50% to 90% (e.g., about 60% to about 90%) released at day 14, and 70% to 95% (e.g., about 80% to about 95%) at day 21.

In certain embodiments, the release rate of the fluoropyrimidine or its analog from the anti-infective medical implant is substantially constant for at least 5, 10, 15, 20, 25, or 30 days. The release rate is substantially constant for a period of time when at a given time point within the period of time, the release rate is within the range of 75% to 125% of the average release rate during this period of time.

The anti-infective medical implants can be packaged and sterilized. Ethylene oxide may be used to sterilize the medical implants prepared as described herein.

IV. Clinical Applications

In order to further the understanding of the invention, discussed in more detail below are various clinical applications for the compositions, methods and devices provided herein.

Briefly, as noted above, within one aspect of the invention methods are provided for preventing, reducing, and/or inhibiting an infection associated with a medical device or implant, comprising the step of introducing into a patient a medical implant which releases a chemotherapeutic agent, wherein the chemotherapeutic agent reduces, inhibits, or prevents the growth or transmission of foreign organisms (e.g., bacteria, fungi, or viruses). As used herein, agents that reduce, inhibit, or prevent the growth or transmission of foreign organisms in a patient means that the growth or transmission of a foreign organism is reduced, inhibited, or prevented in a statistically significant manner in at least one clinical outcome, or by any measure routinely used by persons of ordinary skill in the art as a diagnostic criterion in determining the same. In a preferred embodiment, the medical implant has been covered or coated with a fluoropyrimidine (e.g., 5-FU).

Particularly preferred fluoropyrimidines or analogs thereof which are utilized within the context of the present invention should have an MIC of less than or equal to any one of $10^{-4}$M, $10^{-5}$M, $10^{-6}$M, or, $10^{-7}$M. Furthermore, particularly preferred fluoropyrimidines or analogs thereof are suitable for use at concentrations less than that 10%, 5%, or even 1% of the concentration typically used in chemotherapeutic applications (Goodman and Gilman's The Pharmacological Basis of Therapeutics. Editors J. G. Hardman, L. L. Limbird. Consulting editor A. Goodman Gilman Tenth Edition. McGraw-Hill Medical publishing division. 10th edition, 2001, 2148 pp.). Finally, the devices should preferably be provided sterile, and suitable for use in humans.

A. Vascular Catheter—Associated Infections

More than 30 million patients receive infusion therapy annually in the United States. In fact, 30% of all hospitalized patients have at least one vascular catheter in place during their stay in hospital. A variety of medical devices are used for infusion therapy including, but not restricted to, peripheral intravenous catheters, central venous catheters, total parenteral nutrition catheters, peripherally inserted central venous catheters (PIC lines), totally implanted intravascular access devices, flow-directed balloon-tipped pulmonary artery catheters, arterial lines, and long-term central venous access catheters (Hickman lines, Broviac catheters).

Unfortunately, vascular access catheters are prone to infection by a variety of bacteria and are a common cause of bloodstream infection. Of the 100,000 bloodstream infections in US hospitals each year, many are related to the presence of an intravascular device. For example, 55,000 cases of bloodstream infections are caused by central venous catheters, while a significant percentage of the remaining cases are related to peripheral intravenous catheters and arterial lines.

Bacteremia related to the presence of intravascular devices is not a trivial clinical concern: 50% of all patients developing this type of infection will die as a result (over 23,000 deaths per year) and in those who survive, their hospitalization will be prolonged by an average of 24 days. Complications related to bloodstream infections include cellulites, the formation of abscesses, septic thrombophlebitis, and infective endocarditis. Therefore, there is a tremendous clinical need to reduce the morbidity and mortality associated with intravascular catheter infections.

The most common point of entry for the infection-causing bacteria is tracking along the device from the insertion site in the skin. Skin flora spread along the outside of the device to ultimately gain access to the bloodstream. Other possible sources of infection include a contaminated infusate, contamination of the catheter hub-infusion tubing junction, and hospital personnel. The incidence of infection increases the longer the catheter remains in place and any device remaining in situ for more than 72 hours is particularly susceptible. The most common infectious agents include common skin flora such as coagulase-negative staphylococci (*S. epidermidis, S. saprophyticus*) and *Staphylococcus aureus* (particularly MRSA—methicillin-resistant *S. aureus*) which account for ⅔ of all infections. Coagulase-negative staphylococci (CNS) is the most commonly isolated organism from the blood of hospitalized patients. CNS infections tend to be indolent; often occurring after a long latent period between contamination (i.e. exposure of the medical device to CNS bacteria from the skin during implantation) and the onset of clinical illness. Unfortunately, most clinically significant CNS infections are caused by bacterial strains that are resistant to multiple antibiotics, making them particularly difficult to treat. Other organisms known to cause vascular access catheter-related infections include Enterococci (e.g. *E. coli*, VRE—vancomycin-resistant enterococci), Gram-negative aerobic bacilli, *Pseudomonas aeruginosa, Klebsiella* spp., *Serratia marcescens, Burkholderia cepacia, Citrobacter freundii, Corynebacteria* spp. and *Candida* species.

Most cases of vascular access catheter-related infection require removal of the catheter and treatment with systemic antibiotics (although few antibiotics are effective), with vancomycin being the drug of choice. As mentioned previously, mortality associated with vascular access catheter-related infection is high, while the morbidity and cost associated with treating survivors is also extremely significant.

It is therefore extremely important to develop vascular access catheters capable of reducing the incidence of bloodstream infections. Since it is impossible to predict in advance which catheters will become infected, any catheter expected to be in place longer than a couple of days would benefit from a therapeutic coating capable of reducing the incidence of bacterial colonization of the device. An ideal therapeutic coating would have one or more of the following characteristics: (a) the ability to kill, prevent, or inhibit colonization of a wide array of potential infectious agents including most or all of the species listed above; (b) the ability to kill, prevent, or inhibit colonization of bacteria (such as CNS and VRE) that are resistant to multiple antibiotics; (c) utilize a therapeutic agent unlikely to be used in the treatment of a bloodstream infection should one develop (i.e., one would not want to coat the device with a broad-acting antibiotic, for if a strain of bacteria resistant to the antibiotic were to develop on the device it would jeopardize systemic treatment of the patient since the infecting agent would be resistant to a potentially useful therapeutic).

Fluoropyrimidines (e.g., 5-FU) have a high degree of antibacterial activity against CNS (*S. epidermidis*) and *Staphylococcus aureus*—the most common causes of vascular catheter infections. It is important to note that not all anticancer agents are suitable for the practice of the present invention as several agents, including 2-mercaptopurine, 6-mercaptopurine, hydroxyurea, cytarabine, cisplatinum, tubercidin, paclitaxel, and camptothecin did not have antibacterial activity against the organisms known to cause vascular access catheter-related infections.

1. Central Venous Catheters

For the purposes of this invention, the term "Central Venous Catheters" should be understood to include any catheter or line that is used to deliver fluids (e.g., intravenous fluids, blood products, drugs, and parenteral nutrition solutions) to, as well as blood withdrawal from, the large (central) veins of the body (e.g., jugular, pulmary, femoral, iliac, inferior vena cava, superior vena cava, axillary etc.).

There are many types of central venous catheters (CVC) that vary by insertion technique, size, tip style, catheter material, and number of lumens.

There are non-tunneled percutaneously placed catheters as well as tunneled catheters. Non-tunneled CVCs are placed directly into one of the large central veins with direct access. For example, the HOHN CVC (C.R. Bard, Inc.) is a silicone, open-ended, non-tunneled catheter. The HOHN CVC may have a single or dual lumen. The dual lumen version is for multi-purpose access when two separate fluid pathways are required.

Tunneled CVCs are typically designed for long-term vascular access and for patients that lack adequate peripheral venous access. The tunneled catheter is the best choice when access to the vein is needed for long period of time and when the catheter line will be used many times each day. They are used to tunnel subcutaneously from one of the large central veins to the desired exit site and can have single, dual or triple lumens. Some may be bifurcated to aid in functionality. Tunneled CVCs are often composed of processed silicone or polyurethane. Examples of tunneled CVCs made of silicone with an open-end include, but are not limited to, the HICKMAN, LEONARD and BROVIAC CVCs (C.R. Bard, Inc., Murray Hill, N.J.). The GROSHONG CVC (C.R. Bard, Inc.) which is also a tunneled silicone CVC has a closed rounded tip style. Unlike, open-ended catheters (such as the HICKMAN, LEONARD and BROVIAC lines), the closed end has a valve or valves that allow liquids to flow in or out, but remains closed when not in use to restrict back flow and air embolisms.

Another type of tunneled CVC are the polyurethane, open-ended "power" CVCs made by C.R. Bard, Inc. For example, the POWERLINE CVC is a kink-resistant, reverse-tapered design which has an exclusive bifurcated design. The POWERLINE, POWERHOHN and POWERHICKMAN (C.R. Bard, Inc.) may be used for either long or short term indications where power injection (e.g., power injection of contrast media) is needed.

Some tunneled CVCs are very specialized in their indication of use. For example, the DU PEN Epidural Catheter (C.R. Bard, Inc.) which is a silicone based, open-ended catheter is intended for long-term access to the epidural space for the delivery of morphine to relieve pain associated with cancer.

Other types of CVCs include, but are not limited to total parenteral nutrition catheters, peripherally inserted central venous catheters, and flow-directed balloon-tipped pulmonary artery catheters. Representative examples of such CVCs are described in U.S. Pat. Nos. 3,995,623, 4,072,146 4,096, 860, 4,099,528, 4,134,402, 4,180,068, 4,385,631, 4,406,656, 4,568,329, 4,960,409, 5,176,661, 5,916,208.

CVCs can provide a suitable surface for the colonization of microorganisms. Bacteria that are present on the skin, around the catheter hubs, or surrounding the CVC insertion site can become established on the catheter surface. When bacteria that colonize on and around the catheter propagate along the catheter surface and into the intracutaneous tract, they can disseminate away from the catheter and seed into the bloodstream. This may result in systemic bloodstream infections, which can lead to significant increases in morbidity and mortality.

Although many infectious agents can colonize and infect a catheter, skin microorganisms are the most common causes of catheter-related infection. Staphylococci (*S. aureus, S. epidermidis*, and *S. pyogenes*), Enterococci (*E. coli*), Gram Negative Aerobic Bacilli, and *Pseudomonas aeruginosa* are all common causes of CRI.

Microorganisms commonly present on the skin and those associated with catheter-related infection (CRI) produce proteins that enhance their adherence properties. The production of these proteins promotes the formation of biofilms, which influences microbial resistance to host defense mechanisms. Biofilms can be defined as a highly consolidated structure composed of bacteria reversibly attached to themselves or a substrate, embedded in a matrix of polymeric substances.

Biofilm formation begins with the attachment of bacteria to a surface of the catheter, followed by cell proliferation and intracellular adhesion. A CVC first becomes coated with plasma and connective tissue proteins, such as fibronectin, fibrinogen, vitronectin, thombospondin, lamin, collagen and von Willebrand factor. These proteins then act as receptors for colonizing bacteria. Following adherence to the catheter surface, bacteria multiply and accumulate in multilayered clusters followed by differentiation into exopolysaccharide-encased mature biofilms. Within biofilms, bacteria acquire or develop different characteristics. Following adherence to the catheter surface, bacteria multiply and accumulate in multilayered clusters followed by differentiation into exopolysaccharide-encased mature biofilms. Thus the biofilm shields bacteria against immune response mechanisms and systemic antibiotics. Bacteria in biofilms are protected from host defenses and antibacterial treatments due to a number of biofilm properties. This decreased susceptibility to antimicrobial agents requires that novel strategies be developed to prevent CRIs.

The most frequent life-threatening complication of CVC use is septicemia. Other severe complications of central venous catheter infection include infective endocarditis and suppurative phlebitis of the great veins. If the device becomes infected, it must be replaced at a new site (over-the-wire exchange is not acceptable) which puts the patient at further risk to develop mechanical complications of insertion such as bleeding, pneumothorax and hemothorax. In addition, systemic antibiotic therapy is also required.

As described previously, 55,000 cases of bloodstream infections are caused by central venous catheters every year in the United States resulting in 23,000 deaths. The risk of infection increases the longer the catheter remains in place, particularly if it is used beyond 72 hours. Severe complications of central venous catheter infection also include infective endocarditis and suppurative phlebitis of the great veins. If the device becomes infected, it must be replaced at a new site (over-the-wire exchange is not acceptable) which puts the patient at further risk to develop mechanical complications of insertion such as bleeding, pneumothorax and hemothorax. In addition, systemic antibiotic therapy is also required. An effective therapy would reduce the incidence of device infection, reduce the incidence of bloodstream infection, reduce the mortality rate, reduce the incidence of complications (such as endocarditis or suppurative phlebitis), prolong the effectiveness of the central venous catheter and/or reduce the need to replace the catheter. This would result in lower mortality and morbidity for patients with central venous catheters in place.

Antibiotic-coated catheters have been developed to prevent bacterial infections, but these catheters may become colonized by bacteria that are resistant to the antibiotic coating. Antibiotic resistance creates additional complications, as these infections cannot be treated systemically with the antibiotic(s) used in the coating. Antibacterial resistance is a concern that has reduced the utilization of antibiotic-coated CVCs. Widespread acceptance and usage of antibiotic-coated catheters may be limited because of the risk of developing antibiotic resistant organisms that would require newer and/or stronger antibiotics. Additional concerns regarding the use of antibiotic-coated catheters include the additional time that must be spent preparing the coated catheter for insertion and the lack of efficacy against yeasts of the anti-infective agents that are in common use.

Some other means of preventing microbial infections have been implemented including adding cuffs to the ends of the catheter. For example, Dacron cuffs about 2 cm above the exit site may act as a barrier to ascending microorganisms and act to prevent catheter dislodgment. Other examples of catheter cuffs include the SURECUFF Tissue Ingrowth Cuff (means to fix the catheter in a subcutaneous tunnel) or VITACUFF Antimicrobial Cuff (designed to protect against infections related to vascular access catheters). Cuffs may be used as a means to incorporate an antimicrobial agent into its materials. For example, the VITACUFF is composed of two concentric layers of materials (silicone and collagen matrix which are collectively known as VITAGUARD) to decrease the incidence of infection at the outer, tissue-interfacing surface of the VITACUFF device. By adding additional antimicrobial agents to the cuff, more effective antimicrobial properties may be achieved.

In a preferred embodiment, a fluoropyrimidine ((e.g., 5-fluorouracil) or an analog thereof is formulated into a coating applied to the surface of the vascular catheter. The drug can be applied to the central venous catheter system in several manners: (a) as a coating applied to the exterior surface of the intravascular portion of the catheter and/or the segment of the catheter that traverses the skin; (b) as a coating applied to the interior and exterior surface of the intravascular portion of the catheter and/or the segment of the catheter that traverses the skin; (c) incorporated into the polymers which comprise the intravascular portion of the catheter; (d) incorporated into, or applied to the surface of, a subcutaneous "cuff" around the catheter; (e) in solution in the infusate; (f) incorporated into, or applied as a coating to, the catheter hub, junctions and/or infusion tubing; and (g) any combination of the aforementioned.

Drug-coating of, or drug incorporation into, the central venous catheter will allow bacteriocidal drug levels to be achieved locally on the catheter surface, thus reducing the incidence of bacterial colonization of the vascular catheter (and subsequent development of blood borne infection), while producing negligible systemic exposure to the drugs. Although for some agents polymeric carriers are not required for attachment of the drug to the catheter surface, several polymeric carriers are particularly suitable for use in this embodiment. Of particular interest are polymeric carriers such as polyurethanes (e.g., ChronoFlex AL 85A [CT Biomaterials], ChronoFlex AR [CT Biomaterials], HydroMed640™ [CT Biomaterials], HYDROSLIP C™ [CT Biomaterials], HYDROTHANE™ [CT Biomaterials]), acrylic or methacrylic copolymers (e.g., poly(ethylene-co-acrylic acid), cellulose-derived polymers (e.g. nitrocellulose, Cellulose Acetate Butyrate, Cellulose acetate propionate), acrylate and methacrylate copolymers (e.g., poly(ethylene-co-vinyl acetate)) as well as blends thereof. Detailed description of the compositions that may be used for coating central intravenous catheters is provided in the above Composition and Formulation section.

As central venous catheters are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the central venous catheter, dosing guidelines are provided in the above Medical Implants section.

The anti-infective central venous catheters provided herein may be used to reduce or inhibit infections associated with central venous catheters, including bacterial colonization, local infection, and infection in bloodstream associated with catheters. The anti-infective central venous catheters provided herein also may inhibit the formation of biofilm on the surface of the catheter. Such catheters comprise fluoropyrimidines or their analogs (e.g., 5-fluorouracil) that have anti-infective activities against a broad spectrum of microorganisms (e.g., gram positive bacteria). In addition, the polymeric coating on the catheters allows the fluoropyrimidines or their analogs to be released at effective concentrations for a sustained period of time.

2. Peripheral Intravenous Catheters

For the purposes of this invention, the term "Peripheral Venous Catheters" should be understood to include any catheter or line that is used to deliver fluids to the smaller (peripheral) superficial veins of the body (e.g., veins in the arm or leg). Peripheral venous catheters include radial and femoral access catheters.

Peripherally inserted central catheter (PICC or PIC line) is a form of intravenous access whereby they can be used for extended periods of time (e.g., long chemotherapy regimens, extended antibiotic therapy or total parenteral nutrition). PICCs typically provide central intravenous access for several weeks, but may remain in place for several months. PICCs are usually inserted in a peripheral vein, such as the cephalic vein, basilica vein, or brachial vein and then advanced through increasingly larger veins toward the heart until the tip rests in the distal superior vena cava.

Certain types of PICCs have multiple lumens such as the POLY PER-Q-CATH Triple-Lumen PICC (C.R. Bard) and the TWINCATH Multiple Lumen Peripheral Catheter made by Arrow International, Inc. (Reading, Pa.).

Certain types of PICCs have been approved for use in power injection, such as the polyurethane PICCs made by C.R. Bard, Inc. The POWERPICC Catheter and the POWERPICC SOLO Catheter come in single, dual or triple lumens. They are used for injection of contrast media into the bloodstream. Other power injection catheters include the XCELA Power Injectable PICC (Boston Scientific) and the PROPICC CT (Medical Components, Inc., Harleysville, Pa.). Arrow International also makes a Pressure Injectable PICC.

Some PICCs have greater radiopacity. For example, the POLY RADPICC Catheters made by C.R. Bard are specifically designed with greater radiopacity. These polyurethane-based catheters have a kink-resistant hub enhancing strength and comfort. The RADPICC catheters also made by C.R. Bard are silicone based which are available in either single or dual lumens. The VASCU-PICC II which has greater x-ray and fluoroscopic visibility is made by Medical Components. Another PICC that has greater imaging capabilities is the MORPHEUS CT PICC made by Angiodynamics Inc. (Queensbury, N.Y.).

PICCs may be open-ended or may be valved. Examples of open-ended PICCs include, but are not limited to, the polyurethane ARROW PICC (Arrow International), the polyurethane POLY PER-Q-CATH PICC and the POWERPICC Catheters (C.R. Bard) as well as the silicone PER-Q-CATH PICC (C.R. Bard). Smiths Medical (Herts, UK) makes open-ended PICCs such as the DELTEC CLINICATH and POLYFLOW PICCs.

Examples of valved PICCs include, but are not limited to, the silicone-based GROSHONG PICC lines and the polyurethane-based POWERPICC SOLO Catheter from C.R. Bard. Boston Scientific (Natick, Mass.) makes the VAXCEL PICC with PASV Valve technology.

Other peripherally inserted catheters are midline catheters. Midline catheters are inserted peripherally but unlike the PICC that ends at the heart or the largest central vein, the midline catheter tip does not extend to the heart. Typically, the midline catheter tip ends at an upstream vein. Midline catheters are also typically not used as long as PICCs. Examples of midline catheters, include those made by C.R. Bard such as the silicone open-ended midline catheters (e.g., PER-Q-CATH Plus Midline Catheter) and the silicone valved midline catheters (e.g., GROSHONG Midline Catheter). Arrow International makes the polyurethane open-ended ARROW Midline Catheter.

Peripheral venous catheters have a much lower rate of infection than do central venous catheters, particularly if they are in place for less than 72 hours. One exception is peripheral catheters inserted into the femoral vein (so called "femoral lines") which have a significantly higher rate of infection. The organisms that cause infections in a peripheral venous catheter are identical to those described above (for central venous catheters).

In a preferred embodiment, a fluoropyrimidine (e.g., 5-fluorouracil) or an analog thereof is formulated into a coating applied to the surface of the peripheral vascular catheter. The drug can be applied to the peripheral venous catheter system in several manners: (a) as a coating applied to the exterior and/or interior surface of the intravascular portion of the catheter and/or the segment of the catheter that traverses the skin; (b) incorporated into the polymers which comprise the intravascular portion of the catheter; (c) incorporated into, or applied to the surface of, a subcutaneous "cuff" around the catheter; (e) in solution in the infusate; (f) incorporated into, or applied as a coating to, the catheter hub, junctions and/or infusion tubing; and (g) any combination of the aforementioned.

The formulation and dosing guidelines for this embodiment are identical to those described for central venous catheters.

The anti-infective peripheral venous catheters provided herein may be used to reduce or inhibit infections associated with peripheral venous catheters, including bacterial colonization, local infection, and infection in bloodstream associated with catheters. The anti-infective peripheral venous catheters provided herein also may inhibit the formation of biofilm on the surface of the catheter. Such catheters comprise fluoropyrimidines (e.g., 5-fluorouracil) or their analogs that have anti-infective activities against a broad spectrum of microorganisms (e.g., gram positive bacteria). In addition, the polymeric coating on the catheters allows the fluoropyrimidines or their analogs to be released at effective concentrations for a sustained period of time.

3. Arterial Lines and Transducers

Arterial lines are used to draw arterial blood gasses, obtain accurate blood pressure readings and to deliver fluids. They are placed in a peripheral artery (typically the radial artery of the wrist) and often remain in place for several days. Arterial line catheters are typically those catheters that are used for peripheral lines. Arterial lines are often composed of a transducer setup (such as the DELTRAN pressure transducer from Utah Medical Products, Inc., Midvale, Utah) at the open end of the arterial catheter. This maintains a pressure to control the forward flow into the artery to ensure the arterial blood pressure of the patient does not result in the patient's blood climbing up the catheter line.

Arterial lines have a very high rate of infection (12-20% of arterial lines become infected) and the causative organisms are identical to those described above (for central venous catheters).

In a preferred embodiment, a fluoropyrimidine (e.g., 5-fluorouracil) or an analog thereof is formulated into a coating applied to the arterial line and transducer in several manners: (a) as a coating applied to the exterior and/or interior surface of the intravascular portion of the arterial line and/or the segment of the arterial line that traverses the skin; (b) incorporated into the polymers which comprise the intravascular portion of the arterial line; (c) incorporated into, or applied to the surface of, a subcutaneous "cuff" around the arterial line; (e) in solution in the infusate; (f) incorporated into, or applied as a coating to, the arterial line hub, junctions and/or infusion tubing; and (g) any combination of the aforementioned.

The formulation and dosing guidelines for this embodiment are identical to those described for central venous catheters.

The anti-infective arterial lines provided herein may be used to reduce or inhibit infections associated with arterial lines, including bacterial colonization, local infection, and infection in bloodstream associated with arterial lines. The anti-infective arterial lines provided herein also may inhibit the formation of biofilm on the surface of the arterial lines. Such arterial lines comprise fluoropyrimidines (e.g., 5-fluorouracil) or their analogs that have anti-infective activities against a broad spectrum of microorganisms (e.g., gram positive bacteria). In addition, the polymeric coating on the arterial lines allows the fluoropyrimidines or their analogs to be released at effective concentrations for a sustained period of time.

4. Port-Catheters

Port-catheters provide implantable accessibility for repeat access to the vascular system or to the peritoneal cavity. Ports have two main components consisting of an injection port with a self-sealing septum and a catheter. The port reservoir is implanted subcutaneously and is tunneled via central catheter to the large central vein in the chest. Port access is performed by percutaneous needle insertion using non-coring needles.

Arterial ports are implantable vascular access devices that provide repeated access to the vascular system for the delivery of medications, intravenous fluids, parenteral nutrition solutions, blood products, imaging solutions and for the withdrawal of blood samples.

Peritoneal ports with peritoneal catheters are a totally implantable access device designed to provide repeated access to the peritoneal cavity for the delivery of medications and other fluids.

Ports may be used with either open-ended catheters or valved catheters. For example, implanted ports, such as the BARDPORT, SLIMPORT and X-PORT (C.R. Bard), may be used with open-ended radiopaque silicone or CHRONOFLEX polyurethane catheters. When security against blood reflux and air embolism in the port/catheter system is required, valved catheters, such as the GROSHONG catheters, are used. Ports typically used with GROSHONG catheters are the BARDPORT and X-PORT products. Other valved implantable ports include the PASV Valved VAXCEL Implantable Port from Boston Scientific.

Other ports can be used for power injection of contrast media. For example, the POWERPORT (C.R. Bard) implanted port may be used with the POWERLOC Safety Infusion Set to deliver power injection of contrast media.

Ports may have either a single lumen or a dual lumen to facilitate multiple-infusion therapy. Most of the ports have single lumens, however, some dual lumen ports include the SLIMPORT Dual-Lumen ROSENBLATT Implanted Port and the M.R.I. Dual-Lumen Implanted Port made by C.R. Bard.

Ports may also have low, intermediate or full size profiles. For example, C.R. Bard makes low profile ports, such as the M.R.I. ULTRA SLIMPORT and the SLIMPORT Dual-Lumen ROSENBLATT Implanted Port. Intermediate profile ports made by C.R. Bard include the X-PORT (duo and inline) Dual-Lumen Implanted Ports, and full profile ports made by C.R. Bard include the Titanium DOME Implanted Port and the M.R.I. Implanted Port.

The formulation and dosing guidelines for this embodiment are identical to those described for central venous catheters.

The anti-infective port-catheters provided herein may be used to reduce or inhibit infections associated with port-catheters, including bacterial colonization, local infection, and infection in bloodstream associated with the port-catheters. The anti-infective port-catheters provided herein also may inhibit the formation of biofilm on the surface of the catheters. Such catheters comprise fluoropyrimidines (e.g., 5-fluorouracil) or their analogs that have anti-infective activities against a broad spectrum of microorganisms (e.g., gram positive bacteria). In addition, the polymeric coating on the catheters allows the fluoropyrimidines or their analogs to be released at effective concentrations for a sustained period of time.

B. Infections Associated with Dialysis Catheters

In 1997, there were over 300,000 patients in the United States with end-stage renal disease. The typical form of treatment is dialysis in the form of either hemodialysis (63%) or peritoneal dialysis (9%). A full renal transplantion occurs in the remaining cases.

In the case of hemodialysis, reliable access is required to the vascular system typically as a surgically created arteriovenous fistula (AVF; 18%), via a synthetic bridge graft (usually a PTFE arteriovenous interposition graft in the forearm or leg; 50%) or a dialysis catheter (32%). In hemodialysis, the patient's blood is pumped through the blood compartment of a dialyzer machine, exposing it to a semipermeable membrane. The cleansed blood is then returned via the circuit back to the body. Ultrafiltration occurs by increasing the hydrostatic pressure across the dialyzer membrane.

In the case of peritoneal dialysis, regular exchange of dialysate through the peritoneum is required via a double-cuffed and tunneled peritoneal dialysis catheter. In peritoneal dialysis, a sterile solution containing minerals and glucose is run through a tube into the peritoneal cavity, the abdominal body cavity around the intestine, where the peritoneal membrane acts as a semipermeable membrane. The dialysate is left there for a period of time to absorb waste products, and then it is drained out through the catheter and discarded.

Regardless of the form of dialysis employed, infection is the second leading cause of death in renal failure patients (15.5% of all deaths) after heart disease. A significant number of those infections are secondary to the dialysis procedure itself.

Hemodialysis Access Grafts

Kidney failure patients have a dysfunctional immune response that makes them particularly susceptible to infection. Infections of hemodialysis access grafts are characterized as either being early (within month; thought to be a complication of surgery) and late (after 1 month; thought to be related to access care). Over a 2 year period, approximately 2% of AVF's become infected while 11-16% of PTFE grafts will become infected on at least one occasion. Although infection can result from extension of an infection from an adjacent contaminated tissue or hematogenous seeding, the most common cause of infection is intraoperative contamination. The most common causes of infection include *Staphylococcus aureus, Enterobacteriaceae, Pseudomonas aerugenosa*, and Coagulase Negative Staphylococci.

Complications arising from hemodialysis access graft infection include sepsis, subcutaneous infection, false aneurysm formation, endocarditis, osteomyelitis, septic arthritis, haemorrhage, septic or thrombotic emboli, graft thrombosis and septic death (2-4% of all infections). Treatment often requires removal of part or all of the graft combined with systemic antibiotics.

In a preferred embodiment, a fluoropyrimidine (e.g., 5-fluorouracil) or an analog thereof is formulated into a coating applied to the surface of the components of the synthetic hemodialysis access graft. The drug can be applied in several manners: (a) as a coating applied to the external surface of the graft; (b) as a coating applied to the internal (luminal) surface of the graft; and/or (c) as a coating applied to all or parts of both surfaces. For an AVF, the drug would be formulated into a surgical implant placed around the outside of the fistula at the time of surgery.

Drug-coating of, or drug incorporation into hemodialysis access grafts will allow bacteriocidal drug levels to be achieved locally on the graft surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], ChronoFlex AR [CT Biometerials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)), collagen, PLG as well as blends thereof. Detailed description of the compositions that may be used for coating hemodialysis access graft is provided in the above Composition and Formulation section.

An effective hemodialysis access graft coating would reduce the incidence of complications such as sepsis, haemorrhage, thrombosis, embolism, endocarditis, osteomyelitis and even death. An effective coating would also decrease the number of hemodialysis access grafts requiring replacement, resulting in lower mortality and morbidity for patients with these implants.

As hemodialysis access grafts are made in a variety of configurations and sizes, the exact dose administered will vary with device size, surface area, design and portions of the graft coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the hemodialysis access graft, dosing guidelines are provided in the above Medical Implants section.

Hemodialysis Catheters

A hemodialysis catheter is a venous catheter used for hemodialysis (i.e., dialysis of the blood). It is a type of central venous catheter and may be inserted into the subclavian, internal jugular, or femoral veins. It contains two lumens: one for withdrawing blood from the patient and carries it to dialysis machine, the other for returns blood to the patient from the dialysis machine. They typically are tunneled catheters and may be cuffed or non-cuffed. Hemodialysis catheters may be used for a short period (e.g., up to 30 days), an intermediate period (e.g., 1 to 3 months), or a long period (e.g., 6-12 months). An exemplary hemodialysis catheter that may be used for a long period is HEMOSTREAM chronic dialysis catheter from Angiotech.

A variety of dialysis catheters are available for use in hemodialysis including, but not restricted to, CVCs which are totally implanted such as the Lifesite (Vasca Inc., Tewksbury, Mass.) and the Dialock (Biolink Corp., Middleboro, Mass.).

Longterm vascular access catheters, such as the HICK-MAN Hemodialysis/Apheresis CVC made by C.R. Bard are designed for hemodialysis, hemoperfusion and apheresis as well as the administration of intravenous fluids, blood products, drugs, parenteral nutrition solutions and blood withdrawal. Other catheters used for long-term hemodialysis made by C.R. Bard include the HEMOSTAR Catheter lines and the HEMOSPLIT Catheter lines made of CARBOTH-ANE radiopaque polyurethane. The SOFT-CELL Dual Lumen Catheter (C.R. Bard) is made from polyurethane in both straight and pre-curved designs which can be used in both long-term and short-term vascular access for hemodialysis, hemoperfusion or apheresis therapy.

Short-term hemodialysis catheters, such as the NIAGARA Catheter lines and BREVIA Short-Term Dialysis Catheter by C.R. Bard, are made of thermosensitive BODYSOFT polyurethane and are used for attaining temporary vascular access for less than 30 days.

Common problems associated with hemodialysis catheters are infection and clotting. The anti-infective hemodialysis catheters provided herein may be used to reduce or inhibit infections associated with hemodialysis catheters. In addition, as described above, in certain embodiments, the hemodialysis catheter may further comprise an antithromotic agent in an amount effective in reducing or inhibiting clotting associate with the catheter. For example, the antithromotic agent may be in the composition that comprises a polyurethane, cellulose or a cellulose-derived polymer, and a fluoropyrimidine or its analog, such as in form of a coating. In other embodiments, the antithromotic agent may be present on the surface (e.g., exterior surface) of a distal section of the catheter shaft while the anti-infective composition may be present on the surface (e.g., exterior surface) of a proximal section of the catheter shaft.

Peritoneal Dialysis Catheters

Peritoneal dialysis catheters are typically double-cuffed and tunneled catheters that provide access to the peritoneum. The most common peritoneal dialysis catheter designs are the TENCKHOFF Catheter, the SWAN NECK Missouri and SWAN NECK CURL CATH Missouri Peritoneal Catheters and the Toronto Western Catheter. In peritoneal dialysis, the peritoneum acts as a semipermeable membrane across which solutes can be exchanged down a concentration gradient.

Peritoneal dialysis infections are typically classified as either peritonitis or exit-site/tunnel infections (i.e. catheter infections). Exit-site/tunnel infections are characterized by redness, induration or purulent discharge from the exit site or subcutaneous portions of the catheter. Peritonitis is more a severe infection that causes abdominal pain, nausea, fever and systemic evidence of infection. Unfortunately, the peritoneal dialysis catheter likely plays a role in both types of infection. In exit-site/tunnel infections, the catheter itself becomes infected. In peritonitis, the infection is frequently the result of bacteria tracking from the skin through the catheter lumen or migrating on the outer surface (pericatheter route) of the catheter into the peritoneum. Peritoneal catheter-related infections are typically caused by *Staphylococcus aureus*, Coagulase Negative Staphylococci, *Escherichia coli*, Viridans group streptococci, Enterobacteriacae, *Corynebacterium, Branhamella, Actinobacter, Serratia, Proteus, Pseudomonas aeruginosa* and Fungi.

Treatment of peritonitis involves rapid in-and-out exchanges of dialysate, systemic antibiotics (intravenous and/or intraperitoneal administration) and often requires removal of the catheter. Complications include hospitalization, the need to switch to another form of dialysis (30%) and mortality (2%; higher if the infection is due to Enterococci, *S. aureus* or polymicrobial).

In a preferred embodiment, a fluoropyrimidine (e.g., 5-fluorouracil) or an analog thereof is formulated into a coating applied to the surface of the components of the synthetic peritoneal dialysis catheter. The drug can be applied in several manners: (a) as a coating applied to the external surface of the catheter; (b) as a coating applied to the internal (luminal) surface of the catheter; (c) as a coating applied to the superficial cuff; (d) as a coating applied to the deep cuff; (e) incorporated into the polymers that comprise the catheter; and/or (f) as a coating applied to a combination of these surfaces.

Drug-coating of, or drug incorporation into, peritoneal dialysis grafts will allow bacteriocidal drug levels to be achieved locally on the graft surface, thus reducing the incidence of bacterial colonization and subsequent development of infectious complications, while producing negligible systemic exposure to the drugs. Although for some agents polymeric carriers are not required for attachment of the drug, several polymeric carriers are particularly suitable for use in this embodiment. Of particular interest are polymeric carriers such as polyurethanes (e.g., ChronoFlex AL 85A [CT Biomaterials], ChronoFlex AR [CT Biomaterials], HydroMed640™ [CT Biomaterials], HYDROSLIP C™ [CT Biomaterials], HYDROTHANE™ [CT Biomaterials]), acrylic or methacrylic copolymers (e.g. poly(ethylene-co-acrylic acid), cellulose-derived polymers (e.g. nitrocellulose, Cellulose Acetate Butyrate, Cellulose acetate propionate), acrylate and methacrylate copolymers (e.g. poly(ethylene-co-vinyl acetate)) as well as blends thereof. Detailed description of the compositions that may be used for coating central intravenous catheters is provided in the above Composition and Formulation section.

An effective peritoneal dialysis catheter coating would reduce the incidence of complications such as hospitalization, peritonoitis, sepsis, and even death. An effective coating would also decrease the number of peritoneal dialysis catheters requiring replacement, resulting in lower mortality and morbidity for patients with these implants.

As peritoneal dialysis catheters are made in a variety of configurations and sizes, the exact dose administered will vary with device size, surface area, design and portions of the graft coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the peritoneal dialysis graft, the dosing guidelines are provided in the above Medical Implants section. The anti-infective peritoneal dialysis catheters provided herein may be used to reduce or inhibit infections associated with peritoneal dialysis catheters.

C. Infections Associated with Other Medical Devices and Implants

Implants are commonly used in the practice of medicine and surgery for a wide variety of purposes. These include implants such as drainage tubes (such as the ASPIRA Pleural Drainage Catheter from C.R. Bard), biliary T-tubes, clips, sutures, meshes, barriers (for the prevention of adhesions), anastomotic devices, conduits, irrigation fluids, packing agents, stents, staples, inferior vena cava filters, embolization agents, pumps (for the delivery of therapeutics), hemostatic implants (sponges), tissue fillers, cosmetic implants (breast implants, facial implants, prostheses), bone grafts, skin grafts, intrauterine devices (IUD), ligatures, titanium implants (particularly in dentistry), chest tubes, nasogastric tubes (such as the BARD Jejunal Feeding/Gastric Decompression Tube from C.R. Bard), percutaneous feeding tubes (such as the BARD Button Replacement Gastrostomy Devices, the BARD PEG Feeding Devices, the DUAL PORT WIZARD Low-Profile Gastrostomy Device, FASTRAC Gastric Access Port, the GAUDERER GENIE System, the PONSKY Non-Balloon Replacement Gastrostomy Tubes, and the BARD Tri-Funnel Replacement Gastrostomy Tube from C.R. Bard), colostomy devices, bone wax, and Penrose drains, hair plugs, ear rings, nose rings, and other piercing-associated implants, as well as anaesthetic solutions to name a few. Any foreign body when placed into the body is at risk for developing an infection—particularly in the period immediately following implantation.

The drug-coating, dosing, surface concentrations and release kinetics of these implants is as described in the above Composition and Formulation section and the Medical Implants section. In addition, 5-fluorouracil can be added to solutions used in medicine (storage solutions, irrigation fluids, saline, mannitol, glucose solutions, lipids, nutritional fluids, and anaesthetic solutions) to prevent infection transmitted via infected solutions/fluids used in patient management.

It should be readily evident to one of skill in the art that any of the previously mentioned agents, or derivatives and analogues thereof, can be utilized to create variation of the above compositions without deviating from the spirit and scope of the invention.

The following examples are provided by way of illustration, and not by way of limitation.

EXAMPLES

Example 1

MIC Determination by Microtitre Broth Dilution Method

A. MIC Assay of Various Gram Negative and Positive Bacteria

MIC assays were conducted essentially as described by Amsterdam, D. 1996. Susceptibility testing of antimicrobials in liquid media, p. 52-111. In Loman, V., ed. Antibiotics in laboratory medicine, 4th ed. Williams and Wilkins, Baltimore, Md. Briefly, a variety of compounds were tested for antibacterial activity against isolates of P. aeruginosa, K. pneumoniae, E. coli, S. epidermidis and S. aureus in the MIC (minimum inhibitory concentration assay under aerobic conditions using 96 well polystyrene microtitre plates (Falcon 1177), and Mueller Hinton broth at 37° C. incubated for 24 h. (MHB was used for most testing except C721 (S. pyogenes), which used Todd Hewitt broth, and Haemophilus influenzae, which used Haemophilus test medium (HTM)) Tests were conducted in triplicate. The results are provided below in Table 1.

TABLE 1

Minimum Inhibitory Concentrations of Therapeutic Agents Against Various Gram Negative and Positive Bacteria

| | Bactrial Strain | | | | | |
|---|---|---|---|---|---|---|
| Drug | P. aeruginosa PAE/K799 H187 Wt Gram− | K. pneumoniae ATCC13883 C238 wt Gram− | E. coli UB1005 C498 wt Gram− | S. aureus ATCC25923 C622 wt Gram+ | S. epidermidis C621 wt Gram+ | S. pyogenes C721 wt Gram+ |
| doxorubicin | $10^{-5}$ | $10^{-6}$ | $10^{-4}$ | $10^{-5}$ | $10^{-6}$ | $10^{-7}$ |
| mitoxantrone | $10^{-5}$ | $10^{-6}$ | $10^{-5}$ | $10^{-5}$ | $10^{-5}$ | $10^{-6}$ |
| 5-fluorouracil | $10^{-5}$ | $10^{-6}$ | $10^{-6}$ | $10^{-7}$ | $10^{-7}$ | $10^{-4}$ |

TABLE 1-continued

Minimum Inhibitory Concentrations of Therapeutic Agents
Against Various Gram Negative and Positive Bacteria

| | Bactrial Strain | | | | | |
|---|---|---|---|---|---|---|
| Drug | P. aeruginosa PAE/K799 H187 Wt Gram− | K. pneumoniae ATCC13883 C238 wt Gram− | E. coli UB1005 C498 wt Gram− | S. aureus ATCC25923 C622 wt Gram+ | S. epidermidis C621 wt Gram+ | S. pyogenes C721 wt Gram+ |
| methotrexate | N | $10^{-6}$ | N | $10^{-5}$ | N | $10^{-6}$ |
| etoposide | N | $10^{-5}$ | N | $10^{-5}$ | $10^{-6}$ | $10^{-5}$ |
| camptothecin | N | N | N | N | $10^{-4}$ | N |
| hydroxyurea | $10^{-4}$ | N | N | N | N | $10^{-4}$ |
| cisplatin | $10^{-4}$ | N | N | N | N | N |
| tubercidin | N | N | N | N | N | N |
| 2-mercaptopurine | N | N | N | N | N | N |
| 6-mercaptopurine | N | N | N | N | N | N |
| Cytarabine | N | N | N | N | N | N |

Activities are in Molar concentrations
Wt = wild type
N = No activity

B. MIC of Antibiotic-Resistant Bacteria

Various concentrations of the following compounds, mitoxantrone, cisplatin, tubercidin, methotrexate, 5-fluorouracil, etoposide, 2-mercaptopurine, doxorubicin, 6-mercaptopurine, camptothecin, hydroxyurea and cytarabine were tested for antibacterial activity against clinical isolates of a methicillin resistant S. aureus and a vancomycin resistant pediocoocus clinical isolate in an MIC assay as described above. Compounds which showed inhibition of growth (MIC value of <1.0×10−3) included: mitoxantrone (both strains), methotrexate (vancomycin resistant pediococcus), 5-fluorouracil (both strains), etoposide (both strains), and 2-mercaptopurine (vancomycin resistant pediococcus).

Example 2

Catheter—Dip Coating—Non-Degradable Polymer

A coating solution is prepared by dissolving 20 g ChronoFlex Al 85A (CT Biomaterials) in 100 mL DMAC:THF (40:60) at 50° C. with stirring. Once dissolved, the polymer solution is cooled to room temperature. 20 mg mitoxantrone is added to 2 mL of the polyurethane solution. The solution is stirred until a homogenious mixture is obtained. Polyurethane 7 French tubing is dipped into the polymer/drug solution and then withdrawn. The coated tube is air dried (80° C.). The sample is then dried under vacuum to further reduce the residual solvent in the coating.

Example 3

Catheter—Dip Coating—Degradable Polymer

A coating solution is prepared by dissolving 2 g PLG (50:50) in 10 mL dichloromethane:methanol (70:30). Once dissolved, 20 mg mitoxantrone is added to the polymer solution. Once the solution is a homogeneous solution, polyurethane 7 French tubing is dipped into the solution and then withdrawn. The coated tube is air dried. The sample is then dried under vacuum to further reduce the residual solvent in the coating.

Example 4

Catheter—Dip Coating—Drug Only 1 mL methanol is added to 20 mg mitoxantrone. Polyurethane 7 French tubing is dipped into the solution and then withdrawn. The coated tube is air dried. The sample is then dried under vacuum to further reduce the residual solvent in the coating.

Example 5

Catheter—Dip Coating—Drug Impregnation 0.6 mL methanol is added to 20 mg mitoxantrone. 1.4 mL DMAC is added slowly. Polyurethane 7 French tubing is dipped into the solution. After various periods of time (2 min, 5 min, 10 min, 20 min, 30 min) the tube was withdrawn. The coated tube is air dried (80° C.). The sample is then dried under vacuum to further reduce the residual solvent in the coating.

Example 6

Tympanostomy Tubes—Dip Coating—Non-Degradable Polymer

A coating solution is prepared by dissolving 20 g ChronoFlex Al 85A (CT Biomaterials) in 100 mL DMAC:THF (50:50) at 50° C. with stirring. Once dissolved, the polymer solution is cooled to room temperature. 20 mg mitoxantrone is added to 2 mL of the polyurethane solution. The solution is stirred until a homogenious mixture is obtained. A stainless steel tympanostomy tube is dipped into the polymer/drug solution and then withdrawn. The coated tube is air dried (80° C.). The sample is then dried under vacuum to further reduce the residual solvent in the coating.

Example 7

Catheter—Dip Coating—Non-Degradable Polymer

A coating solution is prepared by dissolving 20 g ChronoFlex Al 85A (CT Biomaterials) in 100 mL THF at 50° C. with stirring. Once dissolved, the polymer solution is cooled to room temperature. 20 mg etoposide is added to 2 mL of the polyurethane solution. The solution is stirred until a homogenious mixture is obtained. Polyurethane 7 French tubing is dipped into the polymer/drug solution and then withdrawn.

The coated tube is air dried (80 C). The sample is then dried under vacuum to further reduce the residual solvent in the coating.

Example 8

Catheter—Dip Coating—Degradable Polymer

A coating solution is prepared by dissolving 2 g PLG (50:50) in 10 mL dichloromethane:methanol (70:30). Once dissolved, 20 mg etoposide is added to the polymer solution. Once the solution is a homogeneous solution, polyurethane 7 French tubing is dipped into the solution and then withdrawn. The coated tube is air dried. The sample is then dried under vacuum to further reduce the residual solvent in the coating.

Example 9

Catheter—Dip Coating—Drug Only 1 mL THF is added to 20 mg etoposide. Polyurethane 7 French tubing is dipped into the solution and then withdrawn. The coated tube is air dried. The sample is then dried under vacuum to further reduce the residual solvent in the coating.

Example 10

Catheter—Dip Coating—Drug Impregnation 0.6 mL methanol is added to 1.4 mL DMAC which contains 20 mg etoposide. Polyurethane 7 French tubing is dipped into the solution. After various periods of time (2 min, 5 min, 10 min, 20 min, 30 min) the tube was withdrawn. The coated tube is air dried (80° C.). The sample is then dried under vacuum to further reduce the residual solvent in the coating.

Example 11

Tympanostomy Tubes—Dip Coating—Non-Degradable Polymer

A coating solution is prepared by dissolving 20 g ChronoFlex Al 85A (CT Biomaterials) in 100 mL DMAC:THF (50:50) at 50° C. with stirring. Once dissolved, the polymer solution is cooled to room temperature. 20 mg etoposide is added to 2 mL of the polyurethane solution. The solution is stirred until a homogenious mixture is obtained. A stainless steel tympanostomy tube is dipped into the polymer/drug solution and then withdrawn. The coated tube is air dried (80° C.). The sample is then dried under vacuum to further reduce the residual solvent in the coating.

Example 12

Covalent Attachment of Doxorubicin to a Polymer Coated Device

A piece of polyurethane 7 French tubing, with and without an oxygen plasma pretreatment step, is dipped into a solution of 5% (w/w) poly(ethylene-co acrylic acid) in THF. The sample was dried at 45° C. for 3 hours. The coated tubing was then dipped into a water:methanol (30:70) solution that contained 1-(3-dimethylaminopropyl)-3-ethylcarbodiimide (EDC) and 20 mg/mL Doxorubicin. After various times (15 min, 30 min, 60 min 120 min) the tubing is removed from the solution and dried at 60° C. for 2 hours followed by vacuum drying for 24 hours.

Example 13

Covalent Attachment of Doxorubicin to a Device Surface

A piece of polyurethane 7 French tubing that has undergone a oxygen plasma pretreatment step is dipped into a water:methanol (30:70) solution that contained 1-(3-dimethylaminopropyl)-3-ethylcarbodiimide (EDC) and 20 mg/mL Doxorubicin. After various times (15 min, 30 min, 60 min 120 min) the tubing is removed from the solution and dried at 60° C. for 2 hours followed by vacuum drying for 24 hours.

Example 14

Impregnation of 5-Fluorouracil into Polyurethane Catheter

A solution was prepared by dissolving 100 mg of 5-Fluorouracil into 20 ml anhydrous methanol. Polyurethane catheter tubing was immersed in this solution for 16 hours. The catheter tubing was vacuum dried at 50° C. for 16 hours.

Example 15

Impregnation of Mitoxantrone into Polyurethane Catheter

A solution was prepared by dissolving 20 mg of Mitoxantrone-2HCl into 20 ml anhydrous methanol. Polyurethane catheter tubing was immersed in this solution for 16 hours. The catheter tubing was vacuum dried at 50° C. for 16 hours.

Example 16

Impregnation of Doxorubicin into Polyurethane Catheter

A solution was prepared by dissolving 20 mg of Doxorubicin-HCl into 20 ml anhydrous methanol. Polyurethane catheter tubing was immersed in this solution for 16 hours. The catheter tubing was vacuum dried at 50° C. for 16 hours.

Example 17

Polyurethane Dip Coating with 5-Fluorouracil

A solution was prepared by dissolving 125 mg 5-Fluorouracil and 2.5 g of Chronoflex AL85A (CT Biomaterials) in 50 ml of THF at 55° C. The solution was cooled to room temperature. Polyurethane catheters were weighted at one end and dipped in solution and then removed immediately. This process was repeated three times with 1 minute drying time interval between each dipping process. The catheter tubing was vacuum dried at 50° C. for 16 hours.

Example 18

Polyurethane Dip Coating with 5-Fluorouracil and Palmitic Acid

A solution was prepared by dissolving 125 mg 5-Fluorouracil, 62.5 mg of palmitic acid, and 2.437 g of Chronoflex AL85A (CT Biomaterials) in 50 ml of THF at 55° C. The solution was cooled to room temperature. Polyurethane catheters were weighted at one end and dipped in solution and then removed immediately. This process was repeated three times with a 1 minute drying time interval between each dipping process. The catheter tubing was vacuum dried at 50° C. for 16 hours.

Example 19

Catheter Dip Coating with Nafion and Mitoxantrone

Catheters are weighted at one end and dipped into 5% Nafion solution (Dupont) and then removed immediately. This process was repeated three times with a 1 minute drying time interval between each dipping process. The catheter tubing was dried at room temperature for 2 hours. A solution was prepared with 1 mg of mitoxantrone-2HCl in 40 ml of deionized water. The catheter tubing was immersed in the solution for 5 minutes, and then was washed with deionized water and dried at room temperature.

Example 20

Catheter Dip Coating with Nafion and Doxorubicin

Catheters are weighted at one end and dipped into 5% Nafion solution (Dupont) and then removed immediately. This process was repeated three times with a 1 minute drying time interval between each dipping process. The catheter tubing was dried at room temperature for 2 hours. A solution was prepared with 1 mg of doxorubicin-HCl in 40 ml of deionized water. The catheter tubing was immersed in the solution for 5 minutes, and then was washed with deionized water and dried at room temperature.

Example 21

Preparation of Release Buffer

The release buffer was prepared by adding 8.22 g sodium chloride, 0.32 g sodium phosphate monobasic (monohydrate) and 2.60 g sodium phosphate dibasic (anhydrous) to a beaker. 1L HPLC grade water was added and the solution was stirred until all the salts were dissolved. If required, the pH of the solution was adjusted to pH 7.4±0.2 using either 0.1N NaOH or 0.1N phosphoric acid.

Example 22

Release Study to Determine Release Profile of the Therapeutic Agent from a Catheter A sample of the therapeutic agent-loaded catheter was placed in a 15 mL culture tube. 15 mL release buffer (Example 21) was added to the culture tube. The tube was sealed with a Teflon lined screw cap and was placed on a rotating wheel in a 37° C. oven. At various time point, the buffer is withdrawn from the culture tube and is replaced with fresh buffer. The withdrawn buffer is then analysed for the amount of therapeutic agent contained in this buffer solution.

Example 23

HPLC Analysis of Therapeutic Agents in Release Buffer

The following chromatographic conditions were used to quantify the amount of the therapeutic agent in the release medium:

| Therapeutic Agent | Column | Mobile Phase | Flow Rate (mL/min) | Run Time (min) | Injection Volume (uL) | Detection Wavelength (nm) |
|---|---|---|---|---|---|---|
| 5-Fluorouracil | YMC ODS-AQ 150 × 4.6 mm, 5 um | PBS, pH 6.8 | 1 | 8 | 100 | 268 |
| Doxorubicin | ACE 5 (V02-742) 150 × 4 mm | 20% CAN, 26% Methanol, 54% PBS (pH 3.6) | 1 | 10 | 10 | 254 |
| Mitoxantrone | ACE 5 C18, 150 × 4 mm, 5 um | Phosphate buffer (pH 2.3) | 1 | 4 | 10 | 658 |

Example 24

Effect of Palmitic Acid on the Release Profile of 5-Fluorouracil from a Polyurethane Film A 25% (w/v) Chronoflex AL 85A (CT Biomaterials) solution was prepared in THF. 50 mg 5-fluorouracil was weighed into each of 4 glass scintillation vials. Various amount of palmitic acid were added to each vial. 20 mL of the polyurethane solution was added to each scintillation vial. The samples were rotated at 37° C. until the solids had all dissolved. Samples were then cast as films using a casting knife on a piece of release liner. Samples were air dried and then dried overnight under vacuum. A portion of these samples were used to perform release studies (Example 22). FIG. 1 show the effect of palmitic acid on the release profile of 5-fluorouracil.

Example 25

Radial Diffusion Assay for Testing Drug Impregnated Catheters Against Various Strains of Bacteria An overnight bacterial culture was diluted 1 to 5 to a final volume of 5 mls fresh Mueller Hinton broth. Then 100 μl of the diluted bacterial culture were spread onto Mueller Hinton agar plates. A test material (e.g., catheter tubing), with or without drug, was placed on the center of the plate. For example, catheters are typically 1 cm long and about 3 mm in diameter (which may be made of polyurethane, silicon or other suitable material) and are loaded with drug either through dip-coating or through use of a drug-impregnated coating. The plates were incubated at 37° C. for 16-18 hours. The zone of clearing around a test material was then measured (e.g., the distance from the catheter to where bacterial growth is inhibited), which indicated the degree of bacterial growth prevention. Various bacterial strains that may be tested include, but are not limited to, the following: *E. coli* C498 UB1005, *P. aeruginosa* H187, *S. aureus* C622 ATCC 25923, and *S. epidermidis* C621.

One cm polyurethane catheters coated with 5-fluorouracil at several concentrations (2.5 mg/mL and 5.0 mg/mL) were examined for their effect against *S. aureus*. The zone of inhibition around the catheters coated in a solution of 2.5 mg/mL 5-Fluorouracil and placed on Mueller Hinton agar plates as described above was 35×39 mm, and for the catheters coated in a solution of 5.0 mg/mL 5-Fluorouracil was 30×37 mm. Catheters without drug showed no zone of inhibition. These results demonstrate the efficacy of 5-fluorouracil coated on a catheter at inhibiting the growth of *S. aureus*.

Example 26

Preparation of Coated Central Venous Catheters

CVC's were cleaned from their proximal ends of the body to the distal tips by wiping with VWR SPEC-WIPE® 7 Wiper that was wetted with 75/25 IPA/MEK. The catheters were allowed to dry for a minimum of 60 minutes at ambient temperature.

The catheters were then loaded onto the angle brackets that were used as fixtures for coating. The coating cup was placed on the catheter, and the angle bracket was loaded onto the coating machine. A coating solution prepared in accordance with the invention was added to the coating cups and the catheters were coated. During the process the inner lumens of the catheters were air purged to ensure that the lumen and ports are free from coating solution occlusion.

Figure 2B:
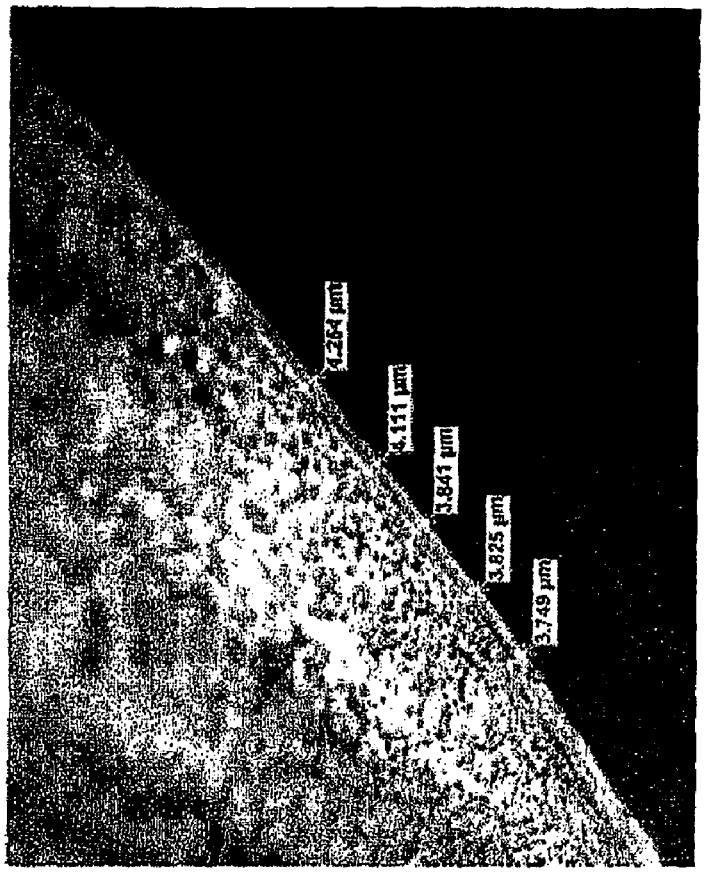
FIG. 2B is a microscopic picture of a CVC coated with a composition comprising 5-FU according to the method of Example 26.
Figure 2A:
FIG. 2A is a microscopic picture of an uncoated CVC.

The coated catheters were removed from the coating machine and dried at 85±5° C. for 20 minutes in a vented oven to remove residual solvents to acceptable levels. The coated catheters were removed from the oven and cooled. The coated catheters were visually inspected under 10× magnification for particles in the coating, damage of the catheter surface, imperfections, and occlusions. FIGS. 2A and 2B show uncoated CVC and 5-FU coated CVC, respectively.

As shown in FIG. 2B, the resulting catheter was uniformly coated on its exterior surface. In addition, the coating did not block the outlet ports and had good adhesion to the catheter under both wet and dry conditions.

The coated catheters were sterilized using 10% ethylene oxide (EtO)/90% HFCF gas.

The total amount of drug on the coated catheters was measured and the values were expressed as total amount per catheter (μg) and amount per unit catheter length (μg/cm). 5-FU was exhaustively extracted from the coated portion of the catheter in methanol with sonication and the extracts were then analyzed by high performance liquid chromatography (HPLC). An average drug loading of 969±23 μg of 5-FU/coated catheter was determined from the analysis of four separate CVC lots.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for reducing or inhibiting infection associated with a medical implant, comprising the step of introducing into a patient a medical implant which has been covered or coated with an antimicrobially effective amount of a fluoropyrimidine or an analog thereof.

2. The method according to claim 1 wherein said fluoropyrimidine is 5-fluorouracil.

3. The method according to claim 1 wherein said fluoropyrimidine is floxuridine.

4. The method according to claim 1 wherein said composition further comprises a polymer.

5. The method according to claim 4 wherein said polymer is a non-biodegradable polymer.

6. The method according to claim 4 wherein said polymer is a polyurethane, cellulose or a cellulose-derived polymer, or a combination of polyurethane and cellulose or a cellulose-derived polymer.

7. The method according to claim 1 wherein said medical implant is a vascular catheter.

8. The method according to claim 1 wherein said medical implant is a dialysis catheter.

* * * * *